US008652212B2

(12) United States Patent  
Case et al.

(10) Patent No.: US 8,652,212 B2  
(45) Date of Patent: Feb. 18, 2014

(54) ORTHOPEDIC COMPONENT OF LOW STIFFNESS

(75) Inventors: Kirt L. Case, Warsaw, IN (US); Oludele O. Popoola, Granger, IN (US); Robby Kissling, Warsaw, IN (US); Brion R. Mimnaugh, North Webster, IN (US); Archie W. Newsome, Mentone, IN (US); Clarence M. Panchison, Warsaw, IN (US); Dirk L. Pletcher, Walkerton, IN (US); Randy L. Schlemmer, Bremen, IN (US); Zhibin Fang, Warsaw, IN (US); Juan Vivanco, Madison, WI (US); Alicia Rufner, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 327 days.

(21) Appl. No.: 12/362,159

(22) Filed: Jan. 29, 2009

(65) Prior Publication Data

US 2009/0192610 A1      Jul. 30, 2009

Related U.S. Application Data

(60) Provisional application No. 61/104,870, filed on Oct. 13, 2008, provisional application No. 61/038,281, filed on Mar. 20, 2008, provisional application No. 61/024,737, filed on Jan. 30, 2008, provisional application No. 61/024,778, filed on Jan. 30, 2008.

(51) Int. Cl.  
*A61F 2/32* (2006.01)

(52) U.S. Cl.  
USPC ..................... 623/22.21; 623/22.32

(58) Field of Classification Search  
USPC ............................ 623/22.21–22.46  
See application file for complete search history.

(56) References Cited

U.S. PATENT DOCUMENTS

| 5,282,861 A | 2/1994 | Kaplan |
| 5,414,049 A | 5/1995 | Sun et al. |

(Continued)

FOREIGN PATENT DOCUMENTS

| AU | 2006283596 A1 | 1/2007 |
| AU | 2006350369 A1 | 8/2008 |

(Continued)

OTHER PUBLICATIONS

James B Stiehl, MD, "Trabecular Metal in Hip Reconstructive Surgery", Jul. 2005, Orthopedics, 28 (7), pp. 662-670.*

(Continued)

*Primary Examiner* — Bruce E Snow  
*Assistant Examiner* — Brian Dukert  
(74) *Attorney, Agent, or Firm* — Schwegman, Lundberg & Woessner, P.A.

(57) ABSTRACT

An orthopedic component having multiple layers that are selected to provide an overall modulus that is substantially lower than the modulus of known orthopedic components to more closely approximate the modulus of the bone into which the orthopedic component is implanted. In one exemplary embodiment, the orthopedic component is an acetabular shell. For example, the acetabular shell may include an outer layer configured for securement to the natural acetabulum of a patient and an inner layer configured to receive an acetabular liner. The head of a femoral prosthesis articulates against the acetabular liner to replicate the function of a natural hip joint. Alternatively, the inner layer of the acetabular shell may act as an integral acetabular liner against which the head of the femoral prosthesis articulates.

19 Claims, 13 Drawing Sheets

(56) References Cited

U.S. PATENT DOCUMENTS

| | | |
|---|---|---|
| 5,577,368 A | 11/1996 | Hamilton et al. |
| 5,721,334 A | 2/1998 | Burstein et al. |
| 5,753,182 A | 5/1998 | Higgins |
| 5,824,411 A | 10/1998 | Shalaby et al. |
| 5,827,904 A | 10/1998 | Hahn |
| 5,879,400 A | 3/1999 | Merrill et al. |
| 6,017,975 A | 1/2000 | Saum et al. |
| 6,087,553 A | 7/2000 | Cohen et al. |
| 6,156,845 A | 12/2000 | Saito et al. |
| 6,184,265 B1 | 2/2001 | Hamilton et al. |
| 6,228,900 B1 | 5/2001 | Shen et al. |
| 6,231,804 B1 | 5/2001 | Yamauchi et al. |
| 6,245,276 B1 | 6/2001 | McNulty |
| 6,277,390 B1 | 8/2001 | Schaffner |
| 6,432,349 B1 | 8/2002 | Pletcher |
| 6,437,048 B1 | 8/2002 | Saito et al. |
| 6,448,315 B1 | 9/2002 | Lidgren et al. |
| 6,461,617 B1 | 10/2002 | Shone et al. |
| 6,464,926 B1 | 10/2002 | Merrill et al. |
| 6,503,439 B1 | 1/2003 | Burstein |
| 6,558,794 B1 | 5/2003 | Fehrenbacher |
| 6,562,540 B2 | 5/2003 | Saum et al. |
| 6,620,198 B2 | 9/2003 | Burstein et al. |
| 6,627,141 B2 | 9/2003 | McNulty et al. |
| 6,641,617 B1 | 11/2003 | Merrill et al. |
| 6,664,308 B2 | 12/2003 | Sun |
| 6,664,317 B2 | 12/2003 | King, III |
| 6,692,679 B1 | 2/2004 | McNulty |
| 6,786,933 B2 | 9/2004 | Merrill et al. |
| 6,818,020 B2 | 11/2004 | Sun |
| 6,818,172 B2 | 11/2004 | King et al. |
| 6,852,772 B2 | 2/2005 | Muratoglu et al. |
| 6,853,772 B2 | 2/2005 | Battiato |
| 6,872,764 B2 | 3/2005 | King, III |
| 6,933,026 B2 | 8/2005 | Mauze |
| 7,094,472 B2 | 8/2006 | DuPlessis et al. |
| 7,160,492 B2 | 1/2007 | King |
| 7,166,650 B2 | 1/2007 | Muratoglu et al. |
| 7,214,764 B2 | 5/2007 | King |
| 7,259,198 B2 | 8/2007 | Vaillant |
| 7,304,097 B2 | 12/2007 | Muratoglu et al. |
| 7,335,697 B2 | 2/2008 | King et al. |
| 7,384,430 B2 | 6/2008 | Greer |
| 7,431,874 B2 | 10/2008 | Muratoglu et al. |
| 7,435,372 B2 | 10/2008 | Mimnaugh et al. |
| 7,445,641 B1 | 11/2008 | Ornberg et al. |
| 7,498,365 B2 | 3/2009 | Muratoglu et al. |
| 7,507,774 B2 | 3/2009 | Muratoglu et al. |
| 7,569,620 B2 | 8/2009 | Muratoglu et al. |
| 7,615,075 B2 | 11/2009 | Kunze et al. |
| 7,635,725 B2 | 12/2009 | Bellare et al. |
| 7,683,133 B2 | 3/2010 | King et al. |
| 7,790,095 B2 | 9/2010 | Muratoglu et al. |
| 7,806,064 B2 | 10/2010 | Wellman |
| 7,833,452 B2 | 11/2010 | Muratoglu et al. |
| 7,846,376 B2 | 12/2010 | Abt et al. |
| 7,863,348 B2 | 1/2011 | Abt et al. |
| 8,129,440 B2 | 3/2012 | Rufner et al. |
| 8,178,594 B2 | 5/2012 | Rufner et al. |
| 2001/0027345 A1 | 10/2001 | Merrill et al. |
| 2001/0049401 A1 | 12/2001 | Salovey et al. |
| 2002/0007219 A1 | 1/2002 | Merrill et al. |
| 2002/0156536 A1 | 10/2002 | Harris et al. |
| 2003/0013781 A1 | 1/2003 | Merrill et al. |
| 2003/0045603 A1 | 3/2003 | Salovey et al. |
| 2003/0105182 A1 | 6/2003 | Merrill et al. |
| 2003/0119935 A1 | 6/2003 | Merrill et al. |
| 2003/0127778 A1 | 7/2003 | Scott et al. |
| 2003/0149125 A1 | 8/2003 | Muratoglu |
| 2003/0158287 A1 | 8/2003 | Salovey et al. |
| 2003/0212161 A1 | 11/2003 | McKellop |
| 2004/0051213 A1 | 3/2004 | Muratoglu |
| 2004/0098127 A1 | 5/2004 | Charlebois et al. |
| 2004/0156879 A1 | 8/2004 | Muratoglu et al. |
| 2004/0265165 A1 | 12/2004 | King |
| 2005/0006821 A1 | 1/2005 | Merrill et al. |
| 2005/0056971 A1 | 3/2005 | Merrill et al. |
| 2005/0059750 A1 | 3/2005 | Sun et al. |
| 2005/0096749 A1 | 5/2005 | Merrill et al. |
| 2005/0124718 A1 | 6/2005 | Muratoglu et al. |
| 2005/0125074 A1 | 6/2005 | Salovey et al. |
| 2005/0146070 A1 | 7/2005 | Muratoglu et al. |
| 2005/0165495 A1* | 7/2005 | Merrill et al. ............... 623/23.58 |
| 2005/0194722 A1 | 9/2005 | Muratoglu et al. |
| 2005/0194723 A1 | 9/2005 | Muratoglu et al. |
| 2005/0267594 A1 | 12/2005 | Merrill et al. |
| 2006/0079597 A1 | 4/2006 | Muratoglu et al. |
| 2006/0115668 A1 | 6/2006 | King et al. |
| 2006/0264541 A1 | 11/2006 | Lederer et al. |
| 2007/0004818 A1 | 1/2007 | Muratoglu et al. |
| 2007/0043137 A1 | 2/2007 | Muratoglu et al. |
| 2007/0059334 A1 | 3/2007 | Abt et al. |
| 2007/0077268 A1 | 4/2007 | King et al. |
| 2007/0114702 A1 | 5/2007 | Muratoglu et al. |
| 2007/0149660 A1 | 6/2007 | Kumer et al. |
| 2007/0191504 A1 | 8/2007 | Muratoglu |
| 2007/0219641 A1 | 9/2007 | Dorr et al. |
| 2007/0232762 A1 | 10/2007 | Ernsberger et al. |
| 2007/0265369 A1 | 11/2007 | Muratoglu et al. |
| 2007/0267030 A1 | 11/2007 | Muratoglu et al. |
| 2007/0275030 A1 | 11/2007 | Muratoglu et al. |
| 2007/0293647 A1 | 12/2007 | McKellop et al. |
| 2008/0039545 A1 | 2/2008 | Muratoglu et al. |
| 2008/0067724 A1 | 3/2008 | Muratoglu et al. |
| 2008/0090933 A1 | 4/2008 | Muratoglu et al. |
| 2008/0090934 A1 | 4/2008 | Muratoglu et al. |
| 2008/0119582 A1* | 5/2008 | Muratoglu et al. ............. 522/79 |
| 2008/0133018 A1 | 6/2008 | Salovey et al. |
| 2008/0133021 A1 | 6/2008 | Shen et al. |
| 2008/0139137 A1 | 6/2008 | Guo et al. |
| 2008/0140196 A1 | 6/2008 | Schroeder et al. |
| 2008/0214692 A1 | 9/2008 | Muratoglu et al. |
| 2008/0215142 A1 | 9/2008 | Muratoglu et al. |
| 2008/0262120 A1 | 10/2008 | Muratoglu |
| 2008/0274161 A1 | 11/2008 | Muratoglu et al. |
| 2008/0293856 A1 | 11/2008 | Kumer et al. |
| 2008/0319137 A1 | 12/2008 | Rufner et al. |
| 2009/0030524 A1 | 1/2009 | Schroeder et al. |
| 2009/0105364 A1 | 4/2009 | Merrill et al. |
| 2009/0118390 A1 | 5/2009 | Abt et al. |
| 2009/0192610 A1 | 7/2009 | Case et al. |
| 2009/0265001 A1 | 10/2009 | Muratoglu et al. |
| 2009/0281624 A1 | 11/2009 | Conteduca et al. |
| 2010/0003591 A1 | 1/2010 | Takita |
| 2010/0029858 A1 | 2/2010 | Rufner et al. |
| 2010/0082101 A1 | 4/2010 | Muratoglu et al. |
| 2010/0137481 A1 | 6/2010 | Shen et al. |
| 2011/0028600 A1 | 2/2011 | Rufner et al. |
| 2011/0306698 A1 | 12/2011 | Pletcher |
| 2012/0157591 A1 | 6/2012 | Rufner et al. |

FOREIGN PATENT DOCUMENTS

| | | |
|---|---|---|
| CA | 2619937 A1 | 3/2007 |
| CA | 2669386 A1 | 8/2008 |
| CS | 221403 | 9/1982 |
| CS | 221403 | 4/1983 |
| CZ | 221405 B1 | 2/1986 |
| EP | 0560279 | 9/1993 |
| EP | 0727195 A2 | 8/1996 |
| EP | 0995449 A1 | 4/2000 |
| EP | 0560279 B1 | 6/2000 |
| EP | 0727195 B1 | 8/2002 |
| EP | 1421918 A1 | 5/2004 |
| EP | 1647242 A1 | 4/2006 |
| EP | 1421918 B1 | 4/2008 |
| EP | 1647242 B1 | 5/2008 |
| EP | 1924614 A2 | 5/2008 |
| EP | 2046577 A1 | 4/2009 |
| EP | 2083981 A1 | 5/2009 |
| EP | 2150285 B1 | 2/2012 |
| JP | 7255832 A | 10/1995 |
| JP | 2004503300 A | 2/2004 |
| JP | 2004167256 A | 6/2004 |

(56) References Cited

FOREIGN PATENT DOCUMENTS

| | | |
|---|---|---|
| JP | 2009504897 A | 5/2009 |
| JP | 2012143575 A | 8/2012 |
| KR | 20090035724 A | 4/2009 |
| WO | WO-8900755 A1 | 1/1989 |
| WO | WO-9801085 A1 | 1/1998 |
| WO | WO-9814223 A1 | 4/1998 |
| WO | WO-0049079 A1 | 8/2000 |
| WO | WO/01/05337 | 1/2001 |
| WO | WO/01/80778 | 11/2001 |
| WO | WO-0195952 A1 | 12/2001 |
| WO | WO/03/049930 | 6/2003 |
| WO | WO/2004/024204 | 3/2004 |
| WO | WO/2004/064618 | 8/2004 |
| WO | WO-2004064618 A3 | 8/2004 |
| WO | WO/2004/101009 | 11/2004 |
| WO | WO-2006041969 A1 | 4/2006 |
| WO | WO2007/019874 A1 | 2/2007 |
| WO | WO-2007024684 A2 | 3/2007 |
| WO | WO/2007/056561 | 5/2007 |
| WO | WO2007/121167 A1 | 10/2007 |
| WO | WO-2008016174 A1 | 2/2008 |
| WO | WO-2008052574 A1 | 5/2008 |
| WO | WO/2008/092047 | 7/2008 |
| WO | WO/2008/101073 | 8/2008 |
| WO | WO/2008/101134 | 8/2008 |
| WO | WO/2008/113388 | 9/2008 |
| WO | WO-2008124825 A1 | 9/2008 |
| WO | WO2008/124825 A2 | 10/2008 |
| WO | WO/2009/032909 | 3/2009 |
| WO | WO/2009/045658 | 4/2009 |
| WO | WO-2009083981 A1 | 5/2009 |
| WO | WO-2009097412 A2 | 8/2009 |
| WO | WO-2009032909 A3 | 12/2009 |
| WO | WO 2010/129514 | 11/2010 |
| WO | WO-2010129514 A3 | 11/2010 |

OTHER PUBLICATIONS

Oral, Ebru, alpha-Tocopherol-doped irradiated UHMWPE for high fatigue resistance and low wear, Dec. 19, 2003, Biomaterials 25 (2004), 5515-5522.*

International Search Report for PCT/EP2009/008250 dated Jan. 21, 2010.

Extended EP Search Report and Written Opinion for EP Application No. 10 01 2579 dated Dec. 9, 2010.

Extended EP Search Report and Written Opinion for EP Application No. 10 01 2589 dated Dec. 9, 2010.

The Written Opinion and International Search Report mailed Mar. 25, 2010 in related International Application No. PCT/US2009/032412.

"New Joint Replacement Material Developed at MGH put to first Clinic Use" news release from Massachusetts General Hospital, dated Jul. 23, 2007, accessed May 13, 2008.

"Joint Replacement Material Developed at the MGH" from MA General Hosp.MGH Hotline On-line publication dated Aug. 10, 2007.

E-Poly HXLPE Brochure from BioMet Orthopedics, dated 2007.

Wannomae, et al., "Vitamin E Stabilized, Irradiated UHMWPE for Cruciate Retaining Knee Components",. 53rd Annual Meeting of Orthopaedic Research Society,. Feb. 11-14, 2007 Poster No. 1783.

Kurtz, et al., "Trace Concentrations of Vitamin E Protect Radiation Crosslinked UHMWPE from Oxidative Degration", 53rd Annual Meeting of the Orthopaedic Research Society. Feb. 11-14, 2007, Paper No. 0020.

Bragdon, et al., "A New Pin-onDisk Wear Testing Method for Simulating Wear of Polyethylene on Cobalt-Chrome Alloy in Total Hip Arthroplasty", Journal of Arthroplasty, vol. 16 No. 5, 2001 pp. 658-665.

Oral, et al., "Blending a-Tocopherol with UHMWPE Powder for Oxidation Resistance", 50th Annual Meeting of Orthopaedic Research Society, Poster No. 1485.

Written Opinion & Search Report for PCT/US/2008/059909 dated Sep. 14, 2009.

Written Opinion and Search Report for PCT/EP2005/008967 dated Jun. 21, 2006.

Oral, et al., "x-Tocopherol-doped irradiated UHMWPE for high fatigue resistance and low wear", Biomaterials, vol. 25, 2004, pp. 5515-5522.

Oral, et al., "Characterization of irradiated blends of X-tocopherol and UHMWPE", Biomaterials, vol. 26, 2005, pp. 6657-6663.

Parth, et al "Studies on the effect of electron beam radiation on the molecular structure of ultra-high molecular eight polyethylene under the influence of x-tocopherol w/ respect to its application in medical implants", Jrnl of Materials Science,vol. 13, 2002 pp. 917.

Tomita, et al., "Prevention of Fatigue Cracks in Ultrahigh Molecular Weight Polyethylene Joint Components by the Addition of Vitamin E", Applied Biomaterials, vol. 48, 1999, pp. 474-478.

Shibata, et al., "The anti-oxidative properties of x-tocopherol in y-irradiated UHMWPE with respect to fatigue and oxidation resistance", Biomaterials, vol. 26, 2005, pp. 5755-5762.

U.S. Patent Application filed Jun. 10, 2010 assigend U.S. Appl. No. 12/813,401.

U.S. Patent Application filed Jul. 30, 2010 assigned U.S. Appl. No. 12/847,741.

"U.S. Appl. No. 11/465,743, Advisory Action mailed Jul. 16, 2008", 5 pgs.

"U.S. Appl. No. 11/465,743, Advisory Action mailed Aug. 6, 2008", 6 pgs.

"U.S. Appl. No. 11/465,743, Advisory Action mailed Aug. 24, 2009", 6 pgs.

"U.S. Appl. No. 11/465,743, Amended Appeal Brief filed Mar. 10, 2010", 42 pgs.

"U.S. Appl. No. 11/465,743, Amended Appeal Brief filed Dec. 15, 2009", 41 pgs.

"U.S. Appl. No. 11/465,743, Appeal Brief filed Nov. 15, 2009", 41 pgs.

"U.S. Appl. No. 11/465,743, Examiner Interview Summary mailed Apr. 29, 2009", 4 pgs.

"U.S. Appl. No. 11/465,743, Examiner Interview Summary mailed Sep. 23, 2010", 2 pgs.

"U.S. Appl. No. 11/465,743, Examiner Interview Summary mailed Sep. 29, 2010", 2 pgs.

"U.S. Appl. No. 11/465,743, Examiner Interview Summary mailed Oct. 31, 2008", 3 pgs.

"U.S. Appl. No. 11/465,743, Final Office Action mailed May 1, 2008", 9 pgs.

"U.S. Appl. No. 11/465,743, Final Office Action mailed Jun. 16, 2009 ", 11 pgs.

"U.S. Appl. No. 11/465,743, Non Final Office Action mailed Sep. 28, 2007", 7 pgs.

"U.S. Appl. No. 11/465,743, Non Final Office Action mailed Dec. 15, 2008", 12 pgs.

"U.S. Appl. No. 11/465,743, Notice of Allowance mailed May 26, 2010", 6 pgs.

"U.S. Appl. No. 11/465,743, Notice of Allowance mailed Sep. 3, 2010", 7 pgs.

"U.S. Appl. No. 11/465,743, Response filed Jan. 17, 2008 to Non Final Office Action mailed Sep. 28, 2007", 13 pgs.

"U.S. Appl. No. 11/465,743, Response filed Mar. 16, 2009 to Non Final Office Action mailed Dec. 15, 2008", 11 pgs.

"U.S. Appl. No. 11/465,743, Response filed Jul. 1, 2008 to Final Office Action mailed May 1, 2008", 8 pgs.

"U.S. Appl. No. 11/465,743, Response filed Jul. 22, 2008 to Advisory Action mailed Jul. 16, 2008", 6 pgs.

"U.S. Appl. No. 11/465,743, Response filed Jul. 29, 2009 to Final Office Action mailed Jun. 16, 2009", 15 pgs.

"U.S. Appl. No. 11/465,743, Response filed Oct. 31, 2008 to Advisory Action mailed Aug. 6, 2008", 15 pgs.

"U.S. Appl. No. 11/465,743, Supplemental Notice of Allowability mailed Jul. 14, 2010", 2 pgs.

"U.S. Appl. No. 11/465,743, Supplemental Notice of Allowability mailed Sep. 29, 2010", 4 pgs.

"U.S. Appl. No. 11/465,743, Supplemental Response filed Apr. 20, 2009 to Non Final Office Action mailed Dec. 15, 2008", 10 pgs.

(56) References Cited

OTHER PUBLICATIONS

"U.S. Appl. No. 12/100,894, Examiner Interview Summary mailed Dec. 2, 2009", 3 pgs.
"U.S. Appl. No. 12/100,894, Non Final Office Action mailed Apr. 14, 2009", 16 pgs.
"U.S. Appl. No. 12/100,894, Response filed Mar. 31, 2009 to Restriction Requirement mailed Mar. 2, 2009", 2 pgs.
"U.S. Appl. No. 12/100,894, Restriction Requirement mailed Mar. 2, 2009", 7 pgs.
"U.S. Appl. No. 12/262,531, Final Office Action mailed Jan. 14, 2010", 11 pgs.
"U.S. Appl. No. 12/262,531, Non Final Office Action mailed Jun. 17, 2010", 16 pgs.
"U.S. Appl. No. 12/262,531, Non Final Office Action mailed Jun. 25, 2009", 7 pgs.
"U.S. Appl. No. 12/262,531, Notice of Allowance mailed Oct. 28, 2010", 6 pgs.
"U.S. Appl. No. 12/262,531, Preliminary Amendment filed Oct. 31, 2008", 6 pgs.
"U.S. Appl. No. 12/262,531, Response filed Apr. 28, 2010 to Final Office Action mailed Jan. 14, 2010", 15 pgs.
"U.S. Appl. No. 12/262,531, Response filed Sep. 17, 2010 to Non Final Office Action mailed Jun. 17, 2010", 4 pgs.
"U.S. Appl. No. 12/262,531, Response filed Sep. 23, 2009 to Non Final Office Action mailed Jun. 25, 2009", 10 pgs.
"U.S. Appl. No. 12/262,531, Supplemental Notice of Allowability mailed Nov. 23, 2010", 4 pgs.
"U.S. Appl. No. 12/464,235, Final Office Action mailed Aug. 19, 2010", 11 pgs.
"U.S. Appl. No. 12/464,235, Non Final Office Action mailed Mar. 2, 2010", 7 pgs.
"U.S. Appl. No. 12/464,235, Non Final Office Action mailed Dec. 23, 2010", 10 pgs.
"U.S. Appl. No. 12/579,094, Examiner Interview Summary mailed Jan. 6, 2012", 1 pg.
"U.S. Appl. No. 12/579,094, Final Office Action mailed Oct. 13, 2010", 14 pgs.
"U.S. Appl. No. 12/579,094, Non Final Office Action mailed May 18, 2010", 19 pgs.
"U.S. Appl. No. 12/579,094, Notice of Allowance mailed Jan. 6, 2012", 8 pgs.
"U.S. Appl. No. 12/579,094, Preliminary Amendment filed Oct. 14, 2009", 11 pgs.
"U.S. Appl. No. 12/579,094, Response filed Jan. 27, 2012 to Notice of Allowance mailed Jan. 6, 2012", 5 pgs.
"U..S. Appl. No. 12/579,094, Response filed Jan. 31, 2012 to 312 Amendment mailed Jan. 27, 2012", 2 pgs.
"U.S. Appl. No. 12/579,094, Response filed Apr. 7, 2010 to Restriction Requirement mailed Mar. 9, 2010", 9 pgs.
"U.S. Appl. No. 12/579,094, Response filed Apr. 12, 2011 to Final Office Action mailed Oct. 13, 2010", 45 pgs.
"U.S. Appl. No. 12/579,094, Response filed Sep. 20, 2010 to Non Final Office Action mailed May 18, 2010", 30 pgs.
"U.S. Appl. No. 12/579,094, Restriction Requirement mailed Mar. 9, 2010", 7 pgs.
"U.S. Appl. No. 12/847,741, Application filed Jul. 30, 2010", 72 pgs.
"U.S. Appl. No. 12/847,741, Final Office Action mailed Jun. 27, 2012", 7 pgs.
"U.S. Appl. No. 12/847,741, Non Final Office Action mailed Feb. 24, 2012", 11 pgs.
"U.S. Appl. No. 12/847,741, Preliminary Amendment filed Oct. 18, 2010", 5 pgs.
"U.S. Appl. No. 12/847,741, Response filed May 23, 2012 to Non Final Office Action mailed Feb. 24, 2012", 10 pgs.
"U.S. Appl. No. 12/847,741, Response filed Sep. 26, 2012 to Final Office Action mailed Jun. 27, 2012", 14 pgs.
"U.S. Appl. No. 12/847,741, Second Preliminary Amendment filed Feb. 21, 2012", 4 pgs.
"U.S. Appl. No. 12/942,703, Applicant's Summary of Examiner Interview filed Feb. 17, 2012", 3 pgs.
"U.S. Appl. No. 12/942,703, Application filed Nov. 9, 2010", 20 pgs.
"U.S. Appl. No. 12/942,703, Final Office Action mailed Mar. 16, 2012", 14 pgs.
"U.S. Appl. No. 12/942,703, Non Final Office Action mailed Aug. 2, 2011", 17 pgs.
"U.S. Appl. No. 12/942,703, Non Final Office Action mailed Aug. 23, 2012", 14 pgs.
"U.S. Appl. No. 12/942,703, Response filed Jan. 3, 2012 to Non Final Office Action mailed Aug. 2, 2011", 34 pgs.
"U.S. Appl. No. 12/942,703, Response filed Jul. 16, 2012 to Final Office Action mailed Mar. 16, 2012", 14 pgs.
"U.S. Appl. No. 12/943,160, Applicant's Summary of Examiner Interview filed Feb. 17, 2012", 2 pgs.
"U.S. Appl. No. 12/943,160, filed Nov. 10, 2010", 33 pgs.
"U.S. Appl. No. 12/943,160, Examiner Interview Summary mailed Feb. 3, 2012", 2 pgs.
"U.S. Appl. No. 12/943,160, Final Office Action mailed Sep. 28, 2012", 14 pgs.
"U.S. Appl. No. 12/943,160, Non Final Office Action mailed Mar. 16, 2012", 11 pgs.
"U.S. Appl. No. 12/943,160, Non Final Office Action mailed Aug. 12, 2011", 8 pgs.
"U.S. Appl. No. 12/943,160, Response filed Jan. 11, 2012 to Non Final Office Action mailed Aug. 12, 2011", 13 pgs.
"U.S. Appl. No. 12/943,160, Response filed Jul. 16, 2012 to Non Final Office Action mailed Mar. 16, 2012", 13 pgs.
"U.S. Appl. No. 12/967,581, Application filed Dec. 14, 2010", 51 pgs.
"U.S. Appl. No. 12/967,581, Examiner Interview Summary mailed Jan. 23, 2012", 2 pgs.
"U.S. Appl. No. 12/967,581, Notice of Allowance mailed Feb. 7, 2012", 10 pgs.
"U.S. Appl. No. 12/967,581, Preliminary Amendment filed Jan. 19, 2012", 7 pgs.
"U.S. Appl. No. 12/967,581, Preliminary Amendment filed Jan. 27, 2012", 4 pgs.
"U.S. Appl. No. 12/967,581, Preliminary Amendment filed Feb. 18, 2011", 5 pgs.
"U.S. Appl. No. 12/967,581, Preliminary Amendment filed Dec. 14, 2010", 7 pgs.
"U.S. Appl. No. 13/403,040, Non Final Office Action mailed Jul. 16, 2012", 14 pgs.
"U.S. Appl. No. 13/403,040, Response filed Oct. 16, 2012 to Non Final Office Action mailed Jul. 16, 2012", 15 pgs.
"Australian Application Serial No. 2008236996, Office Action mailed Jan. 19, 2012", 3 pgs.
"Biomet Orthopedics", Brochure E-PolY HSLPE (EXH2O), (2007), 23 pgs.
"Canadian Application No. 2,619,502, Office Action mailed Nov. 4, 2011", 5 pgs.
"E-Poly HXLPE Brochure from BioMet Orthopedics", (2007), 23 pgs.
"European Application Serial No. 05777319.4, Office Action mailed Jun. 10, 2009", 4 pgs.
"European Application Serial No. 05777319.4, Office Action mailed Jul. 28, 2010", 1 pg.
"European Application Serial No. 05777319.4, Office Action mailed Sep. 15, 2008", 1 pg.
"European Application Serial No. 05777319.4, Response filed Jan. 20, 2009 to Office Action mailed Sep. 15, 2008", 7 pgs.
"European Application Serial No. 05777319.4, Response filed Oct. 8, 2009 to Office Action mailed Jun. 10, 2009", 9 pgs.
"European Application Serial No. 08745507.7, Office Action mailed Jan. 12, 2010", 2 pgs.
"European Application Serial No. 08745507.7, Office Action mailed May 10, 2010", 3 pgs.
"European Application Serial No. 08745507.7, Office Action mailed Jul. 20, 2011", 4 pgs.
"European Application Serial No. 08745507.7, Response filed Feb. 16, 2010 to Office Action mailed Jan. 12, 2010", 5 pgs.
"European Application Serial No. 08745507.7, Response filed Sep. 20, 2010 to Office Action mailed May 10, 2010", 3 pgs.

(56) References Cited

OTHER PUBLICATIONS

"European Application Serial No. 08745507.7, Response filed Nov. 21, 2011 to Office Action mailed Jul. 21, 2011", 3 pgs.
"European Application Serial No. 09013154.1, European Search Report mailed Feb. 23, 2010", 6 pgs.
"European Application Serial No. 09013154.1, Office Action mailed Sep. 14, 2011", 4 pgs.
"European Application Serial No. 09013154.1, Office Action mailed Oct. 21, 2010", 1 pg.
"European Application Serial No. 09013154.1, Response filed Jan. 26, 2012 to Office Action mailed Sep. 14, 2011", 7 pgs.
"European Application Serial No. 09013154.1, Response filed Mar. 21, 2011 to Office Action mailed Oct. 21, 2010", 22 pgs.
"European Application Serial No. 10012579.8, European Search Report mailed Feb. 23, 2010", 3 pgs.
"European Application Serial No. 10012579.8, Office Action mailed Jan. 31, 2011", 2 pgs.
"European Application Serial No. 10012579.8, Office Action mailed Apr. 23, 2012", 4 pgs.
"European Application Serial No. 10012579.8, Office Action mailed Sep. 18, 2012", 4 pgs.
"European Application Serial No. 10012579.8, Response filed Jan. 26, 2012 to Office Action mailed Sep. 14, 2011", 11 pgs.
"European Application Serial No. 10012579.8, Response filed Jul. 3, 2012 to Office Action mailed Apr. 23, 2012", 15 pgs.
"European Application Serial No. 10012579.8, Response filed Jul. 26, 2011 to Office Action mailed Jan. 31, 2011", 29 pgs.
"European Application Serial No. 10012589.7, European Search Report mailed Feb. 23, 2010", 6 pgs.
"European Application Serial No. 10012589.7, European Search Report mailed Dec. 9, 2010", 7 pgs.
"European Application Serial No. 10012589.7, Office Action mailed Jan. 31, 2011", 2 pgs.
"European Application Serial No. 10012589.7, Office Action mailed Feb. 3, 2010", 1 pg.
"European Application Serial No. 10012589.7, Office Action mailed Mar. 27, 2012", 4 pgs.
"European Application Serial No. 10012589.7, Office Action mailed Dec. 16, 2010", 1 pg.
"European Application Serial No. 10012589.7, Response filed Jan. 13, 2012", 8 pgs.
"European Application Serial No. 10012589.7, Response filed Feb. 13, 2012 to Office Action mailed Dec. 2, 2011", 7 pgs.
"European Application Serial No. 10012589.7, Response filed Jul. 26, 2011 to Office Action mailed Jan. 31, 2011", 9 pgs.
"European Application Serial No. 12154330.0, European Search Report mailed Jul. 18, 2012", 15 pgs.
"International Application Serial No. PCT/EP2005/008967, International Preliminary Report on Patentability mailed Feb. 20, 2008", 7 pgs.
"International Application Serial No. PCT/EP2005/008967, International Search Report mailed Jun. 21, 2006", 3 pgs.
"International Application Serial No. PCT/EP2005/008967, Written Opinion mailed Jun. 21, 2006", 6 pgs.
"International Application Serial No. PCT/EP2009/008250, International Search Report mailed Jan. 21, 2010", 3 pgs.
"International Application Serial No. PCT/EP2009/008250, Written Opinion mailed Jan. 21, 2010", 5 pgs.
"International Application Serial No. PCT/US2008/059909, International Preliminary Report on Patentability mailed Nov. 10, 2009", 8 pgs.
"International Application Serial No. PCT/US2008/086817, International Search Report mailed Sep. 14, 2009", 3 pgs.
"International Application Serial No. PCT/US2008/086817, Written Opinion mailed Sep. 14, 2009", 7 pgs.
"International Application Serial No. PCT/US2009/032412, International Search Report mailed Mar. 25, 2010", 4 pgs.
"International Application Serial No. PCT/US2009/032412, Written Opinion mailed Mar. 25, 2010", 5 pgs.
"Japanese Application Serial No. 2008-526378, Office Action mailed Jun. 19, 2012", (w/ English translation), 6 pgs.
"Japanese Application Serial No. 2008-526378, Office Action mailed Sep. 6, 2011", (w/ English Translation), 11 pgs.
"Japanese Application Serial No. 2008-526378, Response filed Mar. 6, 2012 to Office Action mailed Sep. 6, 2011", (w/ English translation of claims), 10 pgs.
"Joint replacement material developed at the Massachusetts General Hospital", from MA General Hosp. MGH Hotline On-line publication, (Aug. 10, 2007), 1 pg.
"New joint replacement material developed at Massachusetts General Hospital and put to first clinic use", news release from Massachusetts General Hospital, accessed May 13, 2008, (Nov. 15, 2010), 2 pgs.
Greer, K. W., et al., "The Effects of Raw Material, Irradiation Dose, and Irradiation Source on Crosslinking of UHMWPE", Journal of ASTM International, vol. 1, No. 1, (Jan. 2004), pp. 1-11.
Lewis, Nathan S, et al., "Application Serial No. PCT/US2009/032,412, Written Opinion and Search Report dated Mar. 25, 2010", 2 pgs.
Oral, E, et al., "Crosslinked Vitamin E Blended UHMWPE with Improved Grafting and Wear Resistance", ORS Annual Meeting, Poster No. 1181, (2011), 1 pg.
Oral, E, et al., "Trace amounts of grafted vitamin E protect UHMWPE against squalene-initiated oxidation", ORS Annual Meeting, Poster No. 1295, (2011), 1 pg.
Pletcher, Dirk, et al., "Polymers Compositions Including an Antioxidant", U.S. Appl. No. 12/813,401, filed Jun. 10, 2010, (Dec. 15, 2011), 52 pgs.
Rowell, S, et al., "Detection of Vitamin E in Irradiated UHMWPE by UV-Visible Spectroscopy", ORS 2011 Annual Meeting, Poster No. 1186, (2011), 1 pg.
Rufner, Alicia, et al., "An Antioxidant Stabilized Crosslinked Ultra-High Molecular Weight Polyethylene for Medical Device Applications", U.S. Appl. No. 12/847,741, Application Filed Jul. 30, 2010, 69 pgs.
Wolf, C, et al., "Radiation Grafting of Vitamin E to Ultra High Molecular Weight Polyethylene", ORS Annual Meeting, Poster No. 1178, (2011), 1 pg.
"Australian Application Serial No. 2009209158, First Examiners Report mailed May 2, 2013", 3 pgs.
"European Application Serial No. 09705611.3, Examination Notification Art. 94(3) mailed May 13, 2013", 3 pgs.
"International Application Serial No. PCT/US2009/032412, International Preliminary Report on Patentability mailed Sep. 30, 2010", 14 pgs.
"Japanese Application Serial No. 2010-545156, Office Action mailed May 8, 2013", 9 pgs.
US 7,253,214, 08/2007, McKellop (withdrawn)

* cited by examiner

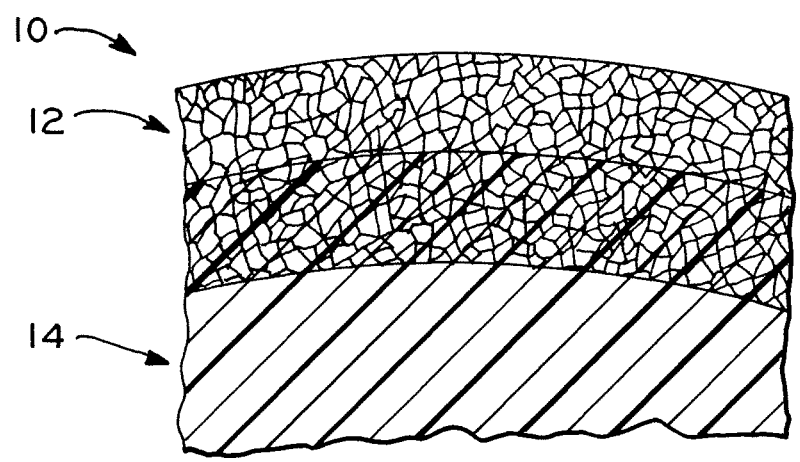
FIG_2A
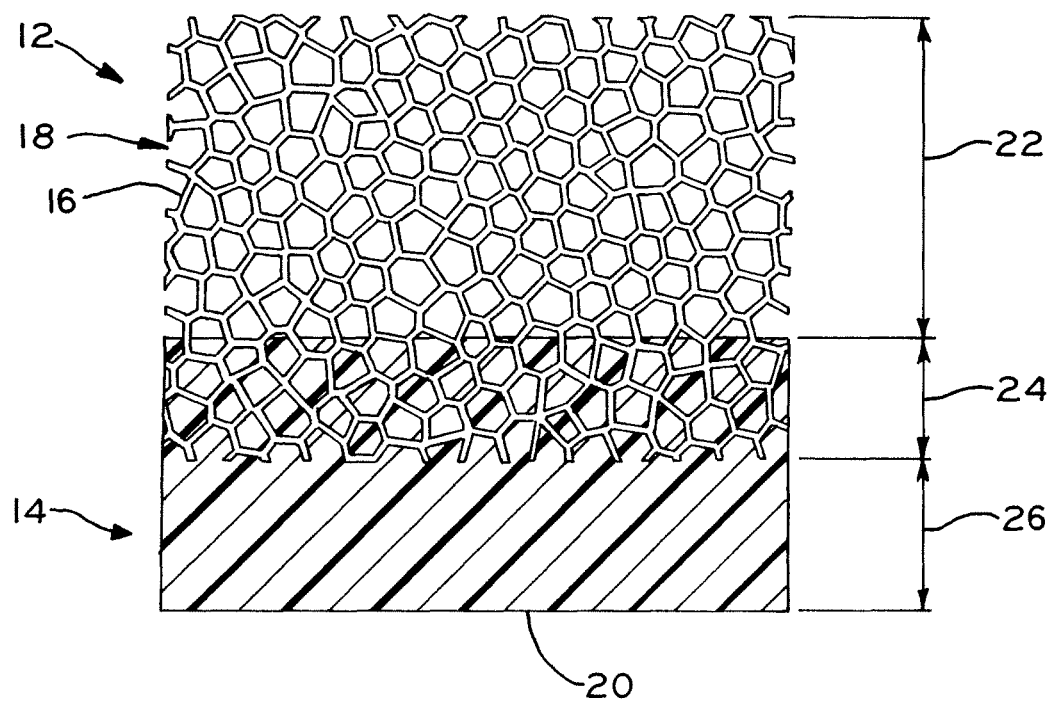
FIG_2B

COMPARISON MATERIAL PROPERTIES
CONVENTIONAL UHMWPE VS VITAMIN E TREATED UHMEPE

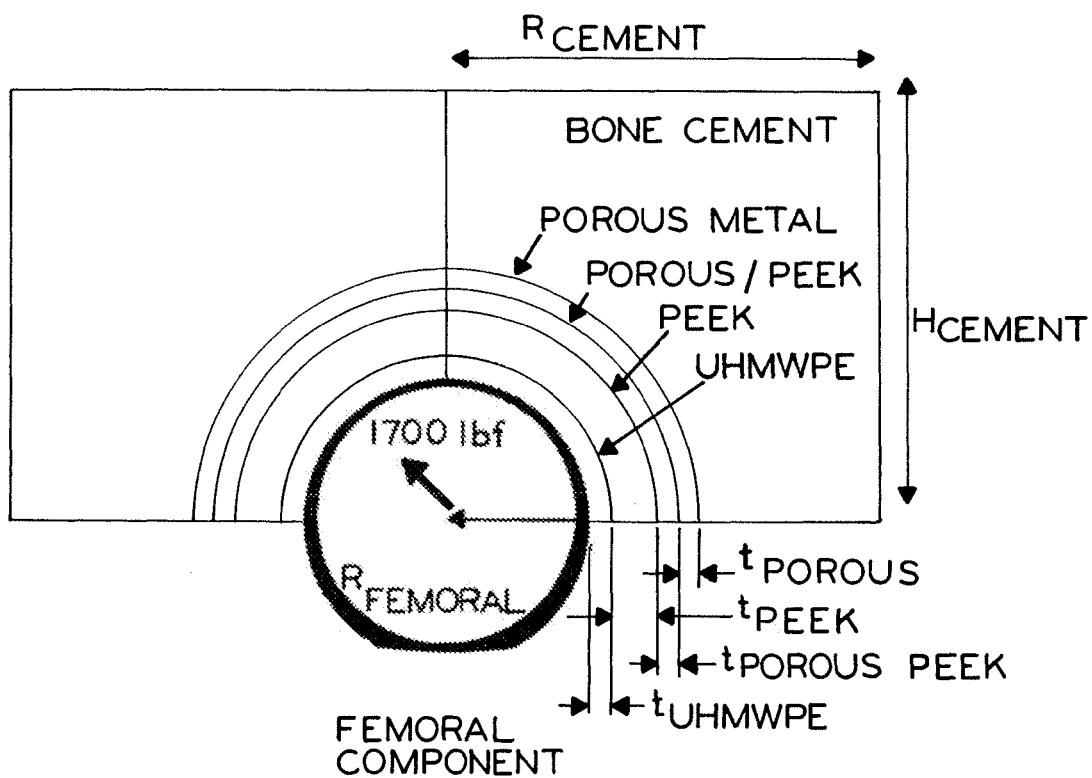
FIG_6
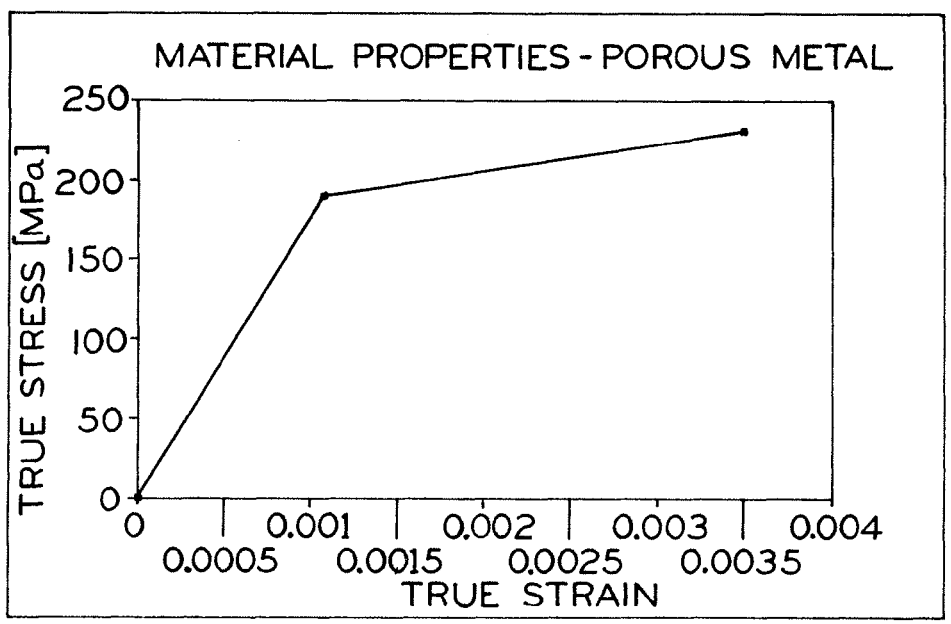
FIG_7

ORTHOPEDIC COMPONENT OF LOW STIFFNESS

CROSS-REFERENCE TO RELATED APPLICATIONS

This application claims the benefit under Title 35 U.S.C. §119(e) of U.S. Provisional Patent Application Ser. No. 61/104,870, entitled "ORTHOPEDIC COMPONENT OF LOW STIFFNESS", filed on Oct. 13, 2008, U.S. Provisional Patent Application Ser. No. 61/038,281, entitled "ORTHOPEDIC COMPONENT OF LOW STIFFNESS", filed on Mar. 20, 2008, U.S. Provisional Patent Application Ser. No. 61/024,737, entitled "ACETABULAR COMPONENT", filed on Jan. 30, 2008, and U.S. Provisional Patent Application Ser. No. 61/024,778, entitled "ACETABULAR COMPONENT", filed on Jan. 30, 2008, the entire disclosures of which are hereby expressly incorporated by reference herein.

BACKGROUND

1. Field of the Invention

The present invention relates to orthopedics, and, particularly, to orthopedic implants.

2. Description of the Related Art

During orthopedic surgery, such as a total hip arthroplasty, orthopedic prostheses are implanted into a patient's body. For example, a femoral stem may be implanted into the intramedullary canal of the patient's femur. After the stem is inserted into the intramedullary canal at a desired depth and orientation, a femoral head may be attached to the proximal end of the stem. The femoral head fits into a substantially hemispherically shaped socket of an acetabular prosthesis and provides a surface for articulation between the femoral head and the acetabular prosthesis.

In certain embodiments, acetabular prostheses comprise two separate components, an acetabular backing component and an acetabular articulating component, which are often referred to as a shell and liner, respectively. The backing component is generally hemispherically shaped and is affixed and embedded into an acetabulum of a patient. Similarly, the liner has a hemispherical shape configured to mate with an internal cavity of the backing component. The liner further includes a socket to mate with a femoral head. The acetabular backing components are typically formed of solid metal, such as titanium or a titanium alloy, or from stainless steel. In contrast, the acetabular articulating components may be formed from an ultra-high molecular weight polyethylene polymer material ("UHMWPE"). These types of acetabular cups are often referred to in the art, and sometimes herein, as "metal backed" components.

Metal backed orthopedic components generally experience contact stresses during normal joint articulation. For example, in conventional metal backed acetabular components, previous studies have shown that polymer thickness and conformity between the femoral head and the polyethylene liner play a significant role in the level of contact stress experienced. For highly conforming acetabular component designs, the contact stress in the polymer liner is very sensitive to the polymer thickness when the polymer thickness is small. Specifically, it has been demonstrated that when the polymer thickness is less than 4-6 mm, the contact stress generally increases rapidly as the thickness decreases. Therefore, a minimum polymer thickness of 4-6 mm has been maintained for metal backed acetabular components in an attempt to lessen the contact stress. Further, having a 4 mm minimum thickness of the polyethylene liner in an acetabular component has been widely accepted as an industry design rule and has been traditionally relied upon in the manufacture of acetabular components.

Stress shielding is a phenomenon that can potentially occur with metal backed orthopedic components and can occur when a portion of the stress normally exerted on a patient's bone is instead borne by the orthopedic component, such as an acetabular cup. As result, the bone may begin to undergo atrophy and decalcification resulting in a weaker bone structure. In severe stress shielding, the bone may be resorbed by the body, decreasing the amount of bone stock at the fracture site.

SUMMARY

The present invention, in one exemplary embodiment, provides an orthopedic component having multiple layers that are selected to provide an overall modulus that is substantially lower than the modulus of known orthopedic components to more closely approximate the modulus of the bone into which the orthopedic component is implanted. In one exemplary embodiment, the orthopedic component is an acetabular shell. For example, the acetabular shell may include an outer layer configured for securement to the natural acetabulum of a patient and an inner layer configured to receive an acetabular liner. The head of a femoral prosthesis articulates against the acetabular liner to replicate the function of a natural hip joint. Alternatively, the inner layer of the acetabular shell may act as an integral acetabular liner against which the head of the femoral prosthesis articulates.

In one exemplary embodiment, the outer layer of the acetabular shell is formed from a metal and the inner layer is formed from a biocompatible polymer. For example, the outer layer may be formed from a porous metal and the inner layer from a polyaryletherketone ("PAEK"), such as polyetheretherketone ("PEEK"), or from a UHMWPE, such as an antioxidant stabilized UHMWPE. To form an acetabular shell according to the present invention, the outer layer is formed as a cup-shaped body using traditional techniques. Once formed, the biocompatible polymer, such as PEEK or UHMWPE, is secured to the outer layer to form an inner layer, resulting in a substantially completed acetabular shell. In exemplary embodiments, the polymer is attached to the outer layer by injection or compression molding. In one exemplary embodiment, the orthopedic component is complete after attachment of the outer and inner layers, e.g., after injection or compression molding, and requires no further machining or modification prior to implantation. In another exemplary embodiment, the orthopedic component may be further machined after attachment of the outer and inner layers to provide the final details, dimensions, and/or features that are desired.

Attaching a biocompatible polymer to a porous material to form an orthopedic implant allows the polymer to be received within the pores of the material. When the polymer hardens, the interaction of the two materials provides a firm securement between the porous layer and the polymer layer to form the orthopedic component. Additionally, when the biocompatible polymer is compression or injection molded, for example, to the porous material, a locking feature, such a groove configured to receive a corresponding snap ring, for example, may be integrally formed in and/or on the polymer. By integrally forming a locking feature into or on the orthopedic component, the machining steps necessary to finish the orthopedic component may be reduced and/or entirely eliminated.

Advantageously, by manufacturing an orthopedic component in accordance with embodiments of the present invention, the orthopedic component has a stiffness which is lower than the stiffness of other orthopedic components. As a result, the present invention lessens the effects of stress shielding on the natural bone stock, reducing the potential for osteolysis and bone resorption.

Additionally, the present invention provides a surgeon with the ability to drill bone screw receiving apertures into the orthopedic component at the most advantageous locations. Thus, when implanting an acetabular shell, for example, the surgeon may identify the areas of the acetabulum having the greatest bone stock and then drill apertures through the acetabular shell which are aligned to utilize this bone stock. As a result, each orthopedic component can be custom fit to the individual patient to facilitate the optimal retention of the orthopedic component by the natural bone stock. Additionally, allowing a surgeon to customize the location of the bone screw receiving apertures reduces inventory and machining costs by eliminating the need to manufacture and stock orthopedic components with various bone screw receiving aperture configurations. Further, the method of manufacture of the present invention may be used to create a smooth surface on the polymer of the orthopedic component against which another orthopedic component and/or natural bone stock may articulate. By creating a smooth surface on the polymer, the generation of wear debris may be lessened.

Further, by utilizing an antioxidant stabilized polymer, such as UHMWPE blended with vitamin E, the overall thickness of the polymer layer may be lessened. Thus, the polymer layer may have a thickness of less then 4 mm, for example, without demonstrating an unacceptable level of contact stress. This results in reduced material and manufacturing costs. Further, by utilizing an antioxidant stabilized polymer, long term oxidation of the polymer may be lessened, increasing the useful life of the orthopedic component.

In one form thereof, the present invention provides an orthopedic system including: a substantially hemispherical outer layer formed from a first porous material; and a substantially hemispherical inner layer formed from a polyaryletherketone, wherein the polyaryletherketone at least partially permeates the pores of the first porous material so that at least a portion of the polyaryletherketone interdigitates with pores of the first porous material, the first porous material and the polyaryletherketone cooperating to define an acetabular shell having an effective stiffness between 0.1 GPa and 15 GPa.

In another form thereof, the present invention provides an acetabular component configured for use in a hip replacement surgery, the acetabular component including: a porous layer configured to contact and interface with bone tissue when the acetabular component is implanted; an inner layer formed from an antioxidant stabilized, crosslinked ultrahigh molecular weight polyethylene and having a thickness of less than six millimeters, the inner layer configured to receive a femoral component; and an interdigitation layer defined by the distance over which the antioxidant stabilized, crosslinked ultrahigh molecular weight polyethylene of the inner layer infiltrates pores of the porous layer.

In yet another form thereof, the present invention provides a method of manufacturing an orthopedic component for implantation into a bone, the orthopedic implant having a bone contacting layer, an interdigitation layer, and an inner layer, the method comprising the steps of: determining the elastic modulus of the bone; selecting a thickness of at least one of the bone contacting layer, an interdigitation layer, and an inner layer based on the elastic modulus of the bone; and molding the inner layer to the bone contacting layer to form at least one of the bone contacting layer, an interdigitation layer, and an inner layer to have the selected thickness.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 2A is a fragmentary sectional view of a portion of the implant of FIG. 1;

FIG. 2B is an enlarged schematic representation of a portion of the implant of FIG. 2A;

FIG. 6 depicts a graphical illustration of an exemplary finite element model;

FIG. 7 depicts a graphical illustration of the stress/strain properties of porous metal;

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figure 1:
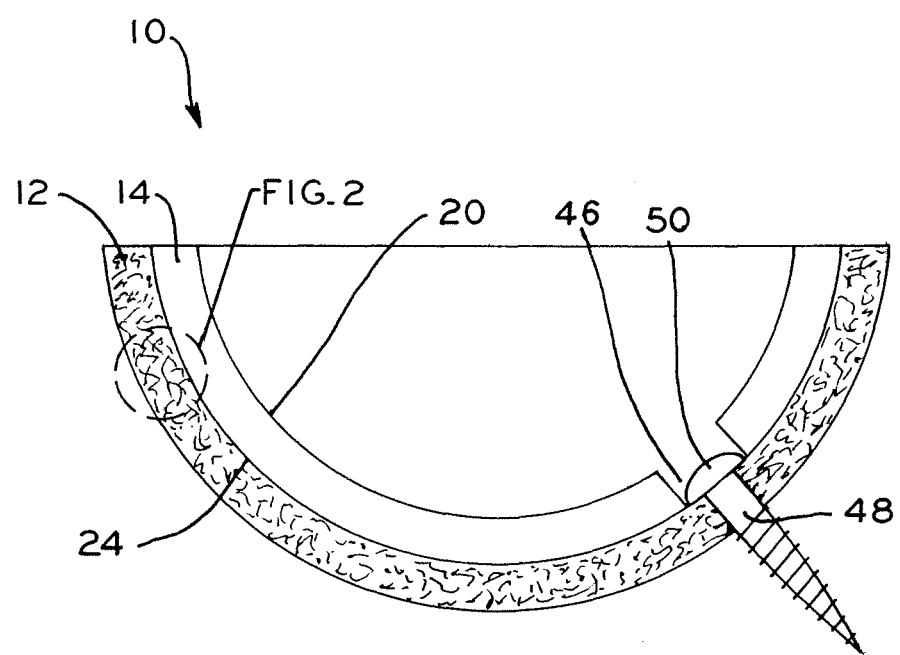
FIG. 1 is cross-sectional view of an exemplary orthopedic implant, depicted as an acetabular shell, made in accordance with an exemplary embodiment of the present invention.

As shown in FIG. 1, an orthopedic component is depicted as acetabular shell 10. While described and depicted herein with specific reference to an acetabular shell, the orthopedic component of the present invention may be any orthopedic component, such as a glenoid component for use in a shoulder prosthesis system. Acetabular shell 10 has a substantially hemispherical shape and includes first, outer bone-contacting layer 12 and second, inner layer 14 against which a corresponding femoral orthopedic component and/or natural femoral head articulate. In one exemplary embodiment, second, inner layer 14 provides a surface against which an additional acetabular liner (FIG. 3) may be seated. Additionally, acetabular prosthesis 10 may have any suitable shape known in the art, such as hemispherical, and is generally configured to mate with a femoral head assembly, as indicated above, such as the femoral head assembly disclosed in U.S. Pat. No. 7,306,629, entitled "FEMORAL HEAD ASSEMBLY WITH VARIABLE OFFSET", assigned to the assignee of the present invention, the entire disclosure of which is hereby expressly incorporated by reference herein. Similarly, prosthesis 10 may have a shape similar to that disclosed in U.S. Pat. No. 5,879,398, entitled "ACETABULAR CUP", assigned to the assignee of the present invention, the entire disclosure of which is hereby expressly incorporated by reference herein.

In one exemplary embodiment, acetabular shell 10 has a stiffness which is less than the stiffness of other, known acetabular shells. Specifically, acetabular shell 10 has an effective stiffness which is substantially less than the effective stiffness of known acetabular shells. As used herein, absent an indication to the contrary or use of a different term, "effective stiffness" refers to the overall stiffness or elastic modulus of the entire construct of an orthopedic component according to the experimental procedures set forth below in the Examples. As a result of the lower effective stiffness of the acetabular shell made in accordance with the present invention, the effect of stress shielding on the natural acetabulum is lessened. As indicated above, stress shielding is a phenomenon in which the rigidity of implanted orthopedic components limits the transfer of forces to natural bone stock that the bone stock would normally receive, such as during the loading of a joint. As a result, osteolysis may occur at the joint, which may result in bone resorption and weakening of the bone stock surrounding the implanted orthopedic components. Thus, due to the lower effective stiffness of acetabular shell 10, acetabular shell 10 allows for a greater amount of joint loading forces to be transferred to the natural bone stock.

In one exemplary embodiment, bone-contacting layer 12 is formed from a porous material, such as a porous metal. In one exemplary embodiment, bone-contacting layer 12 is formed using Trabecular Metal™ technology available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, issued Feb. 1, 1994, entitled "OPEN CELL TANTALUM STRUCTURES FOR CANCELLOUS BONE IMPLANTS AND CELL AND TISSUE RECEPTORS", and in Levine, B. R., et al., "Experimental and Clinical Performance of Porous Tantalum in Orthopedic Surgery", Biomaterials 27 (2006) 4671-4681, the entirely disclosures of which are hereby expressly incorporated by reference herein. In addition to tantalum, other metals such as niobium, or alloys of tantalum and niobium with one another or with other metals may also be used.

Generally, with reference to FIGS. 2A and 2B, the porous tantalum structure of bone-contacting layer 12 includes a large plurality of ligaments 16 defining open spaces, such as voids or channels 18, therebetween, with each ligament 16 generally including a carbon core covered by a thin film of metal such as tantalum, for example. The open spaces between ligaments 16 form a matrix of continuous channels having no dead ends, such that the growth of cancellous bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to anchor acetabular shell 10 in the surrounding bone of the pelvis.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone in growth and mineralization.

While described herein as being formed from Trabecular Metal™ technology, first, bone-contacting layer 12 may be formed from any biocompatible metal, such as Ti-6Al-4V, or a porous material, such as a fiber metal. Additionally, in another exemplary embodiment, a nonporous metal, such as titanium, is used to form bone-contacting layer 12 and the inner surface thereof may be formed to incorporate a porous surface. The porous surface allows for inner layer 14 to be received within the pores of bone-contacting layer 12.

As indicated above, inner layer 14 is formed from a biocompatible polymer. In one exemplary embodiment, inner layer 14 is formed from a PAEK, such as PEEK. In another exemplary embodiment, inner layer 14 is formed from UHMWPE. In other exemplary embodiments, the biocompatible polymer may be a polyolefin, polyester, polyimide, polyamide, polyacrylate, and/or other suitable polymers. By utilizing a porous metal, such as a metal manufactured using Trabecular Metal™ technology, and a biocompatible polymer, such as PEEK or UHMWPE, in combination, the elastic moduli of both materials forming acetabular shell 10 may be selected to be between the elastic moduli of cortical bone and trabecular bone.

Specifically, the elastic modulus of porous tantalum made in accordance with Trabecular Metal™ technology is approximately 3 GPa (gigapascal), the elastic modulus of PEEK is approximately 3.6 GPa, and the elastic modulus of UHMWPE ranges from 0.5 GPa to 2.0 GPa, depending on the specific UHMWPE used. Thus, various values within the range of 0.5 GPa and 2.0 GPa have been used for the elastic modulus of UHMWPE in the calculations throughout the present application and the Examples contained herein. The specific value for the elastic modulus of UHMWPE that is used in any particular calculation is identified where relevant. In addition, the elastic moduli of cortical bone and trabecular bone are 15 GPa and 0.1 GPa, respectively. In contrast, the elastic modulus of Cobalt-Chromium is 220 GPa and the elastic modulus of Ti-6Al-4V is 110 GPa. Thus, the substantially low elastic moduli of porous tantalum made in accordance with Trabecular Metal™ technology and PEEK and/or UHMWPE provide for the effective stiffness of acetabular shell 10 to be substantially lower than the effective stiffness of known acetabular shells. For example, the effective stiffness of acetabular shell 10 may be as low as 0.2, 0.3, 0.4, 0.5, 0.6, 0.7, 0.8, or 0.9 GPa or as high as 1.0, 1.1, 1.2, 1.3, 1.4, 1.5, 2.0, 2.5, 4.0, or 8.0 GPa. In one exemplary embodiment, the effective stiffness of acetabular shell 10 is between 0.3 GPa and 1.5 GPa.

When UHMWPE is used as the polymer for inner layer 14, in order to beneficially alter the material properties of UHMWPE and decrease its wear rate, the UHMWPE may be crosslinked. For example, UHMWPE may be subjected to electron beam or gamma irradiation, causing chain scissions of the individual polyethylene molecules as well as the breaking of C—H bonds to form free radicals on the polymer chains. The free radicals on adjacent polymer chains may then bond together to form crosslinked UHMWPE.

In another exemplary embodiment, inner layer 14 is formed from an antioxidant stabilized polymer, such as antioxidant stabilized UHMWPE. In one exemplary embodiment, UHMWPE powder is combined with an antioxidant to form an antioxidant stabilized UHMWPE. By forming inner layer 14 from an antioxidant stabilized polymer, some of the free radicals in the polymer are quenched, which reduces oxidation and, correspondingly, increases the useful life of the polymer. For example, the UHMWPE may include an antioxidant such as Vitamin C, lycopene, honey, and/or tocopherol, i.e., Vitamin E. Additionally, as any tocopherol may be used, such as d-α-tocopherol, d,l-α-tocopherol, or α-tocopherol acetate, unless otherwise specifically stated herein, the term "tocopherol" in its generic form refers to all tocopherols. Exemplary methods for combining UHMWPE with antioxidants are disclosed in co-pending U.S. patent application Ser. No. 12/100,894, entitled "AN ANTIOXIDANT STABILIZED CROSSLINKED ULTRA-HIGH MOLECULAR WEIGHT POLYETHYLENE FOR MEDICAL DEVICE APPLICATIONS", filed Apr. 10, 2008, assigned to the assignee of the present invention, the entire disclosure of which is hereby expressly incorporated by reference herein.

In combining UHMWPE and tocopherol to form an antioxidant stabilized UHMWPE, any mechanism and/or process achieving a substantially homogenous blend of the components may be utilized. In one exemplary embodiment, solvent blending is utilized. In solvent blending, tocopherol is mixed with a volatile solvent to lower the viscosity of the tocopherol and facilitate homogenous blending of the tocopherol with the UHMWPE. Once the tocopherol is mixed with the solvent, the tocopherol/solvent mixture may be combined with the UHMWPE, such as with a cone mixer. The solvent is then evaporated, leaving only the antioxidant stabilized UHMWPE. In another exemplary embodiment, tocopherol may be blended with UHMWPE by precision coating or atomization. For example, tocopherol may be precision coated onto the UHMWPE powder using a MP-1 MULTI-PROCESSOR™ Fluid Bed connected to a laboratory module Precision Coater available from Niro Inc. of Columbia, Md. MULTI-PROCESSOR™ is a trademark of Niro Inc.

In another exemplary embodiment, low intensity mixing may be used. Low intensity, i.e. low shear, mixing may be performed using a Diosna P100 Granulator, available from Diosna GmbH of Osnabrück, Germany, a subsidiary of Multimixing S.A. In another exemplary embodiment, high shear mixing may be used. High shear mixing of UHMWPE and tocopherol may be achieved using a RV02E or a R05T High Intensity Mixer, both commercially available from Eirich Machines of Gurnee, Ill. Alternatively, high shear mixing may be achieved using a Collette ULTIMAPRO™ 75 One Pot Processor available from Niro, Inc. of Columbia, Md. ULTIMAPRO™ is a trademark of Niro, Inc. Based on the results of testing the above identified methods useful for combining UHMWPE and tocopherol, high shear mixing appears to provide favorable results, including an acceptable homogeneity and a low number of indications, i.e., areas of high tocopherol concentrations relative to the surrounding areas as determined by visual inspection under ultraviolet light or by chemical measurements, such as infrared spectroscopy or gas chromatography. Additionally, in other exemplary embodiments, fluidized bed, emulsion polymerization, electrostatic precipitation, wetting or coating of particles, and/or master batch blending may be used to combine the UHMWPE and tocopherol.

Irrespective of the method used to combine the UHMWPE and tocopherol to form the antioxidant stabilized UHMWPE, the components are combined in ratios necessary to achieve a tocopherol concentration of between 0.01 weight percent (wt. %) and 3 wt. %. In exemplary embodiments, the tocopherol concentration may be as low as 0.01 wt. %, 0.05 wt. %, and 0.1 wt. %, or as high as 0.6 wt. %, 0.8 wt. %, and 1.0 wt. %, for example. In determining the appropriate amount of tocopherol, two competing concerns exist. Specifically, the amount selected must be high enough to quench free radicals in the UHMWPE, but must also be low enough to allow sufficient crosslinking so as to maintain acceptable wear properties of the antioxidant stabilized UHMWPE. In one exemplary embodiment, a range of tocopherol from 0.1 to 0.6 wt. % is used to successfully quench free radicals while still maintaining acceptable wear properties.

Once the antioxidant stabilized UHMWPE is substantially homogenously blended and the amount of tocopherol is determined to be within an acceptable range, the antioxidant stabilized UHMWPE is secured to bone contacting layer 12 to form inner layer layer 14. In one exemplary embodiment, the antioxidant stabilized UHMWPE is secured to bone contacting layer 12, as described in detail below. Once secured to bone contacting layer 12, the antioxidant stabilized UHMWPE may be exposed to crosslinking irradiation.

In preparing an antioxidant stabilized UHMWPE for exposure to crosslinking irradiation, the antioxidant stabilized UHMWPE may be preheated. In one exemplary embodiment, the antioxidant stabilized UHMWPE may be preheated to any temperature between room temperature, approximately 23° C., up to the melting point of the antioxidant stabilized UHMWPE, approximately 140° C. In another exemplary embodiment, the antioxidant stabilized UHMWPE is preheated to a temperature between 60° C. and 130° C. In other exemplary embodiments, the antioxidant stabilized UHMWPE may be heated to a temperature as low as 60° C., 70° C., 80° C., 90° C., or 100° C. or as high as 110° C., 120° C., 130° C., 135° C., 140° C. By preheating the antioxidant stabilized UHMWPE before irradiation, the material properties of the resulting irradiated antioxidant stabilized UHMWPE are affected. Thus, the material properties for an antioxidant stabilized UHMWPE irradiated at a relatively cold, e.g., approximately 40° C., temperature are substantially different than the material properties for an antioxidant stabilized UHMWPE irradiated at a relatively warm, e.g., approximately 120° C. to approximately 140° C., temperature.

However, while the material properties of an antioxidant stabilized UHMWPE irradiated at a lower temperature may be superior, the wear properties, fatigue properties, oxidation level, and free radical concentration are all negatively affected. In contrast, while irradiation of an antioxidant stabilized UHMWPE at a higher temperature may slightly diminish the material properties, it also results in a higher crosslinking efficiency due to higher chain mobility and adiabatic melting. Additionally, by irradiating at a higher temperature, a greater number of crosslinks are formed. Thus, there are less free radicals in the antioxidant stabilized UHMWPE and less tocopherol is consumed by reacting with the free radicals during irradiation and immediately thereafter. As a result, a greater amount of tocopherol remains in the blend that may react with free radicals during the antioxidant stabilized UHMWPE's lifecycle, i.e., after irradiation. This, in turn, increases the overall oxidative stability of the antioxidant stabilized UHMWPE.

Additionally, when the antioxidant stabilized UHMWPE forming inner layer 14 and the porous metal of bone contacting layer 12 are irradiated, bone contacting layer 12 may rapidly increase in temperature. Thus, the temperature increase of bone contacting layer 12 should be taken into account when determining the preheat temperature of the antioxidant stabilized UHMWPE forming inner layer 14 and the porous metal of bone contacting layer 12.

After the temperature of the antioxidant stabilized UHMWPE forming inner layer 14 reaches the desired preheat temperature, the antioxidant stabilized UHMWPE is subsequently irradiated to induce crosslinking of the UHMWPE. Thus, as used herein, "crosslinking irradiation" refers to exposing the antioxidant stabilized UHMWPE to ionizing irradiation to form free radicals which may later combine to form crosslinks. The irradiation may be performed in air at atmospheric pressure, in a vacuum chamber at a pressure substantially less then atmospheric pressure, or in an inert environment, i.e., in an argon environment, for example. The irradiation is, in one exemplary embodiment, electron beam irradiation. In another exemplary embodiment, the irradiation is gamma irradiation. In yet another exemplary embodiment, the crosslinking does not require irradiation, but instead utilize silane crosslinking. In one exemplary embodiment, crosslinking is induced by exposing the antioxidant stabilized UHMWPE to a total radiation dose between about 25 kGy and 1,000 kGy. In another exemplary embodiment, crosslinking is induced by exposing the antioxidant stabilized UHMWPE to a total radiation dose between about 50 kGy and 250 kGy in air. These doses are higher than doses commonly used to crosslink UHMWPE due to the presence of antioxidant in the antioxidant stabilized UHMWPE. Specifically, the antioxidant reacts with some of the polyethylene chains that became free radicals during irradiation. As a result, a higher irradiation dose must be administered to the antioxidant stabilized UHMWPE to achieve the same level of crosslinking that would occur at a lower dose in conventional UHMWPE, i.e., UHMWPE absent an antioxidant.

Figure 4:
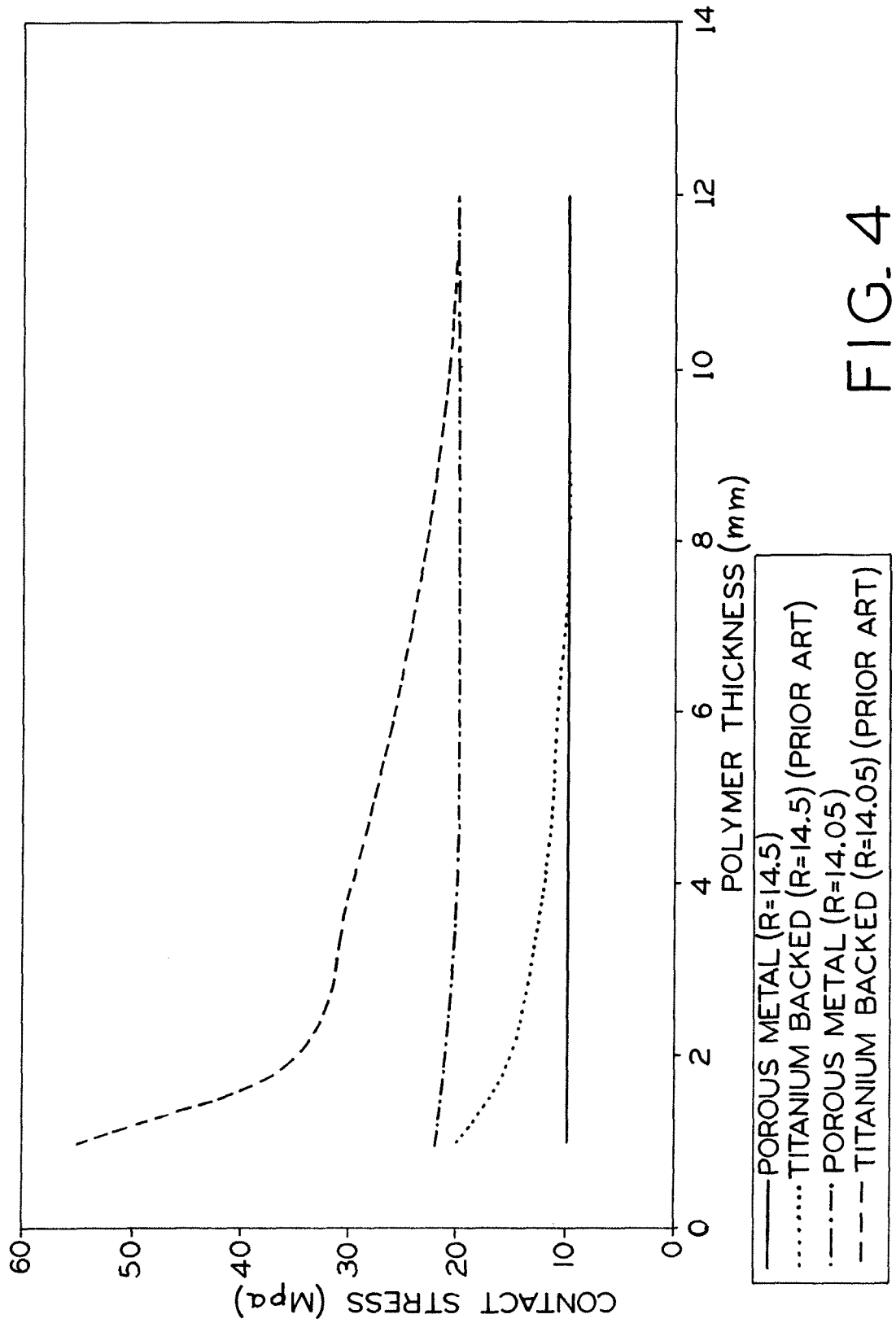
FIG. 4 depicts a graphical illustration of the relationship between contact stress and the thickness of a polymer material.

Advantageously, by utilizing an antioxidant stabilized, crosslinked polymer to form inner layer 14 of acetabular component 10, the thickness of inner layer 14 may be substantially reduced. For example, the thickness of bearing layer 26, shown in FIG. 2B and described below, of inner layer 14 may be less then 4 mm and still maintain the same level of contact stress as known acetabular cups having a bearing layer thicker than 4 mm. As discussed above, it was previously believed by persons of ordinary skill in the art that bearing layer 26 of a metal backed orthopedic component must be equal to or greater than 4 mm. However, acetabular cup prosthesis 10 has a substantially lower elastic modulus than known acetabular cup designs. As a result, under the same loading conditions, porous metal backed acetabular components will deform more and provide more contact area so that the peak contact stress of acetabular cup prosthesis 10 is lowered, as shown in FIG. 4. Additionally, forming an acetabular component having a decreased thickness of bearing layer 26 allows for a greater range of motion of a mating femoral head component and also reduces the outer diameter of the acetabular component, which results in the preservation of a patient's natural bone stock. Additional information regarding the specific properties of an orthopedic component of the present invention having an antioxidant stabilized polymer inner layer 14 is set forth below in the corresponding Examples.

To manufacture acetabular shell 10, bone-contacting layer 12 is formed using traditional techniques, such as milling, molding, and/or machining. Once formed and/or machined to have the desired characteristics, inner layer 14 is attached to bone contacting layer 12. In one exemplary embodiment, inner layer 14 is attached to bone contacting layer 12 by injection or compression molding. By utilizing a porous metal, e.g., a material formed using Trabecular Metal™ technology or a metal having a porous coating to form bone-contacting layer 12, the attachment of the inner layer 14 allows the biocompatible polymer forming inner layer 14 to be received within the pores of bone-contacting layer 12. This interaction creates a rigid, mechanical bond between bone contacting layer 12 and inner layer 14 to fixedly attach the two layers together, which allows for the transfer of the forces between bone contacting layer 12 and inner layer 14 that are encountered during the loading of the joint.

Referring to FIGS. 2A and 2B, the polymeric material of inner layer 14 may be molded at least partially within the porous substrate of bone contacting layer 12 to a desired depth to thereby form a unified construct by which the polymeric material of inner layer 14 is connected to bone contacting layer 12 by interdigitation of the polymeric material of inner layer 14 at least partially within the pores or channels 18 of bone contacting layer 12. In this manner, referring to FIG. 2B, the implant construct generally includes three layers, including porous layer 22, which will contact and interface with bone tissue when acetabular cup 10 is implanted within a patient, interdigitation layer 24 in which the polymeric material of inner layer 14 is infiltrated within bone contacting layer 12, and bearing layer 26 comprising the polymeric material of inner layer 14 and defining bearing surface 20. Thus, interdigitation layer 24 defines an intermeshing region in which the material of bearing layer 26 intermeshes with the material of porous layer 22 and the interaction between the polymeric material of bearing layer 26 and ligaments 16 defining voids or channels 18 of porous layer 22 retains bearing layer 26 thereon.

By varying the thickness of each of these three layers, i.e., porous layer 22, interdigitation layer 24, and bearing layer 26, as well as the porosity of porous layer 22, orthopedic components having varying stiffness may be created. Advantageously, this allows for a surgeon or other medical professional to select an orthopedic component that has a stiffness that is substantially similar to the bone stiffness of an individual patient. Additionally, this allows for manufacturers of orthopedic components to design and manufacture orthopedic components that have a stiffness that is substantially similar to the stiffness of the bone into which the orthopedic component is designed to be implanted. For example, if the orthopedic component is an acetabular component, the thickness of porous layer 22, interdigitation layer 24, and bearing layer 26 may be selected to create an orthopedic component having an effective stiffness that is substantially similar to the elastic modulus of the bone of the pelvis. Similarly, if the orthopedic component is a glenoid component, the thickness of porous layer 22, interdigitation layer 24, and bearing layer 26 may be selected to create an orthopedic component having an effective stiffness that is substantially similar to the elastic modulus of the bone of the glenoid of the scapula. Additional detailed information regarding specific thicknesses of each of the above-identified layers and the resulting effective stiffness achieved using the same are set forth below in the corresponding Examples.

Once the attachment, e.g., injection or compression molding, of inner layer 14 to bone contacting layer 12 is finished, acetabular shell 10 may be complete, i.e., ready for implantation. If acetabular shell 10 is not finished at the conclusion of the attachment process, acetabular shell 10 may be further machined to create a final, implantable acetabular shell. In one exemplary embodiment, acetabular component 10, having bone contacting layer 12 and inner layer 14 forms the entire implantable acetabular prosthesis. Thus, in this embodiment, a corresponding femoral prosthesis would articulate against bearing surface 20. However, in another exemplary embodiment, bearing surface 20 may define a contact and/or support surface for an acetabular liner. In this embodiment, in order to complete the acetabular component of a hip prosthesis system, an acetabular liner may be provided. The acetabular liner, such as liners 28, 30 described below, receive the head of a femoral prosthesis to replicate the natural hip joint.

Figure 3:
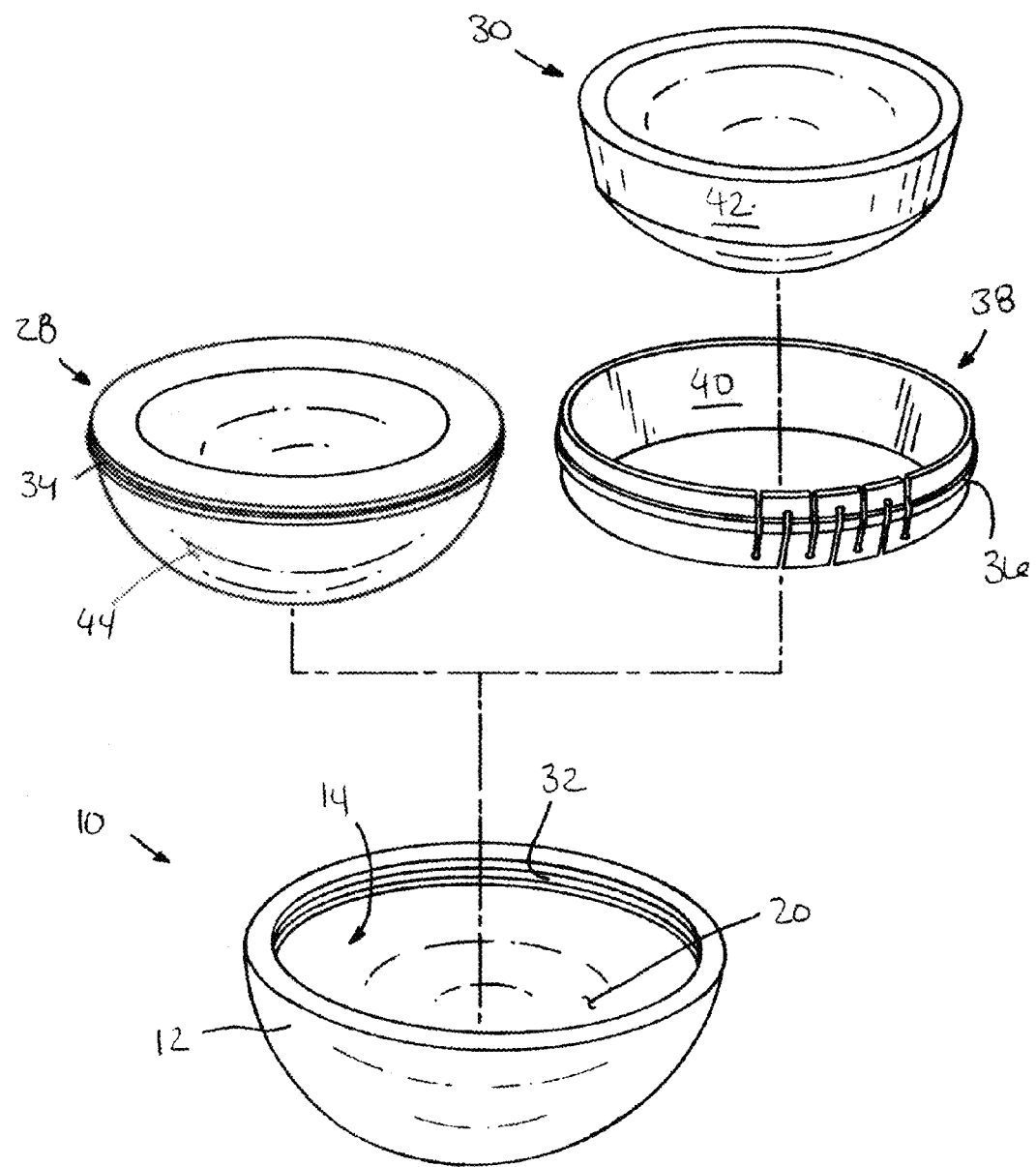
FIG. 3 is an assembly view of the acetabular shell of FIG. 1 depicting alternative acetabular liners.

To facilitate attachment of an acetabular liner to acetabular shell 10, an integral locking feature may be incorporated into inner layer 14 during the process of attaching inner layer 14 to bone contacting layer 12. Referring to FIG. 3, in one exemplary embodiment, groove 32 may be formed in inner layer 14 on bearing surface 20. For example, groove 32 may extend around bearing surface 20 proximate to and/or at the equator of inner layer 14. Groove 32 may be configured to mate with rib 34 formed on acetabular liner 28, which may be formed from polyethylene. Acetabular liner 28 may then be retained within acetabular shell 10 via the snap-fit connection of groove 32 and rib 34.

Additionally, in another exemplary embodiment, groove 32 may also be configured to mate with rib 36 formed on conversion ring 38. Conversion ring 38 includes an inner tapered surface 40 which may be configured to mate with outer tapered surface 42 on acetabular liner 30. Acetabular liner 30 may be formed from metal or ceramic, for example. Thus, conversion ring 38 may be retained within acetabular shell 10 via the snap-fit connection of groove 32 and rib 36. Acetabular liner 30 may then be received by conversion ring 38 and retained within acetabular shell 10 by the locking engagement of inner tapered surface 40 of conversion ring 38 and outer tapered surface 42 of acetabular liner 30. Additional details regarding the operation and use of conversion ring 28 are set forth in co-pending U.S. patent application Ser. No. 11/401,727, entitled "ACETABULAR CUP CONVERSION RING", filed Apr. 11, 2006, the entire disclosure of which is hereby expressly incorporated by reference herein.

In another exemplary embodiment, the integral locking feature may be configured to receive a spring ring or any other locking component. In yet another exemplary embodiment, the integral locking feature may be a Morse taper. This Morse taper may be formed as a self-locking taper configured to mate with a corresponding acetabular liner without the use of conversion ring 38. Advantageously, the use of the integral locking feature allows for a surgeon to easily switch between different liners and may also lessen the number of components needed to form the complete acetabular cup assembly.

Additionally, when inner layer 14 is attached to bone contacting layer 12, inner layer 14 may be formed with smooth bearing surface 20 that may be smoother than the inner or bearing surface of known acetabular cups. For example, known acetabular cups have a bearing surface that has an arithmetical mean roughness (Ra) of no less than 13 microns. In contrast, smooth bearing surface 20 may have an Ra as low as 1, 2, 3, or 4 microns or as high as 7, 8, 9, or 10 microns. In one exemplary embodiment, smooth bearing surface 20 has an Ra between approximately 4 microns and 8 microns. The formation of smooth bearing surface 20 may minimize wear debris that could potentially be created between bearing surface 20 of inner layer 14 and outer surface 44 of liner 28 during joint articulation.

Further, if the attachment of inner layer 14 to bone contacting layer 12 is accomplished by injection molding, surface 18 will have the same finish, i.e., the same roughness, as the corresponding surface of the injection mold. Thus, the corresponding injection mold surface can be polished to a smooth finish and the need to further smooth or polish bearing surface 20 of acetabular shell 10 is substantially eliminated. Advantageously, this lowers manufacturing costs by shortening the manufacturing process and lessening the labor and tool costs of the same. Additionally, the surface roughness of inner layer 14 may be substantially similar to the surface roughness of liner 28. As a result of the substantially similar surface roughness of inner layer 14 and liner 28, the creation of wear debris may be further minimized.

In preparation for the implantation of acetabular shell 10, a surgeon may examine the acetabulum to determine the location having the greatest amount of and/or strongest area of bone stock. Referring to FIG. 1, once this determination is made, the surgeon may drill bone screw receiving apertures 46 within acetabular shell 10 that may align with the previously identified areas. Advantageously, by allowing a surgeon to customize the location of the bone screw receiving apertures in an orthopedic component, the costs of inventorying different orthopedic components with various bone screw receiving aperture configurations and machining the same are substantially eliminated. Then, once acetabular shell 10 is ready for implantation, acetabular shell 10 is inserted into the prepared, natural acetabulum and a bone screw, such as bone screw 48, is positioned within aperture 46 and threaded into the patient's natural bone stock. In one exemplary embodiment, once bone screw 48 is affixed to the patient's bone stock, one of liners 28, 30 may be connected to acetabular shell 10 in the manner described above. In another exemplary embodiment, bone screw 48 may be countersunk into aperture 46, such the substantial entirety of head 50 of bone screw 48 is positioned within outer layer 12. Alternatively, in another exemplary embodiment, the liner may be attached to acetabular shell 10 prior to implantation, and the two components implanted together and retained in position in the patient's acetabulum using bone cement, for example.

Advantageously, due to the attachment of bone contacting layer 12 and inner layer 14, any dust and/or debris generated during the drilling of bone screw receiving apertures 46 will be substantially contained within the polymeric debris of inner layer 14. This allows for a surgeon to easily remove any dust and/or debris generated during the creation of the bone screw receiving apertures from acetabular shell 10 by removing the metallic dust or debris and the larger polymer shavings that may have encapsulated additional metallic dust or debris during the drilling operation.

EXAMPLES

The following non-limiting Examples illustrate various features and characteristics of the present invention, which is not to be construed as limited thereto. The following abbreviations are used throughout the Examples unless otherwise indicated.

TABLE 1

Abbreviations

| Abbreviation | Full Word |
|---|---|
| $E_{eff}$ | effective stiffness |
| PEEK | polyetheretherketone |
| R | Radius |
| mm | millimeter |
| H | height |
| Δ | change |
| $\sigma_{eff}$ | effective stress |
| $\epsilon_{eff}$ | effective strain |
| σ | stress |
| ε | strain |
| UHMWPE | ultrahigh molecular weight polyethylene |
| L | length |
| PM | porous material |
| GPa | Gigapascals |
| lbf | Pound feet |
| π | 3.14159265 |
| r | radial displacement |
| t | thickness |
| $T_p$ | thickness of polymer layer |
| $T_t$ | thickness of porous metal layer |
| $T_i$ | thickness of interdigitation layer |
| φ | porosity |
| kGy | kilo Gray |
| min | minute |
| MeV | mega electron volt |
| m | meter |
| ° | degrees |
| C. | Celsius |
| FTIR | Fourier Transform Infrared Spectroscopy |
| wt. % | weight percent |
| MPa | Megapascal |
| UTS | ultimate tensile strength |
| YS | yield strength |
| HXPE | highly crosslinked polyethylene |
| OI | Oxidation Index |
| T | Temperature |
| DSC | Differential Scanning Calorimetry |
| ml | milliliter |
| nm | nanometer |
| TVI | trans-vinylene index |
| VEI | d/l-α-tocopherol index |
| Mc | million cycles molecular weight between crosslinks |
| AVE | aged vitamin E percent |
| AVEI | aged vitamin E index |
| AV-OI | aged oxidation index |
| mg | milligram |
| cm | centimeter |
| IR | infrared |
| VE % | weight percent tocopherol |
| Vol | volume |
| wt. | weight |
| VE | tocopherol |
| g | gram |
| DMA | Dynamic Mechanical Analysis |
| kJ | kilojoule |
| Izod | Izod Impact Strength |
| Conc. | Concentration |
| dm | decimeter |

Example 1

Effective Stiffness of PEEK Layer/Porous Layer Construct

An analytical model was used to study the effective stiffness of a layer of PEEK positioned adjacent to a layer of porous metal.

The effective stiffness of a layer of PEEK positioned adjacent to a layer of porous metal is dependent on both the material properties and geometries of the individual layers. Thus, to attempt to remove any geometric effects, an analytical model was created to include a rectangular PEEK layer positioned atop a corresponding rectangular porous metal layer. The model incorporated frictionless contact between the PEEK layer and porous metal layer and with none of the PEEK penetrating into the pores of the porous metal layer. Additionally, the porous metal layer is assumed to have properties substantially similar to a porous metal layer formed in accordance with Trabecular Metal™ technology, as described in detail above. The model was then subjected to uniaxial compression. The stress is equally carried by both materials and the compressive displacement of the materials is additive. Thus, the total displacement in the model is calculated as:

$$\Delta L_{total} = \Delta L_{PEEK} + \Delta L_{Porous} = \varepsilon_{PEEK} L_{PEEK} + \varepsilon_{Porous} L_{Porous} = \frac{\sigma}{E_{PEEK}} L_{PEEK} + \frac{\sigma}{E_{Porous}} L_{Porous}$$

Thus, the effective stiffness of the two material construct is:

$$E_{eff} = \frac{\sigma}{\varepsilon_{total}} = \frac{\sigma L}{\Delta L_{total}} = \frac{L_{PEEK} + L_{Porous}}{L_{PEEK}/E_{PEEK} + L_{Porous}/E_{Porous}}$$

Since different stiffness values are available for a porous metal layer formed in accordance with Trabecular Metal™ technology and since different applications may require different thicknesses of the PEEK layer and the porous metal layer, the effective stiffness was modeled under a range of values. Effective stiffnesses were modeled with the stiffness of the porous metal layer varying between 1-3 GPa, the thickness of the PEEK layer varying between 2.0 and 5.8 mm, and the thickness of the porous metal layer remaining constant at 4 mm. The resulting effective stiffnesses are shown in TABLE 2, in addition to some representative stiffnesses, i.e., Young's moduli, of various materials.

TABLE 2

| Material | Stiffness (GPa) |
|---|---|
| CoCr | 210 |
| Ti | 110 |
| PEEK | 4 |
| TM | 1-3 |
| UMWPE | 1 |

Porous 4 mm / PEEK 2 mm
$E_{eff}$ = 1.3-3.3 GPa

Porous 4 mm / PEEK 5.8 mm
$E_{eff}$ = 1.8-3.5 GPa

Referring to TABLE 2, the results indicated that with a porous metal layer of 4 mm and a PEEK layer of 2 mm, the effective stiffness of the construct was 1.3 GPa when 1.0 GPa was used as the elastic modulus of the porous metal layer. Additionally, with a porous metal layer of 4 mm and a PEEK layer of 2.0 mm, the effective stiffness of the construct was 3.3 GPa when 3.0 GPa was used as the elastic modulus of the porous metal layer. Further, the results indicated that with a porous metal layer of 4 mm and a PEEK layer of 5.8 mm, the effective stiffness of the construct was 1.8 GPa when 1.0 GPa was used as the elastic modulus of the porous metal layer.

Additionally, with a porous metal layer of 4 mm and a PEEK layer of 5.8 mm, the effective stiffness of the construct was 3.5 GPa when 3.0 GPa was used as the elastic modulus of the porous metal layer.

Example 2

Effects of Acetabular Cup Geometry on PEEK Layer/Porous Layer Stiffness

A Finite Element (FE) model was used to study the effective stiffness of an idealized acetabular hip cup model having a layer of PEEK interdigitated with a layer of porous metal.

A 3-D parametric FE model was developed using commercially available FE software ABAQUS 6.7 (ABAQUS, Inc., Providence R.I., USA). The FE model included a femoral component, an acetabular cup, and a bone cement boundary. The femoral component was modeled to be rigid and spherical with a radius, $R_{femoral}$, of 16 mm. The acetabular cup was modeled to have a series of successive layers. The innermost layer is a UHMWPE layer which forms the acetabular liner of the acetabular construct and against which the femoral component articulates. The acetabular shell of the acetabular construct was modeled to have an innermost PEEK layer, an interdigitated PEEK/porous metal layer, and an outermost porous metal layer. The porous metal layer was modeled to have the properties of a material formed in accordance with Trabecular Metal™ technology, as described in detail above.

Additionally, the total polymer thickness, i.e., the combined thickness of the UHMWPE and PEEK layers, was modeled to be 7.8252 mm, with two separate distributions between the polymers tested. The first distribution was modeled with a UHMWPE layer thickness of 5.8252 mm and a PEEK layer thickness of 2.0 mm and the second distribution was modeled with a UHMWPE layer thickness of 2.0252 mm and a PEEK layer thickness of 5.8 mm. The PEEK/porous metal layer, i.e., the interdigitated layer, was modeled to have a constant thickness of 2.1248 mm and the porous metal layer was modeled to have a constant thickness of 2.077 mm. This entire construct was modeled to be embedded in a block of bone cement having an outer radius, $R_{cement}$, of 48.027 mm and a height, $H_{cement}$, of 48.027 mm.

Each of the material interfaces described above was also modeled to be in a completely bonded state, including the interface between the acetabular shell and the bone cement, and the coefficient of friction for articulation of the femoral component on the UHMWPE layer was modeled to be 0.02. The elastic modulus that was modeled for each of the layers is set forth in TABLE 3 below. All materials were modeled to have a Poisson's ratio of 0.3.

TABLE 3

| Layer | Elastic Modulus (GPa) |
| --- | --- |
| UHMWPE | 1.00 |
| PEEK | 4.00 |
| PEEK/Porous metal | 6.85 |
| Porous metal | 3.00 |
| Bone Cement | 3.00 |

Using the model set forth above, the femoral head was loaded by applying a 1700 lbf load to the femoral head at a 45 degree angle relative to the polar axis of the acetabular cup construct, with the outer boundary of the bone cement fully constrained, as shown in FIG. 6. The resulting displacement of the femoral component was calculated. The effective stiffness of the acetabular construct was calculated using the effective stress and the effective strain. Thus, the effective stress was calculated as the force applied to the femoral component, i.e., 1700 lbf, divided by the internal surface area of the cup, i.e., $2\pi R^2_{femoral}$. The effective strain was calculated as the radial displacement of the femoral component, i.e., $\Delta r_{head}$, divided by the total thickness of the acetabular cup construct, i.e., $t_{cup} = t_{UHMWPE} + t_{PEEK} + t_{Porous/PEEK} + t_{Porous}$. Therefore, the effective stiffness is $$E_{eff} = \frac{\sigma_{eff}}{\varepsilon_{eff}} = \frac{F/2\pi R^2_{femoral}}{\Delta r_{head}/t_{cup}}$$

Utilizing the model described above, the effective stiffness of the acetabular construct having a UHMWPE layer thickness of 5.8252 mm and a PEEK layer thickness of 2.0 mm is $E_{eff} = 0.45$ GPa and the effective stiffness of the acetabular construct having a UHMWPE layer thickness of 2.0252 mm and a PEEK layer thickness of 5.8 mm is $E_{eff} = 0.54$ GPa.

Example 3

Effects of Layer Thickness on a Porous Metal/UHMWPE Orthopedic Component

Figure 8:
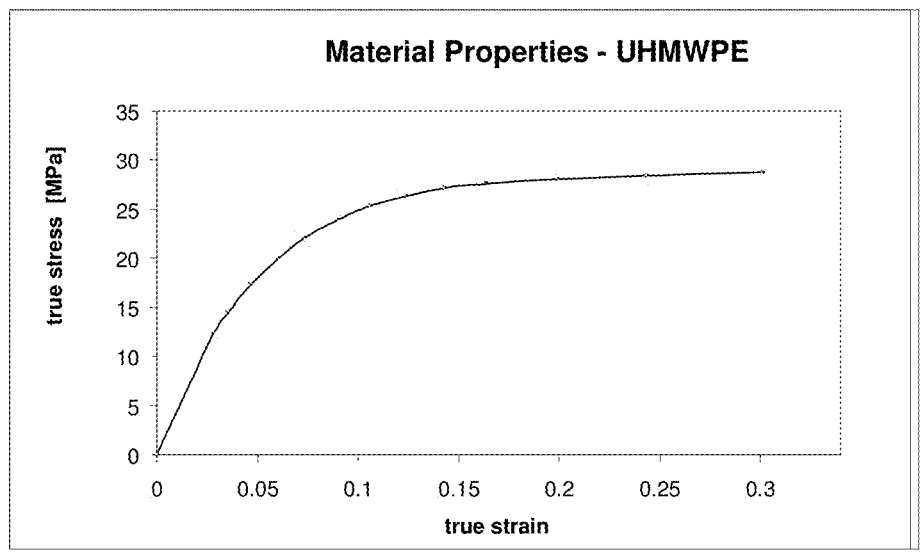
FIG. 8 depicts a graphical illustration of the stress/strain properties of both conventional UHMWPE and antioxidant stabilized UHMWPE.
Figure 9:
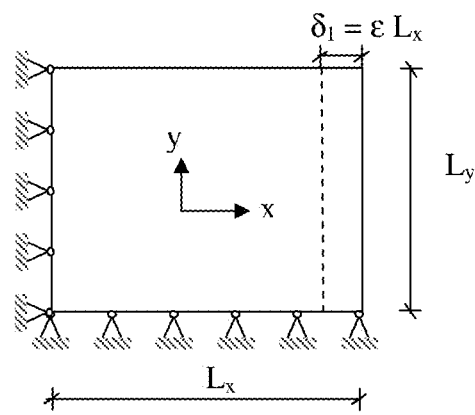
FIG. 9 depicts a graphical illustration of an unconfined compression loading condition.

A 2D stochastic microstructural FE model was developed to represent an idealized acetabular hip cup having a layer of UHMWPE interdigitated with a layer of porous metal. The internal geometry was based on a 2D random Voronoi structure generated by a custom program in FORTRAN. This program also allows changing parametrically the thickness of the three layers, i.e., the UHMWPE layer, the interdigitated layer, and the porous metal layer, to create different designs. Tantalum microstructs, such as those formed in a material created using Trabecular Metal™ technology, are portions of ligaments 16, shown in FIG. 2a, having a loose end and defining the perimeter of the porous metal layer. These tantalum microstructs were modeled as a bilinear elastic material, as shown in FIG. 7, whereas UHMWPE was modeled as a multilinear elastic material, as shown in FIG. 8. Additionally, the various properties of the UHMWPE that were used in the model correspond to properties of an antioxidant stabilized, crosslinked UHMWPE, as set forth herein. The elements used in the FE model were PLANE183 which are eight-node quadratic elements with quadratic displacement behavior and are well suited to model irregular meshes in 2D. The FE models thus generated generally included more than 50,000 elements. Once the model was prepared, uniaxial compression was simulated using an unconfined compression loading condition, as shown in FIG. 9. Unconfined compression permits free dimensional change in directions transverse to the one in which load is applied. FIG. 9 depicts a change in dimension $\delta_1$ in the horizontal dimension parallel to the x-axis. The object is free to deform in the vertical dimension parallel to the y-axis.

Using the above-identified assumptions, a three-parameter, two-level full factorial analysis was performed to investigate the effect of design parameters, i.e., the porosity ($\phi$) of the porous metal, the thickness of the interdigitation layer ($T_i$), and the ratio of the UHMWPE layer thickness to the porous metal layer thickness ($T_p/T_i$) on the overall linear elastic stiffness, i.e., modulus, of the construct. The factors and their respective low and high levels are shown in TABLE 4 below. The overall construct thickness was kept constant with a total thickness of 10 mm. The porosity of the construct was assumed to be 65 and 85%, respectively.

TABLE 4

| Factor | Low Level | High Level |
|---|---|---|
| Porosity, % | 65 | 85 |
| $T_p/T_t$ | 0.6 | 3.0 |
| $T_i$ [mm] | 2 | 3 |

After determining the more significant effects from a Design of Experiments ("DOE") factorial analysis, a parametric study was performed to evaluate the mechanical behavior, such as the elastic modulus, of the modeled porous metal/UHMWPE construct. The DOE analysis determined which of the parameters identified in TABLE 4 have the greatest influence on predicted mechanical response (i.e., stiffness which defines the amount of deflection for a given load). Those parameters are % porosity, polyethylene thickness $T_p$ and Trabecular Metal thickness $T_t$. Different and representative values of porosities and layer thicknesses were chosen based on current implant designs. The overall thickness of the entire construct and that of the interdigitation layer were kept constant at 10 mm and 2 mm, respectively. Additionally, values of 0.6 and 3.0 were used for the ratio of the thickness of the porous metal layer to the thickness of the polymer layer and values of 65% and 85% were used for the porosity of the porous metal layer. The matrix of thickness and porosity combinations investigated is shown below in TABLE 5. FE analysis was performed with ANSYS 10 finite analysis software (ANSYS, Inc., Canonsburg, Pa., USA) to simulate uniaxial compression loading condition as set forth in FIG. 9.

TABLE 5

Analysis Factor Combinations

| | Porosity, % | | | | | | | | | | | | | | | | | | | |
|---|---|---|---|---|---|---|---|---|---|---|---|---|---|---|---|---|---|---|---|---|
| | 65 | | | | 70 | | | | 75 | | | | 78 | | | | 85 | | | |
| $T_p$ (mm) | 3 | 4 | 5 | 6 | 3 | 4 | 5 | 6 | 3 | 4 | 5 | 6 | 3 | 4 | 5 | 6 | 3 | 4 | 5 | 6 |
| $T_i$ (mm) | 2 | 2 | 2 | 2 | 2 | 2 | 2 | 2 | 2 | 2 | 2 | 2 | 2 | 2 | 2 | 2 | 2 | 2 | 2 | 2 |
| $T_t$ (mm) | 5 | 4 | 3 | 2 | 5 | 4 | 3 | 2 | 5 | 4 | 3 | 2 | 5 | 4 | 3 | 2 | 5 | 4 | 3 | 2 |

Figure 10:
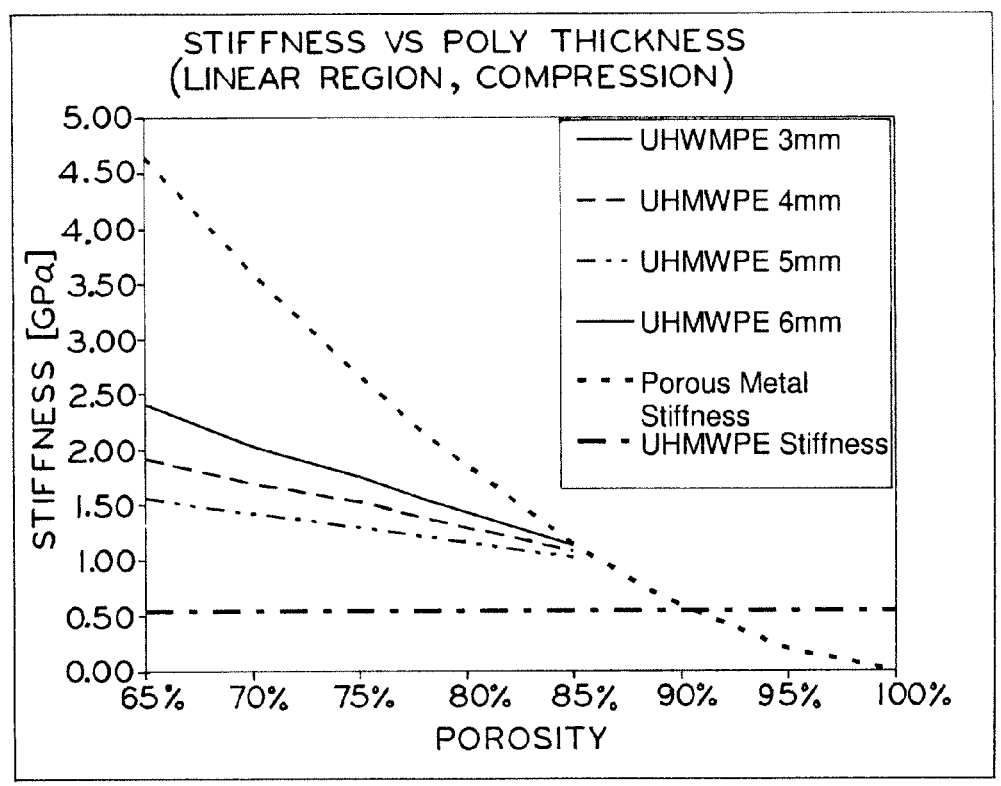
FIG. 10 depicts a graphical illustration of the effect of porosity on a construct's stiffness.
Figure 11:
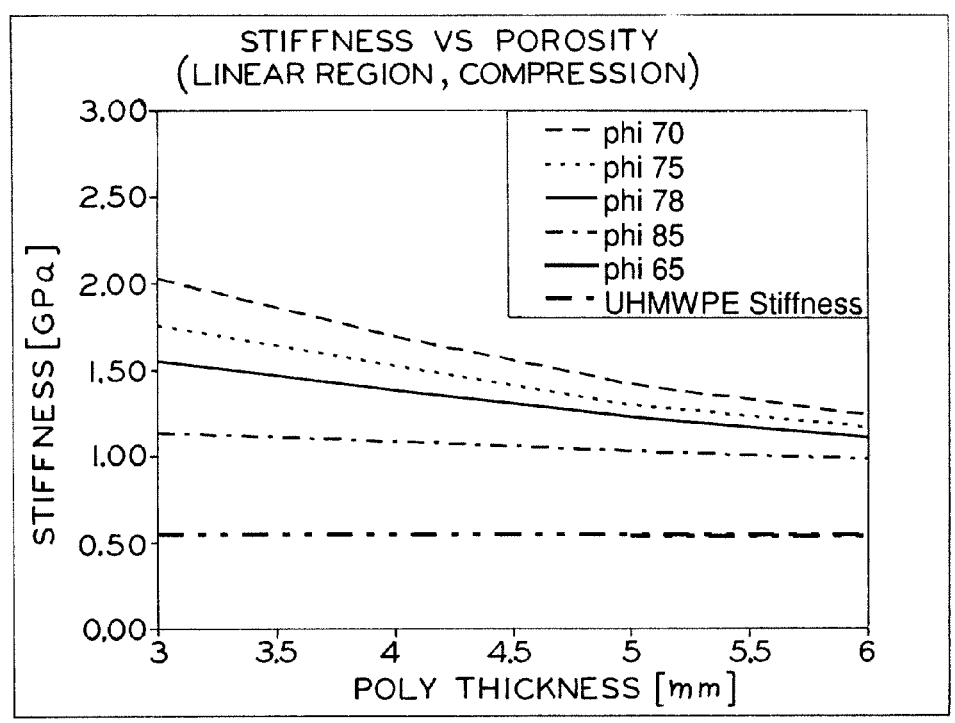
FIG. 11 depicts a graphical illustration of the effect of polymer thickness on a construct's stiffness.

The factorial analysis was performed for the response of the overall linear stiffness, i.e., elastic modulus, evaluated under compression loading conditions. The effects of overall response were evaluated considering a 95% confidence level. As shown in TABLE 6, the factorial analysis showed a significant interaction of the ratio of the porous metal layer thickness to the polymer layer thickness with the porosity of the metal. The thickness of the interdigitation layer was found to have little effect on the construct stiffness and was kept constant for the rest of the study. Specifically, it was determined that the percentage contribution of each significant factor and interaction to the model was 49.7% for porosity, 32.6% for the ratio of the porous metal layer thickness to the polymer layer thickness, 17.5% for the interaction of the ratio of the porous metal layer thickness to the polymer layer thickness with the porosity of the metal, and 0.27% for the thickness of the interdigitation layer. The results are plotted in TABLE 6 and FIGS. 10 and 11.

TABLE 6

| Test | Ti (mm) | Tp/Tt Ratio | Porosity of Metal Layer (%) | Elastic Modulus (GPa) |
|---|---|---|---|---|
| 1 | 2 | 0.6 | 65 | 2.413 |
| 2 | 3 | 0.6 | 65 | 2.46 |
| 3 | 2 | 3 | 65 | 1.325 |
| 4 | 3 | 3 | 65 | 1.343 |
| 5 | 2 | 0.6 | 85 | 1.134 |
| 6 | 3 | 0.6 | 85 | 1.235 |
| 7 | 2 | 3 | 85 | 0.982 |
| 8 | 3 | 3 | 85 | 1.046 |

Figure 12:
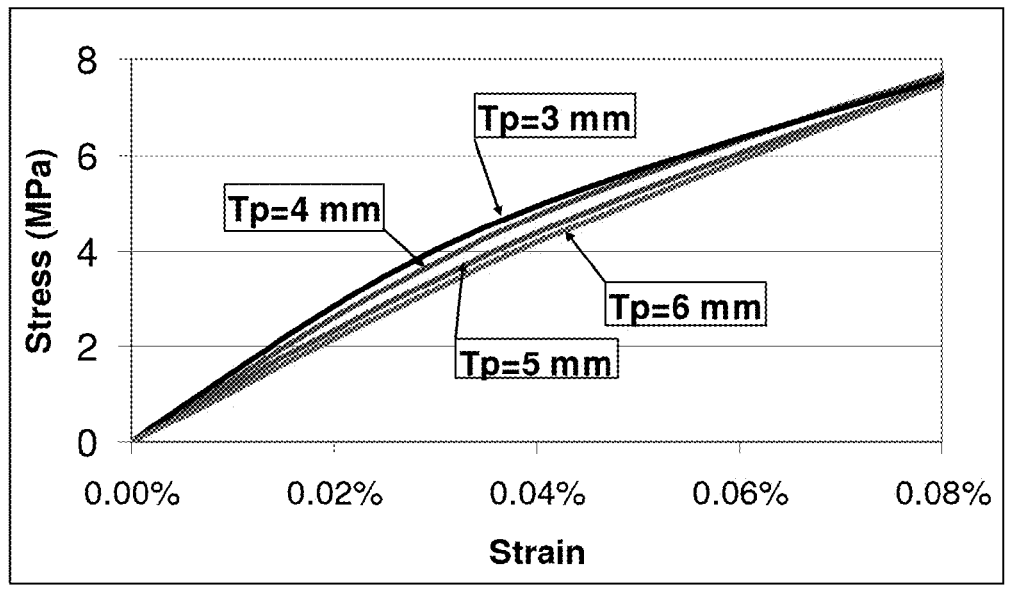
FIG. 12 depicts a graphical illustration of stress/strain properties for various polymer thicknesses.
Figure 13:
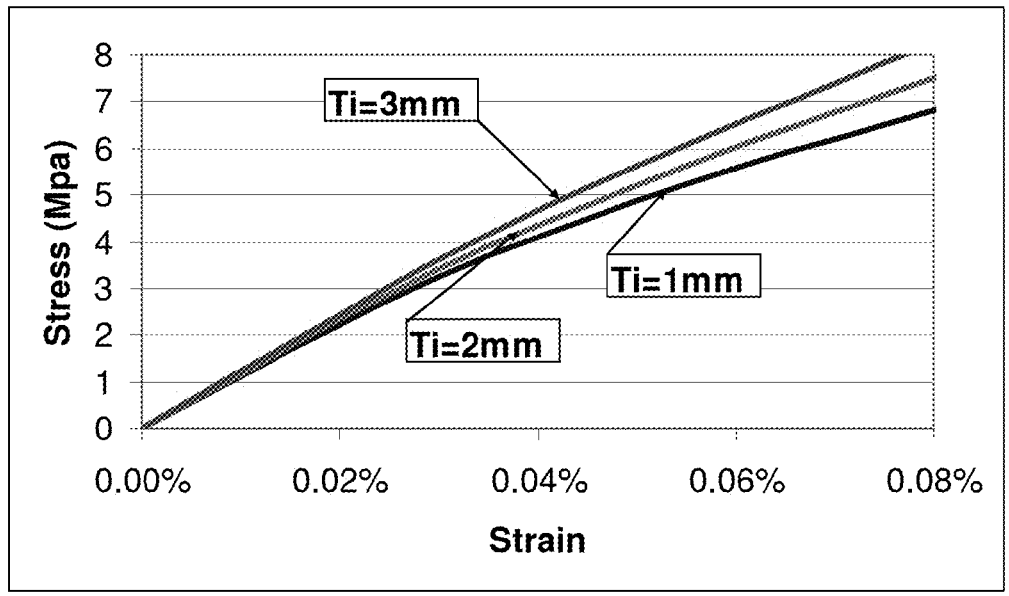
FIG. 13 depicts a graphical illustration of the stress/strain properties for different thicknesses of the interdigitation layer between the polymer and porous layers.

Based on these results, it was shown that the higher the porosity level of the porous metal, the lower the overall linear elastic structural stiffness, or elastic modulus, of the construct. It was also found that in the linear region the increase of UHMWPE thickness produced a decrease in the overall linear stiffness, or elastic modulus. The effects of the thickness of the interdigitation layer and the polymer layer on the nonlinear overall mechanical behavior were also explored. It can be seen from FIGS. 12 and 13 that in the linear region (e<0.02%), the increase of the UHMWPE layer thickness will decrease the elastic modulus (as indicated by the slope of the stress vs. strain curves) while the interdigitation layer thickness has little effect on the elastic modulus. In the nonlinear region (e>0.02%), the increase of the interdigitation layer increases the elastic modulus, while the increase in the polymer layer thickness has little change in the material.

Figure 14:
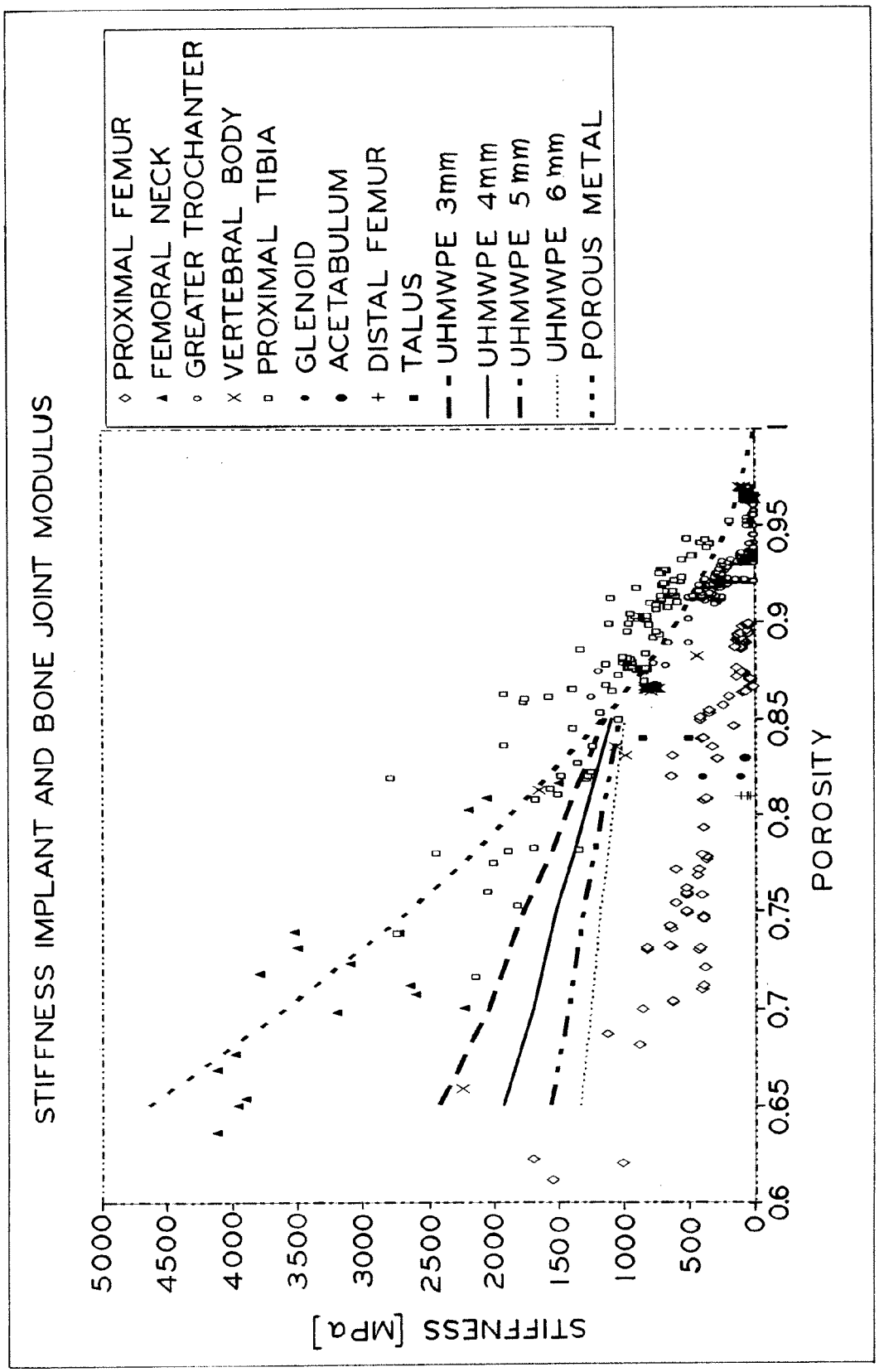
FIG. 14 depicts a graphical illustration of stiffness properties for various materials.
Figure 15:
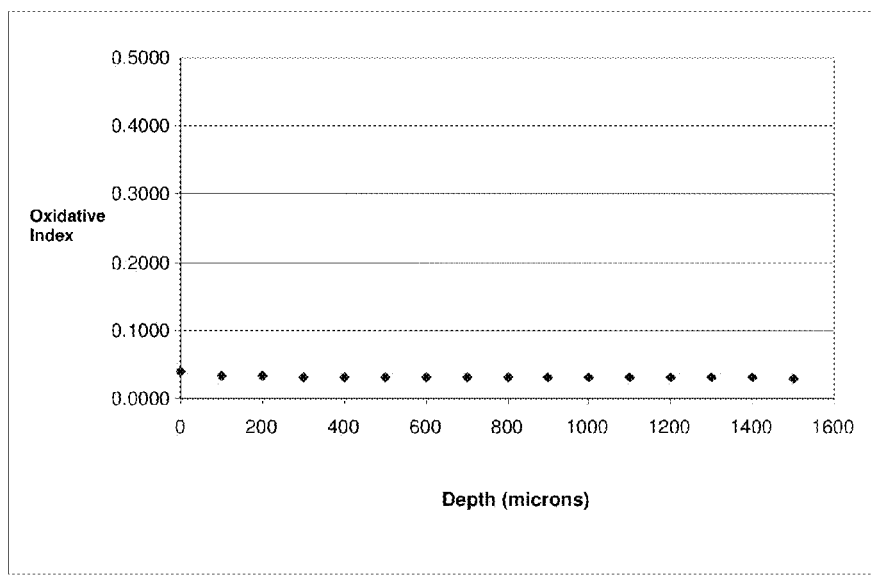
FIG. 15 depicts a graphical illustration of the oxidative index of UHMWPE blend with 0.50 weight percent α-tocopherol acetate.

Additionally, a clinically successful orthopedic component must have an appropriate stiffness to promote primary fixation, during the first months post-operatively, and secondary fixation with a constructive bone modeling/remodeling response. Bone resorption and subsequent implant loosening may be caused by high bone stresses as well as low bone stresses due to "stress shielding" from an overly stiff implant. Based on this, a preliminary design of a direct compression molded porous metal, such as a metal made in accordance with Trabecular Metal™ technology, and polymer, such as UHMWPE or PEEK, construct can be made to have a stiffness that is substantially similar to the stiffness of the bone into which the construct is to be implanted. As shown by the results of the current study, the construct's bulk linear stiffness is principally affected by the polymer layer thickness and the porosity of the porous metal. Additionally, the mechanical properties of bone are nonhomogeneous and anisotropic, varying between anatomical sites. Therefore, an implant may be designed with a given porosity of the porous metal layer and thicknesses of the polymer, interdigitated, and porous metal layers that targets the structural stiffness of its host bone. In one exemplary embodiment, this can be achieved by varying the thickness of the polymer layer, as shown by the solid and dashed curves in FIG. 14 with respect to UHMWPE.

Example 4

Effects of Antioxidant Stabilizing on Layer Thickness

Figure 5:
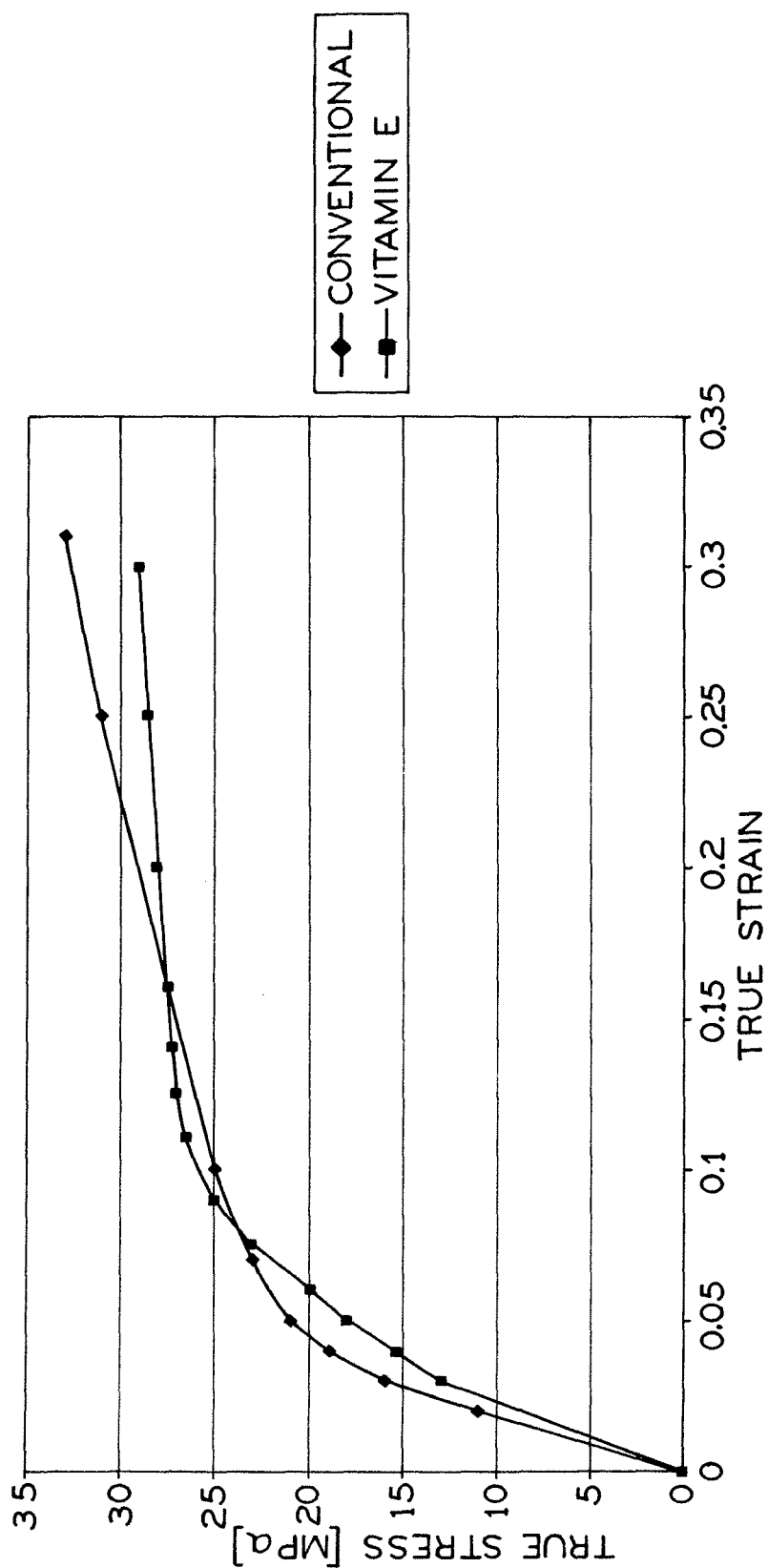
FIG. 5 depicts a graphical illustration of the stress/strain properties of different polymeric materials.

Using the previous FE model developed in Example 3 above, a porous metal and UHMWPE design using conventional UHMWPE, i.e., UHMWPE that has not been antioxidant stabilized, was compared with a porous metal and UHMWPE design using antioxidant stabilized UHMWPE, i.e., UHMWPE that incorporates an antioxidant, such as Vitamin E. The porosity of the porous metal was assumed to be 82%. Both conventional UHMWPE and antioxidant stabilized UHMWPE were modeled as multi-linear materials, as shown in FIG. 5, which indicates that the antioxidant stabilized UHMWPE has a lower elastic modulus but higher yield stress than the conventional UHMWPE. All models were simulated as under uniaxial compression and the geometry of all models was the same. Additionally, in the models, the thickness of both the conventional UHMWPE and the antioxidant stabilized UHMWPE layers was 3.5 mm and the thickness of the porous metal layer was 3.0 mm.

The stresses at the maximum stress point for both the conventional UHMWPE and the antioxidant stabilized UHMWPE were recorded during the loading process and the results are set forth in TABLE 7 below. Referring to TABLE 7, the results indicated that the overall response has less variation in the non-linear region and under compression loading. Regardless of the compression loading condition, it was shown that compressive stresses were up to 8% lower in the antioxidant stabilized UHMWPE than in the conventional UHMWPE. Additionally, shear stresses were up to 13% lower in the antioxidant stabilized UHMWPE than in the conventional UHMWPE. This indicates that under the same load condition, a porous metal/UHMWPE construct utilizing an antioxidant stabilized UHMWPE may experience less overall stress than a similar construct utilizing conventional UHMWPE. Thus, in such a construct, the antioxidant stabilized UHMWPE may have equivalent or better mechanical performance than conventional UHMWPE.

TABLE 7

Von Mises Compression [MPa]

| loading time | strain | conventional | VE |
|---|---|---|---|
| 0.00 | 0.0000 | 0.00 | 0.00 |
| 0.05 | 0.0025 | 5.20 | 4.47 |
| 0.10 | 0.0050 | 8.07 | 7.50 |
| 0.15 | 0.0075 | 10.74 | 9.33 |
| 0.20 | 0.0100 | 11.82 | 11.36 |
| 0.25 | 0.0125 | 12.93 | 12.63 |
| 0.30 | 0.0150 | 13.96 | 13.43 |
| 0.35 | 0.0175 | 14.91 | 14.16 |
| 0.40 | 0.0200 | 15.80 | 14.85 |
| 0.45 | 0.0225 | 16.56 | 15.51 |
| 0.50 | 0.0250 | 17.17 | 16.14 |
| 0.55 | 0.0275 | 17.75 | 16.74 |
| 0.60 | 0.0300 | 18.29 | 17.30 |
| 0.65 | 0.0325 | 18.74 | 17.78 |
| 0.70 | 0.0350 | 19.15 | 18.22 |
| 0.75 | 0.0375 | 19.51 | 18.62 |
| 0.80 | 0.0400 | 19.86 | 19.01 |
| 0.85 | 0.0425 | 20.22 | 19.39 |
| 0.90 | 0.0450 | 20.54 | 19.76 |
| 0.95 | 0.0475 | 20.82 | 20.08 |
| 1.00 | 0.0500 | 21.09 | 20.39 |

Example 5

Feasibility Study of α-Tocopherol Acetate

Throughout the various Examples 5-13 set forth below, irradiated UHMWPE blends (i.e., antioxidant stabilized, crosslinked UHMWPE) are used, which have been irradiated according to one of three different irradiation methods. As used in the Examples below, the term "UHMWPE blend" refers to an antioxidant stabilized UHMWPE or, if used to refer to an antioxidant stabilized UHMWPE after exposure to crosslinking irradiation, an antioxidant stabilized, crosslinked UHMWPE. As set forth above, differences in the irradiation conditions and techniques may affect the resulting material properties of the UHMWPE blend. Therefore, in order to properly analyze and compare the results set forth in the Examples and corresponding TABLES, each of the irradiated UHMWPE blends used in the Examples below are identified, where relevant, as having been irradiated according to the one of the methods set forth below in TABLE 8. Additionally, the electron beam source is calibrated by performing dosimetry at low irradiation doses and then parametrically determining the activation of the electron beam source needed to achieve higher doses. As a result, at higher irradiation doses, differences may exist between the actual dose and the parametrically determined dose, which may cause differences in the material properties of the irradiated UHMWPE blends.

TABLE 8

Irradiation Methods

| | Method A | Method B | Method C |
|---|---|---|---|
| Dose Rate (kGy-m/min) | 30-75 | 16-25 | 75-240 |
| Dose Level (kGy) | 160-190 | 133-217 | 90-200 |
| Electron Beam Energy (MeV) | 10 | 12 | 10 |
| Method of Dosimetry | Water Calorimeter | Aluminum Calorimeter | Radiochromic Film |

The feasibility of blending α-tocopherol acetate with UHMWPE was investigated. α-tocopherol acetate was obtained from DSM Nutritional Products, Ltd. of Geleen, Netherlands and medical grade UHMWPE powder GUR 1050 was obtained from Ticona, having North American headquarters located in Florence, Ky. Isopropanol was then added to the α-tocopherol acetate as a diluent and the α-tocopherol acetate was solvent blended with the UHMWPE powder. The blending continued until two different UHMWPE/α-tocopherol acetate blends were obtained, one UHMWPE blend having 0.05 wt. % α-tocopherol acetate and the other UHMWPE blend having 0.5 wt. % α-tocopherol acetate. Each of the UHMWPE blends were then compression molded to form four one-inch-thick pucks. Two pucks of each UHMWPE blend, i.e., two pucks of the UHMWPE blend having 0.05 wt. % α-tocopherol acetate and two pucks of the UHMWPE blend having 0.5 wt. % α-tocopherol acetate, were preheated to 120° C. in a Grieve convection oven, available from The Grieve Corporation of Round Lake, Ill. The pucks were held at 120° C. for 8 hours. After the expiration of 8 hours, the pucks were irradiated at 10 MeV, 50 kGy-m/min dose rate at 65 kGy and 100 kGy dose at Iotron Industries Canada Inc. located in Port Coquitlam, BC, Canada.

The remaining two pucks of each UHMWPE blend, i.e., two pucks of the UHMWPE blend having 0.05 wt. % α-tocopherol acetate and two pucks of the UHMWPE blend having 0.5 wt. % α-tocopherol acetate, were heated to 40° C. overnight. The next morning, the remaining two pucks of each UHMWPE blend were irradiated at 10 MeV, 50 kGy-m/min dose rate at 100 kGy dose at Iotron Industries Canada Inc. located in Port Coquitlam, BC, Canada.

After irradiation, all of the pucks were cut in half and a film was cut from the center of each puck. The films were then subjected to FTIR analysis using a Bruker Optics FTIR Spectrometer, available from Bruker Optics of Billerica, Mass. Both halves of each puck were then machined into flat sheets approximately ⅛ inch thick. One half of the flat sheets were immediately subjected to FTIR. The other half of the flat sheets were then subjected to accelerated aging in accordance with the American Society for Testing and Materials (ASTM) Standard F-2003, Standard Practice for Accelerated Aging of Ultra-High Molecular Weight Polyethylene after Gamma Irradiation in Air. Tensile specimens formed from the flat sheets were subjected to accelerated aging and were then subjected to FTIR analysis. The OI and wt. % of α-tocopherol acetate were determined from the FTIR results, set forth in TABLE 9, below, and in FIG. 14. However, there were interference peaks in the FTIR results that prevented measurement of OI for the 0.5 wt. %, 65 kGy, unaged sample.

TABLE 9

FTIR Results

| wt. % tocopherol | Dose, kGy | Condition | OI | wt. % tocopherol, meas. |
|---|---|---|---|---|
| 0.50 | 100 | Un-aged | <0/<0 | 0.17/0.15 |
|  |  | Aged | 0.0323 | 0.15 |
| 0.50 | 65 | Un-aged | *interference* | 0.14/0.15 |
|  |  | Aged | 0.0083 | 0.14 |
| 0.05 | 100 | Un-aged | 0.0300/0.0948 | 0.01/0.00 |
|  |  | Aged | 0.0647 | <0 |
| 0.05 | 65 | Un-aged | 0.0376/0.0940 | 0.02/0.00 |
|  |  | Aged | 0.0647 | <0 |

The FTIR results revealed that the OI of the UHMWPE blend having 0.05 wt. % α-tocopherol acetate was generally higher than the OI of the UHMWPE blend having 0.50 wt. % α-tocopherol acetate. This is believed to be because these samples still contained α-tocopherol acetate after irradiation. As a result, the α-tocopherol acetate was still available in these samples to react with free radicals and reduce the oxidative degradation of the UHMWPE blend. Additionally, the FTIR results showed that virtually no α-tocopherol acetate was left after irradiation of the UHMWPE blend having 0.05 wt. % α-tocopherol acetate and that about one-third of the α-tocopherol acetate was left after irradiation of the UHMWPE blend having 0.5 wt. % α-tocopherol acetate. Further, as shown in TABLE 10 below, tensile properties were similar for both the UHMWPE blends that were subjected to accelerated aging and the UHMWPE blends that were not subjected to accelerated aging. Finally, the FTIR results suggested that the UHMWPE blends containing α-tocopherol acetate have similar stabilization properties, i.e., a similar ability to prevent oxidative degeneration, as UHMWPE blends containing similar concentration of d,l-α-tocopherol.

TABLE 10

Mechanical Properties

| wt. % α-tocopherol acetate | Dose, kGy (Temperature) | Condition | Elongation, % | Yield, MPa | UTS, MPa |
|---|---|---|---|---|---|
| 0.50 | 100 (40° C.) | Un-aged | 356.7 | 23.1 | 61.7 |
|  |  | Aged | 360.1 | 25.3 | 65.3 |
| 0.50 | 65 (120° C.) | Un-aged | 384.6 | 21.8 | 61.4 |
|  |  | Aged | 378.4 | 24.2 | 65.1 |
| 0.05 | 100 (40° C.) | Un-aged | 342.9 | 21.5 | 56.7 |
|  |  | Aged | 288.6 | 25.2 | 61.0 |
| 0.05 | 65 (120° C.) | Un-aged | 352.4 | 21.4 | 57.4 |
|  |  | Aged | 287.7 | 25.2 | 59.6 |

Example 6

Chemical Properties of UHMWPE Blended with Tocopherol

The chemical properties of d/l-α-tocopherol mechanically blended with a UHMWPE powder which was slab molded into bars and electron beam irradiated were investigated. To perform this investigation, Design Expert 6.0.10 software, obtained from Stat-Ease, Inc. Minneapolis, Minn., was utilized to setup a modified fractional factorial Design of Experiment (DOE). The DOE evaluated five different variables: UHMWPE resin type, wt. % of d/l-α-tocopherol, preheat temperature, dose rate, and irradiation dose.

GUR 1050 and GUR 1020 medical grade UHMWPE powders were obtained from Ticona, having North American headquarters in Florence, Ky. d/l-α-tocopherol was obtained from DSM Nutritional Products, Ltd. of Geleen, Netherlands. The GUR 1050 and GUR 1020 were separately mechanically blended with the d/l-α-tocopherol by low intensity blending using a Diosna P100 Granulator, available from Diosna GmbH of Osnabrück, Germany, a subsidiary of Multimixing S.A. Both the GUR 1050 and the GUR 1020 resins were mixed with the d/l-α-tocopherol in several batches to create UHMWPE blends of both resin types having 0.2 wt. %, 0.5 wt. %, and 1.0 wt. % d/l-α-tocopherol. Each batch of blended material was compression molded into a slab and cut into bars of various sizes. Each of the resulting bars was then preheated by heating to a preheat temperature in a Grieve convection oven, available from The Grieve Corporation of Round Lake, Ill. The preheat temperature was selected from 40° C., 100° C., 110° C. and 122.2° C., as set forth in TABLE 11 below.

After the preheating, the UHMWPE blend bars were electron beam irradiated according to Method C, set forth in TABLE 8 above, at a selected dose rate until a selected total irradiation dose was administered. The dose rate was selected from 75 kGy-m/min, 155 kGy-m/min, and 240 kGy-m/min and the total irradiation dose was selected from 90 kGy, 120 kGy, 150 kGy, and 200 kGy. The portion of each bar was then microtomed into 200 micron thick films. These films were then subjected to FTIR analysis on a Bruker Optics FTIR spectrometer, available from Bruker Optics of Billerica, Mass. The FTIR results were analyzed to determine the VEI, wt. % d/l-α-tocopherol, the OI, and the TVI. The VEI and wt. % d/l-α-tocopherol were determined by calculating the ratio of the area under the d/l-α-tocopherol peak at 1275-1245 $cm^{-1}$ on the resulting FTIR chart to the area under the polyethylene peak at 1392-1330 $cm^{-1}$ and at 1985-1850 $cm^{-1}$. The OI was determined by calculating the ratio of the area under the carbonyl peak on the FTIR chart at 1765-1680 $cm^{-1}$ to the area of the polyethylene peak at 1392-1330 $cm^{-1}$. The TVI was determined by calculating the ratio of the area on the FTIR chart under the vinyl peak at 980-947 $cm^{-1}$ to the area under the polyethylene peak at 1392-1330 $cm^{-1}$.

After the initial VEI, wt. % d/l-α-tocopherol and TVI were determined from the FTIR analysis of the thin films, each of the thin films were accelerated aged according to ASTM Standard F-2003, Standard Practice for Accelerated Aging of Ultra-High Molecular Weight Polyethylene after Gamma Irradiation in Air. The accelerated aged films were again subjected to FTIR analysis on a Bruker Optics FTIR spectrometer, available from Bruker Optics of Billerica, Mass. The resulting FTIR charts were analyzed to determine VEI, wt. % d/l-α-tocopherol, OI, and TVI according to the methods set forth above. Once subjected to FTIR analysis, the aged files were placed in boiling hexane and allowed to remain there for 24 hours to extract the d/l-α-tocopherol. After extraction of the d/l-α-tocopherol, the aged films were again subjected to FTIR analysis on the Bruker Optics FTIR spectrometer. The resulting FTIR chart was then analyzed to determine the OI in accordance with the method set forth above. The additional FTIR analysis was performed to eliminate the d/l-α-tocopherol peak from interfering with the oxidation peaks. An analysis of the results set forth in TABLE 11 below indicate that selecting a warmer preheat temperature may result in a lower OI and may also result in some of the d/l-α-tocopherol remaining in the UHMWPE after irradiation.

TABLE 11

FTIR Results of Irradiated UHMWPE Blended with d/l-α-tocopherol

| Run | Pre-heat (° C.) | Dose (kGy) | VE level (° C.) | Dose Rate (kGy-m/min) | Resin Type (GUR) |
|---|---|---|---|---|---|
| 1 | 122 | 150 | 1 | 75 | 1020 |
| 2 | 40 | 200 | 0.2 | 155 | 1020 |
| 3 | 122 | 90 | 0.5 | 75 | 1020 |
| 4 | 122 | 200 | 0.2 | 155 | 1020 |
| 5 | 40 | 90 | 0.2 | 240 | 1050 |
| 6 | 122 | 90 | 0.2 | 75 | 1050 |
| 7 | 40 | 150 | 0.2 | 75 | 1050 |
| 8 | 122 | 150 | 0.2 | 75 | 1020 |
| 9 | 40 | 90 | 1 | 240 | 1050 |
| 10 | 40 | 200 | 0.5 | 155 | 1020 |
| 11 | 122 | 90 | 0.2 | 240 | 1020 |
| 12 | 40 | 90 | 1 | 75 | 1020 |
| 13 | 40 | 150 | 0.5 | 75 | 1020 |
| 14 | 122 | 150 | 0.2 | 240 | 1050 |
| 15 | 122 | 150 | 0.5 | 240 | 1020 |
| 16 | 40 | 150 | 0.2 | 240 | 1020 |
| 17 | 40 | 90 | 0.2 | 75 | 1020 |
| 18 | 122 | 200 | 0.5 | 155 | 1020 |
| 19 | 122 | 90 | 1 | 240 | 1020 |
| 20 | 40 | 150 | 1 | 240 | 1020 |
| 21 | 40 | 200 | 1 | 155 | 1020 |
| 22 | 122 | 200 | 1 | 155 | 1020 |
| 23 | 40 | 200 | 0.2 | 155 | 1050 |
| 24 | 122 | 200 | 0.2 | 155 | 1050 |
| 25 | 40 | 200 | 0.5 | 155 | 1050 |
| 26 | 122 | 200 | 0.5 | 155 | 1050 |
| 27 | 40 | 200 | 1 | 155 | 1050 |
| 28 | 122 | 200 | 1 | 155 | 1050 |
| 29 | 40 | 120 | 0.5 | 157.5 | 1050 |
| 30 | 122 | 120 | 0.5 | 157.5 | 1050 |
| 31 | 40 | 120 | 1 | 157.5 | 1050 |
| 32 | 122 | 120 | 1 | 157.5 | 1050 |
| 33 | 40 | 90 | 1 | 75 | 1050 |
| 34 | 122 | 90 | 0.5 | 75 | 1050 |
| 35 | 40 | 150 | 0.5 | 75 | 1050 |
| 36 | 122 | 150 | 1 | 75 | 1050 |
| 37 | 40 | 90 | 0.5 | 240 | 1050 |
| 38 | 122 | 90 | 1 | 240 | 1050 |
| 39 | 40 | 150 | 1 | 240 | 1050 |
| 40 | 122 | 150 | 0.5 | 240 | 1050 |

TABLE 11-continued

FTIR Results of Irradiated UHMWPE Blended with d/l-α-tocopherol

| Run | VE % 1370 nm IR peak | VE % 1900 nm IR peak | VE Index 1370 nm IR peak | VE Index 1900 nm IR peak | VE % (aged) 1370 nm IR peak |
|---|---|---|---|---|---|
| 1 | 0.803 | 0.682 | 0.046 | 0.171 | 0.493 |
| 2 | 0.040 | 0.048 | 0.004 | 0.015 | 0.022 |
| 3 | 0.359 | 0.321 | 0.021 | 0.082 | 0.248 |
| 4 | 0.045 | 0.054 | 0.004 | 0.016 | 0.037 |
| 5 | 0.047 | 0.055 | 0.004 | 0.016 | 0.063 |
| 6 | 0.061 | 0.071 | 0.005 | 0.020 | 0.073 |
| 7 | 0.011 | 0.025 | 0.003 | 0.009 | 0.017 |
| 8 | 0.031 | 0.042 | 0.004 | 0.013 | 0.033 |
| 9 | 0.194 | 0.165 | 0.012 | 0.044 | 0.272 |
| 10 | 0.731 | 0.626 | 0.042 | 0.157 | 0.545 |
| 11 | 0.075 | 0.078 | 0.006 | 0.022 | 0.081 |
| 12 | 0.882 | 0.738 | 0.050 | 0.185 | 0.417 |
| 13 | 0.286 | 0.222 | 0.017 | 0.058 | 0.274 |
| 14 | 0.058 | 0.072 | 0.005 | 0.021 | 0.056 |
| 15 | 0.162 | 0.151 | 0.011 | 0.040 | 0.279 |
| 16 | 0.051 | 0.053 | 0.005 | 0.016 | 0.050 |
| 17 | 0.078 | 0.076 | 0.006 | 0.022 | 0.044 |
| 18 | 0.721 | 0.634 | 0.041 | 0.159 | 0.524 |
| 19 | 0.769 | 0.688 | 0.044 | 0.173 | 0.430 |
| 20 | 0.781 | 0.597 | 0.044 | 0.150 | 0.531 |
| 21 | 0.769 | 0.591 | 0.044 | 0.149 | 0.560 |
| 22 | 0.765 | 0.607 | 0.044 | 0.153 | 0.575 |
| 23 | 0.028 | 0.034 | 0.003 | 0.011 | 0.016 |
| 24 | 0.051 | 0.053 | 0.005 | 0.016 | 0.041 |
| 25 | 0.288 | 0.249 | 0.018 | 0.064 | 0.281 |
| 26 | 0.320 | 0.282 | 0.019 | 0.073 | 0.309 |
| 27 | 0.284 | 0.222 | 0.017 | 0.058 | 0.281 |
| 28 | 0.308 | 0.241 | 0.019 | 0.062 | 0.295 |
| 29 | 0.613 | 0.550 | 0.035 | 0.139 | 0.489 |
| 30 | 0.753 | 0.700 | 0.043 | 0.176 | 0.445 |
| 31 | 0.283 | 0.240 | 0.017 | 0.062 | 0.279 |
| 32 | 0.306 | 0.288 | 0.019 | 0.074 | 0.259 |
| 33 | 0.779 | 0.706 | 0.044 | 0.177 | 0.429 |
| 34 | 0.328 | 0.314 | 0.020 | 0.080 | 0.209 |
| 35 | 0.143 | 0.125 | 0.010 | 0.034 | 0.247 |
| 36 | 0.803 | 0.758 | 0.046 | 0.190 | 0.442 |
| 37 | 0.332 | 0.291 | 0.020 | 0.075 | 0.262 |
| 38 | 0.741 | 0.731 | 0.042 | 0.183 | 0.390 |
| 39 | 0.790 | 0.658 | 0.045 | 0.165 | 0.524 |
| 40 | 0.327 | 0.301 | 0.020 | 0.077 | 0.282 |

| Run | VE % (aged) 1900 nm IR peak | VE Index (aged) 1370 nm IR peak | VE Index (aged) 1900 nm IR peak | OI (Extraction-aged) FTIR | TVI FTIR | TVI (aged) FTIR |
|---|---|---|---|---|---|---|
| 1 | 0.425 | 0.029 | 0.108 | −0.010 | 0.061 | 0.062 |
| 2 | 0.033 | 0.003 | 0.011 | 0.078 | 0.073 | 0.072 |
| 3 | 0.226 | 0.015 | 0.059 | −0.008 | 0.046 | 0.052 |
| 4 | 0.048 | 0.004 | 0.015 | 0.025 | 0.081 | 0.082 |
| 5 | 0.068 | 0.005 | 0.020 | 0.039 | 0.039 | 0.040 |
| 6 | 0.080 | 0.006 | 0.023 | 0.000 | 0.054 | 0.048 |
| 7 | 0.029 | 0.003 | 0.010 | 0.086 | 0.068 | 0.064 |
| 8 | 0.042 | 0.004 | 0.013 | 0.035 | 0.076 | 0.074 |
| 9 | 0.231 | 0.017 | 0.060 | 0.011 | 0.048 | 0.040 |
| 10 | 0.468 | 0.032 | 0.118 | 0.005 | 0.076 | 0.077 |
| 11 | 0.084 | 0.006 | 0.024 | 0.007 | 0.055 | 0.054 |
| 12 | 0.359 | 0.025 | 0.091 | −0.001 | 0.034 | 0.035 |
| 13 | 0.211 | 0.017 | 0.055 | 0.082 | 0.075 | 0.074 |
| 14 | 0.070 | 0.005 | 0.020 | 0.001 | 0.072 | 0.072 |
| 15 | 0.244 | 0.017 | 0.063 | 0.025 | 0.081 | 0.084 |
| 16 | 0.052 | 0.005 | 0.016 | 0.075 | 0.063 | 0.062 |
| 17 | 0.048 | 0.004 | 0.015 | 0.098 | 0.045 | 0.045 |
| 18 | 0.458 | 0.030 | 0.116 | −0.004 | 0.083 | 0.085 |
| 19 | 0.392 | 0.025 | 0.100 | −0.010 | 0.041 | 0.047 |
| 20 | 0.409 | 0.031 | 0.104 | 0.087 | 0.080 | 0.078 |
| 21 | 0.429 | 0.032 | 0.109 | 0.061 | 0.081 | 0.087 |
| 22 | 0.457 | 0.033 | 0.116 | −0.007 | 0.092 | 0.091 |
| 23 | 0.025 | 0.003 | 0.009 | 0.120 | 0.078 | 0.079 |
| 24 | 0.045 | 0.004 | 0.014 | 0.032 | 0.084 | 0.085 |
| 25 | 0.241 | 0.017 | 0.062 | 0.009 | 0.075 | 0.073 |
| 26 | 0.268 | 0.019 | 0.069 | −0.002 | 0.085 | 0.083 |
| 27 | 0.220 | 0.017 | 0.057 | 0.024 | 0.080 | 0.079 |

TABLE 11-continued

FTIR Results of Irradiated UHMWPE Blended with d/l-α-tocopherol

| 28 | 0.229 | 0.018 | 0.059 | 0.042  | 0.094 | 0.096 |
|----|-------|-------|-------|--------|-------|-------|
| 29 | 0.429 | 0.028 | 0.109 | 0.040  | 0.053 | 0.058 |
| 30 | 0.421 | 0.026 | 0.107 | 0.000  | 0.063 | 0.064 |
| 31 | 0.236 | 0.017 | 0.061 | 0.063  | 0.061 | 0.061 |
| 32 | 0.244 | 0.016 | 0.063 | 0.004  | 0.065 | 0.066 |
| 33 | 0.397 | 0.025 | 0.101 | 0.036  | 0.040 | 0.041 |
| 34 | 0.205 | 0.013 | 0.053 | −0.005 | 0.049 | 0.051 |
| 35 | 0.211 | 0.015 | 0.055 | 0.067  | 0.072 | 0.068 |
| 36 | 0.423 | 0.026 | 0.107 | −0.012 | 0.055 | 0.058 |
| 37 | 0.234 | 0.016 | 0.061 | 0.029  | 0.041 | 0.048 |
| 38 | 0.391 | 0.023 | 0.099 | −0.004 | 0.038 | 0.042 |
| 39 | 0.440 | 0.030 | 0.111 | 0.043  | 0.073 | 0.076 |
| 40 | 0.262 | 0.017 | 0.068 | −0.004 | 0.068 | 0.068 |

Example 7

Mechanical Properties of UHMWPE Blended with d/l-α-Tocopherol

The mechanical properties of d/l-α-tocopherol mechanically blended with a UHMWPE powder which was slab molded into bars and electron beam irradiated were investigated. To perform this investigation, Design Expert 6.0.10 software, obtained from Stat-Ease, Inc. Minneapolis, Minn., was utilized to setup a modified fractional factorial Design of Experiment (DOE). The DOE evaluated five different variables: UHMWPE resin type, weight percent of d/l-α-tocopherol, preheat temperature, dose rate, and irradiation dose.

GUR 1050 and GUR 1020 medical grade UHMWPE powders were obtained from Ticona, having North American headquarters in Florence, Ky. d/l-α-tocopherol was obtained from DSM Nutritional Products, Ltd. of Geleen, Netherlands. The GUR 1050 and GUR 1020 were separately mechanically blended with the d/l-α-tocopherol by low intensity blending using a Diosna P100 Granulator, available from Diosna GmbH of Osnabrück, Germany, a subsidiary of Multimixing S.A. Both the GUR 1050 and the GUR 1020 resins were mixed with the d/l-α-tocopherol in several batches to create UHMWPE blends of both resin types having 0.2 wt. %, 0.5 wt. %, and 1.0 wt. % d/l-α-tocopherol. Each batch of blended material was compression molded into a slab and cut into bars. Each of the resulting bars was then preheated by heating the bars in a Grieve convection oven, available from The Grieve Corporation of Round Lake, Ill., to a preheat temperature. The preheat temperature was selected from 40° C., 100° C., 110° C. and 122.2° C., as set forth in TABLE 12 below.

After being preheated, the UHMWPE blend bars were electron beam irradiated according to Method C, set forth in TABLE 8 above, at a selected dose rate until a selected total irradiation dose was administered. The dose rate was selected from 75 kGy-m/min, 155 kGy-m/min, and 240 kGy-m/min and the total irradiation dose was selected from 90 kGy, 120 kGy, 150 kGy, 200 kGy, and 250 kGy. Type V tensile specimens, as defined by the American Society for Testing and Materials (ASTM) Standard D638, Standard Test Method for Tensile Properties of Plastics, were machined from each of the UHMWPE blend bars. The Type V tensile specimens were then subjected to ultimate tensile elongation, UTS, and YS testing in accordance with ASTM Standard D638. Izod specimens were also machined from each of the UHMWPE blend bars and tested for izod impact strength according to ASTM Standard D256, Standard Test Methods for Determining the Izod Pendulum Impact Resistance of Plastics. Dynamic mechanical analysis (DMA) specimens were also machined from each of the UHMWPE blend bars and tested using a Model DMA 2980 Dynamic Mechanical Analyzer from TA Instruments of New Castle, Del.

An analysis of the results indicates that the total irradiation dose had an influence on the izod impact strength, ultimate tensile elongation, and yield strength of the UHMWPE blends. Additionally, the preheat temperature had an influence on the ultimate tensile strength and yield strength. In contrast, the weight percent of d/l-α-tocopherol had an influence on ultimate tensile elongation and the dynamic mechanical analysis. Additional results from the testing are set forth below in TABLE 12, below.

TABLE 12

Mechanical Properties of UHMWPE Blended with d/l-α-tocopherol

| Std | Preheat ° C. | Dose kGy | VE Conc. | Dose Rate kGy-m/min | Resin | Izod kJ/m^2 | Elongation % | UTS MPa | YS MPa | DMA MPa |
|-----|--------------|----------|----------|---------------------|-------|-------------|--------------|---------|--------|---------|
| 1  | 40    | 90  | 0.2 | 75    | 1020 | 90.79  | Not Tested |       |       | 5.45 |
| 2  | 122.2 | 90  | 0.2 | 75    | 1050 | 74.8   | 348.8      | 50.38 | 21.72 | 6.12 |
| 3  | 40    | 150 | 0.2 | 75    | 1050 | 59.66  | 300.9      | 56.2  | 25.1  | 6.78 |
| 4  | 100   | 150 | 0.2 | 75    | 1020 | 66.05  | 314.8      | 52.42 | 25.24 | 5.76 |
| 5  | 40    | 90  | 1   | 75    | 1020 | 111.19 | Not Tested |       |       | 4.36 |
| 6  | 122.2 | 90  | 0.5 | 75    | 1020 | 91.55  | Not Tested |       |       | 5.1  |
| 7  | 40    | 150 | 0.5 | 75    | 1020 | 79.96  | 355.7      | 55.83 | 26.28 | 4.96 |
| 8  | 100   | 150 | 1   | 75    | 1020 | 81.25  | Not Tested |       |       | 4.78 |
| 9  | 40    | 90  | 0.2 | 240   | 1050 | 82.01  | 319.3      | 56.83 | 23.06 | 6.18 |
| 10 | 122.2 | 90  | 0.2 | 240   | 1020 | 84.5   | Not Tested |       |       | 5.43 |
| 11 | 40    | 150 | 0.2 | 240   | 1020 | 67.53  | 293.1      | 56.19 | 26.87 | 5.96 |
| 12 | 100   | 150 | 0.2 | 240   | 1050 | 67.75  | 307.2      | 52.95 | 25.21 | 6.31 |
| 13 | 40    | 90  | 1   | 240   | 1050 | 106.17 | 411.2      | 61.76 | 24.89 | 4.53 |
| 14 | 122.2 | 90  | 1   | 240   | 1020 | 94.66  | Not Tested |       |       | 4.83 |
| 15 | 40    | 150 | 1   | 240   | 1020 | 93.79  | Not Tested |       |       | 5.6  |
| 16 | 100   | 150 | 0.5 | 240   | 1020 | 73.08  | 342.2      | 51.54 | 23.39 | 5.22 |
| 17 | 40    | 120 | 0.5 | 157.5 | 1050 | 99.87  | 374.6      | 57.96 | 23.23 | 5.06 |
| 18 | 110   | 120 | 0.5 | 157.5 | 1050 | 90.67  | 363.6      | 50.97 | 22.15 | 5.42 |
| 19 | 40    | 120 | 1   | 157.5 | 1050 | 94.34  | 352.5      | 58.5  | 23.64 | 5.53 |
| 20 | 110   | 120 | 1   | 157.5 | 1050 | 85.01  | 344.9      | 48.98 | 21.95 | 5.72 |
| 21 | 40    | 90  | 1   | 75    | 1050 | 107.07 | 396.4      | 61.25 | 23.13 | 5.02 |
| 22 | 122.2 | 90  | 0.5 | 75    | 1050 | 93.44  | 375.8      | 51.47 | 21.92 | 5.7  |
| 23 | 40    | 150 | 0.5 | 75    | 1050 | 82.09  | 330.4      | 56.65 | 25.78 | 4.62 |
| 24 | 100   | 150 | 1   | 75    | 1050 | 88.28  | Not Tested |       |       | 5.4  |
| 25 | 40    | 90  | 0.5 | 240   | 1050 | 102.39 | 36.9       | 58.4  | 23.31 | 5.16 |

TABLE 12-continued

Mechanical Properties of UHMWPE Blended with d/l-α-tocopherol

| Std | Preheat °C. | Dose kGy | VE Conc. | Dose Rate kGy-m/min | Resin | Izod kJ/m^2 | Elongation % | UTS MPa | YS MPa | DMA MPa |
|---|---|---|---|---|---|---|---|---|---|---|
| 26 | 122.2 | 90 | 1 | 240 | 1050 | 96.6 | 381.9 | 50.3 | 21.29 | 5.44 |
| 27 | 40 | 150 | 1 | 240 | 1050 | 89.5 | Not Tested | | | 5.16 |
| 28 | 100 | 150 | 0.5 | 240 | 1050 | 78.51 | 332.9 | 50.18 | 22.08 | 5.6 |
| 29 | 40 | 200 | 0.2 | 155 | 1020 | 55.98 | 246.2 | 52.37 | 27.23 | 6.32 |
| 30 | 110 | 200 | 0.2 | 155 | 1020 | 52.98 | 268.4 | 48.28 | 24.82 | 6.05 |
| 31 | 40 | 200 | 0.5 | 155 | 1020 | 74.64 | 310.7 | 53.53 | 25.42 | 5.38 |
| 32 | 110 | 200 | 0.5 | 155 | 1020 | 65.47 | 309.1 | 49.13 | 24.21 | 5.31 |
| 33 | 40 | 200 | 1 | 155 | 1020 | 72.67 | 362.9 | 55.62 | 25.9 | 4.63 |
| 34 | 110 | 200 | 1 | 155 | 1020 | 66.62 | 349.7 | 50.45 | 24.24 | 4.93 |
| 35 | 40 | 200 | 0.2 | 155 | 1050 | 57.82 | 226.4 | 50.92 | 25.3 | 7.15 |
| 36 | 110 | 200 | 0.2 | 155 | 1050 | 59.04 | 259.4 | 46.4 | 23.7 | 6.57 |
| 37 | 40 | 200 | 0.5 | 155 | 1050 | 67.49 | 280.6 | 51.91 | 26.23 | 5.88 |
| 38 | 110 | 200 | 0.5 | 155 | 1050 | 64.6 | 304.8 | 51.23 | 25.14 | 5.7 |
| 39 | 40 | 200 | 1 | 155 | 1050 | 82.01 | 328.9 | 53.79 | 24.43 | 5.15 |
| 40 | 110 | 200 | 1 | 155 | 1050 | 69.42 | 329.7 | 49.54 | 23.12 | 5.27 |
| 41 | 100 | 150 | 0.2 | 240 | 1050 | Not Tested | 307.2 | 52.96 | 23.27 | Not Tested |
| 42 | 100 | 150 | 0.2 | 240 | 1020 | Not Tested | 288.6 | 49.28 | 23.35 | Not Tested |

Example 8

Wear Properties of UHMWPE Mixed with d,l-α-Tocopherol

The wear properties of UHMWPE mechanically blended with d/l-α-tocopherol and exposed to electron beam irradiation was investigated. To perform this investigation, Design Expert 6.0.10 software, obtained from Stat-Ease, Inc. Minneapolis, Minn., was utilized to setup a modified central composite Design of Experiment (DOE). The DOE evaluated five different variables: preheat temperature, dose rate, total dose administered, d,l-α-tocopherol concentration, and cooling period, i.e., the elapsed time from end of the preheat until initial exposure to irradiation.

GUR 1050 medical grade UHMWPE powder was obtained from Ticona, having North American headquarters in Florence, Ky. d/l-α-tocopherol was obtained from DSM Nutritional Products, Ltd of Geleen, Netherlands. The GUR 1050 was mechanically mixed with the d/l-α-tocopherol using a High Intensity Mixer, available from Eirich Machines of Gurnee, Ill. The GUR 1050 resin was mixed with the d/l-α-tocopherol in several batches to create UHMWPE blends having a selected wt. % of d/l-α-tocopherol. The wt. % of d/l-α-tocopherol was selected from 0.14 wt. %, 0.19 wt. %, and 0.24 wt. % d/l-α-tocopherol. Each of the blends were then consolidated and formed into 2.5 inch diameter and 1 inch thick pucks. Each of the resulting pucks was then preheated by heating the pucks in a Grieve convection oven, available from The Grieve Corporation of Round Lake, Ill., to a preheat temperature. The preheat temperature was selected from 85° C., 100° C., and 115° C., as set forth in TABLE 13 below.

After being preheated, the UHMWPE blend pucks were then removed from the convection oven for a cooling period. The cooling period was selected from 7 minutes, 14 minutes, and 21 minutes, as set forth in TABLE 13 below. The pucks were then electron beam irradiated according to Method A, set forth in TABLE 8 above, at a selected dose rate until a selected total irradiation dose was administered. The dose rate was selected from 30 kGy-m/min, 52.5 kGy-m/min, and 75 kGy-m/min and the total irradiation dose was selected from 160 kGy, 175 kGy, and 190 kGy.

Pin-on-disc (POD) specimens in the form cylinders having a 9 mm diameter and 13 mm thickness were then machined from the UHMWPE blend pucks. A bidirectional pin-on-disc wear tester was then used to measure the wear rate of UHMWPE pins articulating against polished cobalt-chrome discs lubricated by 100% bovine serum. These measurements were made in accordance with the teachings of Bragdon, C. R., et al., in *A new pin-on-disk wear testing method for simulating wear of polyethylene on cobalt-chrome alloy in total hip arthroplasty*, published in the Journal of Arthroplasty, Vol. 16, Issue 5, 2001, on pages 658-65, the entire disclosure of which is expressly incorporated by reference herein. The bidirectional motion for the pin-on-disc wear tester was generated by a computer controlled XY table, available from the Compumotor Division of Parker Hannifin of Cleveland, Ohio, which was programmed to move in a 10 mm by 5 mm rectangular pattern. Affixed atop the XY table was a basin containing six cobalt-chrome discs polished to an implant quality finish. The XY table and basin were mounted on a servo-hydraulic MTS machine, available from MTS of Eden Prairie, Minn. The MTS machine then loaded the UHMWPE blend pin specimens against the polished cobalt-chrome discs.

The MTS machine was programmed to produce a Paul-type curve in synchronization with the motion of the XY table. A Paul-type curve is explained in detail in *Forces Transmitted By Joints in the Human Body* by J. P. Paul and published by in the Proceedings Institution of Mechanical Engineers at Vol. 181, Part 37, pages 8-15, the entire disclosure of which is expressly incorporated by reference herein. The peak load of the Paul-type loading curve corresponded to a peak contact pressure of 6.5 MPa between each of the UHMWPE pin specimens and the cobalt-chrome discs. Tests were conducted at 2 Hz to a total of $1.128 \times 10^6$ cycles. Analysis of the results indicated that the wear properties are affected by both the concentration of d/l-α-tocopherol and the total irradiation dose. Specifically, the results indicated that increasing the d/l-α-tocopherol concentration increased the wear rate of the UHMWPE blends, while increasing the total irradiation dose decreased the wear rate of the UHMWPE blends. Additionally, the results indicated that both dose rate and the cooling period had substantially no impact on the wear rate of the UHMWPE.

TABLE 13

Wear Properties of UHMWPE Mixed with d/l-α-tocopherol

| Run | Block | Preheat (° C.) | Dose (kGy) | VE % | Dose Rate (kGy-m/min.) | Oven to Beam (minutes) | POD Wear (mg/Mc) |
|---|---|---|---|---|---|---|---|
| 1 | Block 1 | 85 | 190 | 0.11 | 30 | 7 | 0.96 |
| 2 | Block 1 | 115 | 190 | 0.11 | 30 | 7 | 1.14 |
| 3 | Block 1 | 115 | 190 | 0.11 | 30 | 21 | 0.76 |
| 4 | Block 1 | 85 | 190 | 0.11 | 30 | 21 | 0.81 |
| 5 | Block 1 | 115 | 160 | 0.11 | 30 | 7 | 1.86 |
| 6 | Block 1 | 85 | 160 | 0.11 | 30 | 7 | 1.37 |
| 7 | Block 1 | 115 | 160 | 0.11 | 30 | 21 | 1.53 |
| 8 | Block 1 | 85 | 160 | 0.11 | 30 | 21 | 1.57 |
| 9 | Block 1 | 85 | 160 | 0.22 | 75 | 7 | 2.94 |
| 10 | Block 1 | 115 | 160 | 0.22 | 75 | 7 | 2.15 |
| 11 | Block 1 | 85 | 160 | 0.22 | 75 | 21 | 2.41 |
| 12 | Block 1 | 115 | 160 | 0.22 | 75 | 21 | 1.96 |
| 13 | Block 1 | 115 | 190 | 0.22 | 75 | 7 | 2.57 |
| 14 | Block 1 | 85 | 190 | 0.22 | 75 | 7 | 1.87 |
| 15 | Block 1 | 115 | 190 | 0.22 | 75 | 21 | 1.87 |
| 16 | Block 1 | 85 | 190 | 0.22 | 75 | 21 | 2.24 |
| 17 | Block 1 | 100 | 175 | 0.165 | 52.5 | 14 | 0.89 |
| 18 | Block 1 | 100 | 175 | 0.165 | 52.5 | 14 | 1.18 |
| 19 | Block 1 | 100 | 175 | 0.165 | 52.5 | 14 | 1.24 |
| 20 | Block 1 | 100 | 175 | 0.165 | 52.5 | 14 | 1.27 |

Example 9

Temperature Variations at the UHMWPE Blend/Substrate Interface

GUR 1050 medical grade UHMWPE powder was obtained from Ticona, having North American headquarters in Florence, Ky. d/l-α-tocopherol was obtained from DSM Nutritional Products, Ltd of Geleen, Netherlands. The GUR 1050 was mechanically blended with the d/l-α-tocopherol using a High Intensity Mixer, available from Eirich Machines of Gurnee, Ill. The GUR 1050 resin was mixed with the d/l-α-tocopherol to create a UHMWPE blend having 0.2 wt. % d/l-α-tocopherol.

A portion of the UHMWPE blend was then compression molded into a block. Another portion of the UHMWPE blend was compression molded into a substrate to create a preform. The substrate was a 70 mm diameter porous metal substrate in the form of a near-net shape acetabular shell. The porous metal substrate was produced using Trabecular Metal™ technology generally available from Zimmer, Inc., of Warsaw, Ind., and described in detail above. This process was repeated to create five different preforms. The preforms were then individually heated to a preheat temperature in a Grieve convection oven, available from The Grieve Corporation of Round Lake, Ill. The preheat temperature was selected from 100° C., 120° C., and 125° C. Once heated to the selected preheat temperature, the preforms were irradiated using Method B, set forth in TABLE 8 above, until a total irradiation dose was received. The total irradiation dose was selected from 50 kGy, 75 kGy, and 150 kGy. Additionally, the UHMWPE block was heated to a preheat temperature of 100° C. and irradiated using Method B until a total irradiation dose of 150 kGy was received by the UHMWPE block.

The temperature of the preforms was measured at the UHMWPE blend/substrate interface, at a point in the UHMWPE blend adjacent to the UHMWPE blend/substrate interface, and at a point in the center of the UHMWPE blend. Each of the temperature measures were taken using a Type J thermocouple. Additionally, the temperature at the center of the UHMWPE blend block was also measured using a Type J thermocouple. Based on the results, the presence of a porous substrate resulted in higher temperature readings in the UHMWPE blend. This is likely a result of substrate reaching a higher maximum temperature than the UHMWPE during irradiation.

Example 10

Effect of Substrate Orientation on UHMWPE Blend

GUR 1050 medical grade UHMWPE powder was obtained from Ticona, having North American headquarters in Florence, Ky. d/l-α-tocopherol was obtained from DSM Nutritional Products, Ltd of Geleen, Netherlands. The GUR 1050 was mechanically blended with the d/l-α-tocopherol using a High Intensity Mixer, available from Eirich Machines of Gurnee, Ill. The GUR 1050 resin was mixed with the d/l-α-tocopherol to create a UHMWPE blend having 0.5 wt. % d/l-α-tocopherol.

A portion of the UHMWPE blend was compression molded into a substrate to create a preform. The substrate was a 70 mm diameter porous metal substrate in the form of a near-net shape acetabular shell. The porous metal substrate was produced using Trabecular Metal™ technology generally available from Zimmer, Inc., of Warsaw, Ind., and described in detail above. This process was repeated to create three different preforms. The preforms were then heated in a convection oven to a preheat temperature of 110° C. for a minimum of 12 hours. Two of the preforms were then irradiated using Method A, as set forth in TABLE 8 above, with the substrate of one of the preforms facing the irradiation source and the substrate of the other preform facing away from the irradiation source. With the preforms in these positions, they were exposed to a first, 100 kGy dose of irradiation. The preforms were then allowed to sit in ambient air for 20 minutes. After the expiration of 20 minutes, the preforms were exposed to a second, 100 kGy dose of irradiation, for a total irradiation dose of 200 kGy.

The remaining preform was irradiated using Method B, as set forth in TABLE 8 above, with the substrate of the preform facing the irradiation source. With the preform in this position, the preform was exposed to a first, 100 kGy dose of irradiation. The preform was then placed in a convection oven which maintained a constant temperature of 110° C. After the expiration of four hours, the preform was removed from the convection oven and exposed to a second, 100 kGy dose of irradiation, for a total irradiation dose of 200 kGy.

Each of the preforms was then cut through the center and the substrate removed. The UHMWPE blend was then microtomed and subjected to FTIR analysis using a Bruker FTIR Spectrometer, available from Bruker Optics of Billerica, Mass., to determine the TVI of the UHMWPE blend. This analysis was performed on the thickest part of the specimens. A sample of the UHMWPE blend was then subjected to DSC using a TA Instruments Q1000, available from TA Instruments of New Castle, Del., to determine the percent crystallinity of the UHMWPE blend. This analysis was repeated for samples of the UHMWPE blend taken from different locations.

Figure 16:
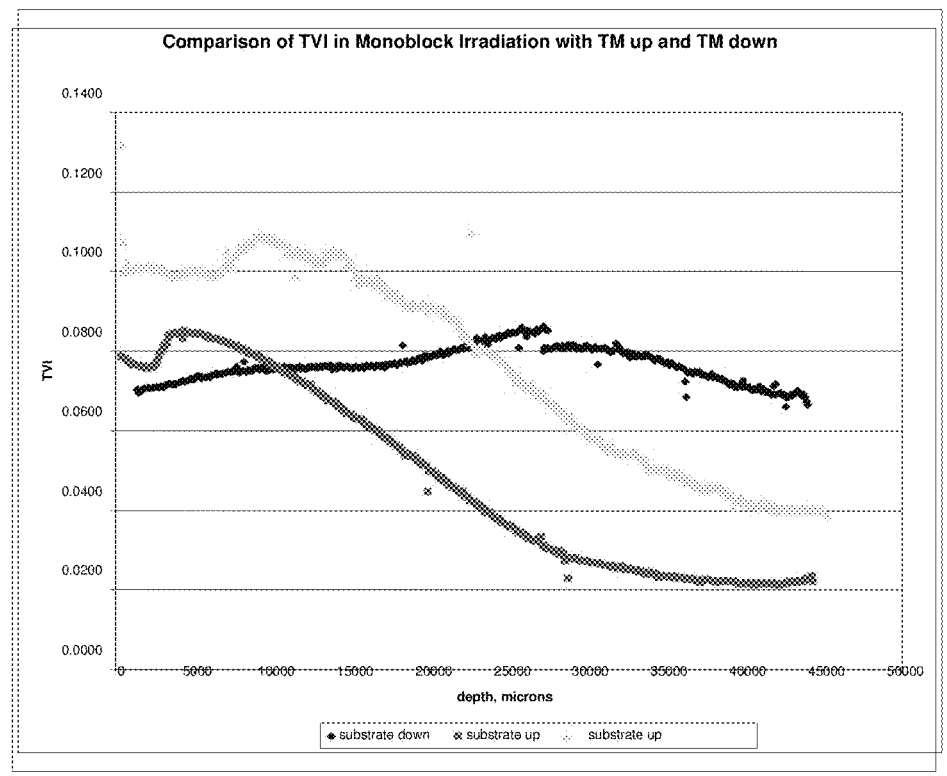
FIG. 16 depicts a graphical illustration of the trans-vinylene index of an irradiated monoblock component.

In both of the monoblocks that were irradiated with the substrate facing the irradiation source, a band of discoloration, i.e., translucence, can be seen along the edge of the UHMWPE blend that interfaced with the substrate. As shown in FIG. 16, the FTIR analysis showed a substantial decline in the TVI of the UHMWPE blend at a point just past the interface between the UHMWPE blend and the substrate. Additionally, the percent crystallinity at a point in the center of the UHMWPE blend was approximately 59%. The percent crystallinity decreased as the UHMWPE blend approached the interface with the substrate, with the percent crystallinity reaching 48% in the translucent region near the UHMWPE blend/substrate interface, as shown in TABLE 14 below. In the preform that was irradiated with the substrate facing away from the irradiation source, the TVI of the UHMWPE blend was substantially more uniform throughout the UHMWPE blend and the percent crystallinity varied by only 2.2%. This may be a result of more uniform crosslinking occurring in the preform in which the substrate faced away from the irradiation source during irradiation.

TABLE 14

Percent Crystallinity of UHMWPE Blend

| Specimen | % Crystallinity at the center of the UHMWPE Blend | % Crystallinity at the UHMWPE Blend/Substrate Interface |
| --- | --- | --- |
| Substrate Toward Irradiation Source | 59.29% | 48.67% |
| Substrate Toward Irradiation Source | 58.60% | 47.96% |
| Substrate Away from Irradiation Source | 59.88% | 57.66% |

Example 11

Effect of Irradiation Dose on UHMWPE Blend

Design Expert 6.0.10 software, obtained from Stat-Ease, Inc. Minneapolis, Minn., was utilized to setup a central composite response surface Design of Experiment (DOE). The DOE evaluated four different variables: d,l-α-tocopherol concentration, preheat temperature, total irradiation dose administered, and irradiation dose per pass.

GUR 1050 medical grade UHMWPE powder was obtained from Ticona, having North American headquarters in Florence, Ky. d/l-α-tocopherol was obtained from DSM Nutritional Products, Ltd of Geleen, Netherlands. The GUR 1050 was mechanically mixed with the d/l-α-tocopherol using a High Intensity Mixer, available from Eirich Machines of Gurnee, Ill. The GUR 1050 resin was mixed with the d/l-α-tocopherol in several batches to create UHMWPE blends having a selected wt. % of d/l-α-tocopherol. The wt. % of d/l-α-tocopherol was selected from 0.10 wt. %, 0.20 wt. %, 0.35 wt. %, 0.50 wt. %, and 0.60 wt. % d/l-α-tocopherol. Each of the blends was then compression molded into a substrate to create a preform. The substrate was a 70 mm outer diameter porous metal substrate in the form of a near-net shape acetabular shell. The porous metal substrate was produced using Trabecular Metal™ technology generally available from Zimmer, Inc., of Warsaw, Ind., and described in detail above.

The resulting preforms were then placed inside a piece of expandable braided polyethylene terephthalate sleeving and vacuum sealed inside an aluminum-metallized plastic film pouch, such a pouch formed from a polyethylene terephthalate resin, such as Mylar®, which has been coated with a metal, such as aluminum, to reduce gas diffusion rates through the film. Mylar is a registered trademark of DuPont Teijin Films U.S. Limited Partnership of Wilmington, Del. The preforms remained in this condition until they were removed in preparation for exposing the preforms to irradiation. Prior to irradiation, each of the resulting preforms was preheated by heating the preforms in a Grieve convection oven, available from The Grieve Corporation of Round Lake, Ill., to a preheat temperature, which was held for a minimum of 12 hours. The preheat temperature was selected from 60° C., 70° C., 85° C., 100° C., and 110° C., as set forth in TABLE 15 below.

The preforms were then exposed to a selected total irradiation dose according to Method B, as set forth above in TABLE 8. The total irradiation dose was selected from 133 kGy, 150 kGy, 175 kGy, 200 kGy, and 217 kGy. Additionally, the total irradiation dose was divided and administered to the preforms in either two equal passes or three equal passes, which are combined to achieve the total irradiation dose. Specifically, the preforms indicated to be "Block 1" in TABLE 15 below received the total irradiation dose in two equal passes, while the preforms indicated to be "Block 2" in TABLE 15 received the total irradiation dose in three equal passes.

After irradiation, each of the UHMWPE blends was separated from the substrate and three Pin-on-Disc (POD) specimens in the shape of cylinders having a 9 mm diameter and 13 mm thickness were then machined from the UHMWPE blend pucks. A bidirectional pin-on-disc wear tester was then used to measure the wear rate of UHMWPE pins articulating against polished cobalt-chrome discs lubricated by 100% bovine serum. These measurements were made in accordance with the teachings of Bragdon, C. R., et al., in *A new pin-on-disk wear testing method for simulating wear of polyethylene on cobalt-chrome alloy in total hip arthroplasty*, published in the Journal of Arthroplasty, Vol. 16, Issue 5, 2001, on pages 658-65, the entire disclosure of which is expressly incorporated by reference herein. The bidirectional motion for the pin-on-disc wear tester was generated by a computer controlled XY table, available from the Compumotor Division of Parker Hannifin of Cleveland, Ohio, which was programmed to move in a 10 mm by 5 mm rectangular pattern. Affixed atop the XY table was a basin containing six cobalt-chrome discs polished to an implant quality finish. The XY table and basin were mounted on a servo-hydraulic MTS machine, available from MTS of Eden Prairie, Minn. The MTS machine then loaded the UHMWPE blend pin specimens against the polished cobalt-chrome discs.

The MTS machine was programmed to produce a Paul-type curve [2] in synchronization with the motion of the XY table. A Paul-type curve is explained in detail in *Forces Transmitted By Joints in the Human Body* by J. P. Paul and published in the Proceedings Institution of Mechanical Engineers at Vol. 181, Part 37, pages 8-15, the entire disclosure of which is expressly incorporated by reference herein. The peak load of the Paul-type loading curve corresponded to a peak contact pressure of 6.5 MPa between each of the UHMWPE pin specimen and the cobalt-chrome discs. Tests were conducted at 2 Hz to a total of $1.128 \times 10^6$ cycles.

The remaining portions of the UHMWPE blends were cut in half to form microtome films that were subjected to FTIR analysis utilizing a Bruker Optics FTIR Spectrometer, available from Bruker Optics of Billerica, Mass. The films were then accelerated aged according to ASTM Standard F2003, Standard Guide for Accelerated Aging of Ultra-High Molecular Weight Polyethylene. The OI of the post-aged films was then measured.

Once the measurements were taken, the post-aged films were placed in boiling hexane for 24 hours to extract any d/l-α-tocopherol remaining in the films. The percentage of d/l-α-tocopherol extracted from the UHMWPE blend films was then determined. The remaining UHMWPE blend from the monoblock was then machined into 1/16" flats and Type V tensile specimens, as defined by ASTM Standard D638, Standard Test Method for Tensile Properties of Plastics, were machined from the flats.

An analysis of the results, set forth below in TABLE 15, indicated that wear increased with a lower total irradiation dose or with a higher concentration of d/l-α-tocopherol. Additionally, the d/l-α-tocopherol concentration had a significant impact on ultimate tensile elongation. The yield strength was affected the most by the preheat temperature, whereas UTS was affected the most by the total irradiation dose and d/l-α-tocopherol concentration. The OI was decreased with higher preheat temperatures and higher concentration of d/l-α-tocopherol. Although the percentage of d/l-α-tocopherol decreased after irradiation and aging, a significant amount of d/l-α-tocopherol still remained in the UHMWPE blend after irradiation and aging.

TABLE 15

Effect of Irradiation Dose on UHMWPE Blend

| Run | Block | Preheat (° C.) | Dose (kGy) | VE % | POD Wear (mg/Mc) |
|---|---|---|---|---|---|
| 1 | Block 1 | 100.00 | 200.00 | 0.20 | 1.01 |
| 2 | Block 1 | 100.00 | 150.00 | 0.50 | 3.84 |
| 3 | Block 1 | 100.00 | 150.00 | 0.20 | 1.59 |
| 4 | Block 1 | 100.00 | 200.00 | 0.50 | 1.78 |
| 5 | Block 2 | 59.77 | 175.00 | 0.35 | 1.97 |
| 6 | Block 1 | 70.00 | 150.00 | 0.20 | 1.76 |
| 7 | Block 1 | 70.00 | 200.00 | 0.20 | 0.80 |
| 8 | Block 1 | 70.00 | 150.00 | 0.50 | 3.91 |
| 9 | Block 1 | 70.00 | 200.00 | 0.50 | 2.38 |
| 10 | Block 2 | 110.23 | 175.00 | 0.35 | 2.05 |
| 11 | Block 2 | 85.00 | 132.96 | 0.35 | 3.32 |
| 12 | Block 2 | 85.00 | 175.00 | 0.60 | 2.34 |
| 13 | Block 2 | 85.00 | 175.00 | 0.10 | 0.58 |
| 14 | Block 2 | 85.00 | 175.00 | 0.35 | 2.28 |
| 15 | Block 2 | 85.00 | 217.04 | 0.35 | 1.06 |
| 16 | Block 1 | 85.00 | 175.00 | 0.35 | 1.94 |
| 17 | Block 2 | 85.00 | 175.00 | 0.35 | 2.30 |

| Run | Elongation % | YS (MPa) | UTS (MPa) | VE % (Aged) | OI (Aged) |
|---|---|---|---|---|---|
| 1 | 248.90 | 21.86 | 41.18 | 0.04 | 0.04 |
| 2 | 306.40 | 22.85 | 47.62 | 0.27 | 0.02 |
| 3 | 268.10 | 22.50 | 46.06 | 0.07 | 0.03 |
| 4 | 293.00 | 22.03 | 43.03 | 0.25 | 0.02 |
| 5 | 261.80 | 24.45 | 49.27 | 0.12 | 0.08 |
| 6 | 248.10 | 23.08 | 45.95 | 0.06 | 0.06 |
| 7 | 223.00 | 23.14 | 43.93 | 0.05 | 0.07 |
| 8 | 310.00 | 24.04 | 51.23 | 0.25 | 0.03 |
| 9 | 272.30 | 23.86 | 48.34 | 0.24 | 0.02 |
| 10 | 273.20 | 23.76 | 46.95 | 0.17 | 0.04 |
| 11 | 288.90 | 23.92 | 49.37 | 0.17 | 0.04 |
| 12 | 289.60 | 24.37 | 49.24 | 0.29 | 0.04 |
| 13 | 213.20 | 23.21 | 45.01 | −0.01 | 0.06 |
| 14 | 258.80 | 23.97 | 47.60 | 0.17 | 0.05 |
| 15 | 234.00 | 24.41 | 45.00 | 0.13 | 0.06 |
| 16 | 269.70 | 23.39 | 48.64 | 0.14 | 0.02 |
| 17 | 264.10 | 23.95 | 48.41 | 0.15 | 0.05 |

Example 12

Swell Ratio, Crosslink Density, and Molecular Weight Between Crosslinks

GUR 1050 medical grade UHMWPE powder was obtained from Ticona, having North American headquarters in Florence, Ky. d/l-α-tocopherol was obtained from DSM Nutritional Products, Ltd of Geleen, Netherlands. The GUR 1050 was mechanically blended with the d/l-α-tocopherol using a High Intensity Mixer, available from Eirich Machines of Gurnee, Ill. The GUR 1050 resin was mixed with the d/l-α-tocopherol to create UHMWPE blends having 0.2, 0.5, or 1.0 weight percent d/l-α-tocopherol. The UHMWPE blends were then compression molded to form pucks that were then machined to form cubes having 5 mm sides. The UHMWPE cubes were then heated to a preheat temperature selected from 40° C., 100° C., and 110° C. Once heated to the selected preheat temperature, the UHMWPE blends were irradiated using Method C, set forth in TABLE 8 above, until a total irradiation dose was received. The total irradiation dose was selected from of 90 kGy, 120 kGy, 150 kGy, and 200 kGy.

The resulting UHMWPE blend cubes were then studied to investigate the polymer network parameters of the UHMWPE blend by measuring the materials' swell ratio ($q_s$) with a Swell Ratio Tester (SRT), Cambridge Polymer Group (Boston, Mass.), in accordance with ASTM F-2214-02. Knowing $q_s$, the Flory interaction parameter ($\chi_1$), the molar volume of the solvent ($\phi_1$), and the specific volume of the solvent ($\bar{v}$), the crosslink density ($v_x$) and the molecular weight between crosslinks ($M_c$) of the material were calculated according the following equations:

$$v_x = -\frac{\ln(1 - q_s^{-1}) + q_s^{-1} + \chi_1 q_s^{-2}}{\varphi_1(q_s^{-1/3} - q_s^{-1}/2)}$$

$$M_c = \bar{v}v_x$$

Additionally, the swell ratio in stabilized o-xylene at 130° C. was measured in the compression molded direction. The results of the testing are set forth in TABLE 16 below. For example, it was found that a UHMWPE blend having nominally 1.0% weight percent of d/l-α-tocopherol when preheated to nominally 40° C. and subsequently electron beam crosslinked with a total dose of nominally 200 kGy has a $q_s$ less than about 4.3, a $v_x$ more than about 0.090 and a $M_c$ less than about 11,142. It was also found that a UHMWPE blend having nominally 1.0% weight percent of d/l-α-tocopherol when preheated to nominally 110° C. and subsequently electron beam crosslinked with a total dose of nominally 200 kGy has a $q_s$ less than about 3.6, a $v_x$ more than about 0.117 and a $M_c$ less than about 8,577.

Also, it was found that a UHMWPE blend having nominally 0.5 wt. % weight percent of d/l-α-tocopherol when preheated to nominally 40° C. and subsequently electron beam crosslinked with a total dose of nominally 200 kGy has a $q_s$ less than about 3.8, a $v_x$ more than about 0.119 and a $M_c$ less than about 8,421. It was also found that a UHMWPE blend having nominally 0.5% weight percent of d/l-α-tocopherol when preheated to nominally 110° C. and subsequently electron beam crosslinked with a total dose of nominally 200 kGy has a $q_s$ less than about 3.6, a $v_x$ more than about 0.109 and a $M_c$ less than about 9,166.

Further, it was found that a UHMWPE blend having nominally 0.2 wt. % of d/l-α-tocopherol when preheated to nominally 40° C. and subsequently electron beam crosslinked with a total dose of nominally 200 kGy has a $q_s$ less than about 2.8, a $v_x$ more than about 0.187 and a $M_c$ less than about 5,351. It was also found that the UHMWPE blend having nominally 0.2 wt. % of d/l-α-tocopherol when preheated to nominally 110° C. and subsequently electron beam crosslinked with a total dose of nominally 200 kGy has a $q_s$ less than about 3.0, a $v_x$ more than about 0.164 and a $M_c$ less than about 6,097.

Additionally, it was found that under some conditions the crosslinked UHMWPE blend exhibited a crosslink density of less than 0.200 moles/dm³. Under other conditions, the crosslinked UHMWPE blend having at least 0.1 wt. % antioxidant exhibited a crosslink density of less than 0.190 moles/dm³. Further, under certain conditions, the crosslinked UHMWPE blend having at least 0.1 wt. % antioxidant exhibited a crosslink density of more than 0.200 moles/dm³ and had a molecular weight between crosslinks of less than 11,200 daltons.

TABLE 16

Swell Ratio, Crosslink Density, and Molecular Weight Between Crosslinks

| RUN | MATERIAL TYPE | SAMPLE DOSE (kGy) | PRE-HEAT TEMP (° C.) | PERCENT VITAMIN E | DOSE RATE (kGy-m/min) |
|---|---|---|---|---|---|
| 1 | GUR 1020 | 90 | 40 | 0.2 | 75.00 |
| 2 | GUR 1050 | 90 | 100 | 0.2 | 75.00 |
| 3 | GUR 1050 | 150 | 40 | 0.2 | 75.00 |
| 4 | GUR 1020 | 150 | 100 | 0.2 | 75.00 |
| 5 | GUR 1020 | 90 | 40 | 1.0 | 75.00 |
| 6 | GUR 1020 | 90 | 100 | 0.5 | 75.00 |
| 7 | GUR 1020 | 150 | 40 | 0.5 | 75.00 |
| 8 | GUR 1020 | 150 | 100 | 1.0 | 75.00 |
| 9 | GUR 1050 | 90 | 40 | 0.2 | 240.00 |
| 10 | GUR 1020 | 90 | 100 | 0.2 | 240.00 |
| 11 | GUR 1020 | 150 | 40 | 0.2 | 240.00 |
| 12 | GUR 1050 | 150 | 100 | 0.2 | 240.00 |
| 13 | GUR 1050 | 90 | 40 | 1.0 | 240.00 |
| 14 | GUR 1020 | 90 | 100 | 1.0 | 240.00 |
| 15 | GUR 1020 | 150 | 40 | 1.0 | 240.00 |
| 16 | GUR 1020 | 150 | 100 | 0.5 | 240.00 |
| 17 | GUR 1050 | 120 | 40 | 0.5 | 157.50 |
| 18 | GUR 1050 | 120 | 100 | 1.0 | 157.50 |
| 19 | GUR 1050 | 120 | 40 | 1.0 | 157.50 |
| 20 | GUR 1050 | 120 | 100 | 1.0 | 157.50 |
| 21 | GUR 1050 | 90 | 40 | 1.0 | 75.00 |
| 22 | GUR 1050 | 90 | 100 | 0.5 | 75.00 |
| 23 | GUR 1050 | 150 | 40 | 0.5 | 75.00 |
| 24 | GUR 1050 | 150 | 100 | 1.0 | 75.00 |
| 25 | GUR 1050 | 90 | 40 | 0.5 | 240.00 |
| 26 | GUR 1050 | 90 | 100 | 1.0 | 240.00 |
| 27 | GUR 1050 | 150 | 40 | 1.0 | 240.00 |
| 28 | GUR 1050 | 150 | 100 | 0.5 | 240.00 |
| 29 | GUR 1050 | 2 × 100 = 200 | 40 | 0.2 | 240.00 |
| 30 | GUR 1050 | 2 × 100 = 200 | 110 | 0.2 | 240.00 |
| 31 | GUR 1050 | 2 × 100 = 200 | 40 | 1.0 | 240.00 |
| 32 | GUR 1050 | 2 × 100 = 200 | 110 | 1.0 | 240.00 |
| 33 | GUR 1050 | 2 × 100 = 200 | 40 | 0.5 | 240.00 |
| 34 | GUR 1050 | 2 × 100 = 200 | 110 | 0.5 | 240.00 |

| RUN | POD WEAR mg/1 M CYCLES | SWELL RATIO V/V0 = q(s) | X | Vx = XLD moles/dm^3 | Mc = MWbXL Daltons |
|---|---|---|---|---|---|
| 1 | | 5.09 | 0.44 | 0.068 | 14747 |
| 2 | | 3.40 | 0.49 | 0.129 | 7764 |
| 3 | 2.65 | 3.15 | 0.50 | 0.147 | 6812 |
| 4 | 1.13 | 4.61 | 0.45 | 0.079 | 12652 |
| 5 | | 6.15 | 0.42 | 0.051 | 19720 |
| 6 | | 5.52 | 0.43 | 0.060 | 16706 |
| 7 | | 4.22 | 0.46 | 0.091 | 11019 |
| 8 | | 5.52 | 0.43 | 0.060 | 16706 |
| 9 | | 3.75 | 0.48 | 0.110 | 9126 |
| 10 | | 4.49 | 0.45 | 0.082 | 12143 |
| 11 | | 3.84 | 0.47 | 0.105 | 9483 |
| 12 | 0.17 | 3.23 | 0.50 | 0.141 | 7115 |
| 13 | | 7.13 | 0.41 | 0.040 | 24747 |
| 14 | | 4.47 | 0.45 | 0.083 | 12059 |
| 15 | | 5.69 | 0.43 | 0.057 | 17502 |
| 16 | | 4.46 | 0.45 | 0.083 | 12017 |
| 17 | | 4.50 | 0.45 | 0.082 | 12185 |
| 18 | | 3.74 | 0.48 | 0.110 | 9087 |
| 19 | | 5.32 | 0.43 | 0.063 | 15785 |
| 20 | | 3.33 | 0.50 | 0.133 | 7496 |
| 21 | | 5.78 | 0.43 | 0.056 | 17929 |
| 22 | | 4.43 | 0.45 | 0.084 | 11891 |

TABLE 16-continued

Swell Ratio, Crosslink Density, and Molecular Weight Between Crosslinks

| 23 | 3.92 | 3.84 | 0.47 | 0.105 | 9483 |
|---|---|---|---|---|---|
| 24 | | 3.88 | 0.47 | 0.104 | 9642 |
| 25 | | 5.59 | 0.43 | 0.059 | 17033 |
| 26 | | 4.52 | 0.45 | 0.082 | 12270 |
| 27 | | 4.37 | 0.46 | 0.086 | 11640 |
| 28 | 1.63 | 3.65 | 0.48 | 0.115 | 8733 |
| 29 | 0.02 | 2.76 | 0.53 | 0.187 | 5351 |
| 30 | 0.09 | 2.96 | 0.52 | 0.164 | 6097 |
| 31 | 1.46 | 4.25 | 0.46 | 0.090 | 11142 |
| 32 | 0.64 | 3.61 | 0.48 | 0.117 | 8577 |
| 33 | | 3.57 | 0.48 | 0.119 | 8421 |
| 34 | | 3.76 | 0.48 | 0.109 | 9166 |

Example 13

Free Radical Concentrations in UHMWPE Blended with d/l-α-Tocopherol

The impact of mechanically blending d/l-α-tocopherol with UHMWPE powder on free radical concentration of electron beam irradiated UHMWPE blend molded pucks was investigated. To perform this investigation, Design Expert 6.0.10 software, obtained from Stat-Ease, Inc. Minneapolis, Minn., was utilized to setup a modified central composite Design of Experiment (DOE). The DOE evaluated five factors: preheat temperature, dose rate, irradiation dose, d/l-α-tocopherol concentration, and predetermined hold time, i.e., the time elapsed between removal of the UHMWPE blend from the oven until the initiation of electron beam irradiation.

GUR 1050 medical grade UHMWPE powder was obtained from Ticona, having North American headquarters in Florence, Ky. d/l-α-tocopherol was obtained from DSM Nutritional Products, Ltd. of Geleen, Netherlands. The GUR 1050 UHMWPE power was mechanically blended with the d/l-α-tocopherol by high intensity blending using an Eirich Mixer, available from Eirich Machines, Inc. of Gurnee, Ill. The GUR 1050 resin was mixed with the d/l-α-tocopherol in several batches to create UHMWPE blends having between 0.14 and 0.24 wt. % d/l-α-tocopherol, as set forth below in TABLE 17.

Each of the UHMWPE blends were then compression molded into 2.5 inch diameter and 1 inch thick pucks. Each of the resulting pucks was then preheated by heating in a Grieve convection oven, available from The Grieve Corporation of Round Lake, Ill., to a preheat temperature. The preheat temperature was selected from between 85° C. and 115° C., as set forth in TABLE 17 below. The pucks were then removed from the convection oven and held for a predetermined period of time ranging between 7 minutes and 21 minutes, as set forth in TABLE 17. After the expiration of the predetermined hold time, the pucks were electron beam irradiated utilizing Method A of TABLE 8. The pucks were irradiated at a dose rate selected from between 30 kGy-m/min and 75 kGy-m/min until a total dose selected from between 160 kGy and 190 kGy was administered, as set forth in TABLE 17. Cylindrical cores approximately 1 inch long were machined from the pucks. The cylindrical cores were then analyzed using a Bruker EMX/EPR (electron paramagnetic resonance) spectrometer, which has a detection limit of $0.01 \times 10^{15}$ spins/gram and is available from Bruker Optics of Billerica, Mass. The resulting analysis indicated that preheat temperature, percent d/l-α-tocopherol, and dose level were all significant factors in determining the resulting free radical concentration of the UHMWPE blend. Specifically, preheat temperature and d/l-

α-tocopherol concentration had a negative correlation with the free radical concentration, while the total dose had a positive correlation with the free radical concentration.

TABLE 17

Free Radical Concentration of UHMWPE Blends After Various Processing

| Run | Block | Preheat (° C.) | Dose (kGy) | VE % | Dose Rate (kGy-m/min.) | Oven to Beam (minutes) | Free radicals (spins/gram × E10-16) |
|---|---|---|---|---|---|---|---|
| 1 | Block 1 | 85 | 190 | 0.11 | 30 | 7 | 2.87 |
| 2 | Block 1 | 115 | 190 | 0.11 | 30 | 7 | 1.09 |
| 3 | Block 1 | 115 | 190 | 0.11 | 30 | 21 | 2.01 |
| 4 | Block 1 | 85 | 190 | 0.11 | 30 | 21 | 3.7 |
| 5 | Block 1 | 115 | 160 | 0.11 | 30 | 7 | 1.09 |
| 6 | Block 1 | 85 | 160 | 0.11 | 30 | 7 | 2.55 |
| 7 | Block 1 | 115 | 160 | 0.11 | 30 | 21 | 1.5 |
| 8 | Block 1 | 85 | 160 | 0.11 | 30 | 21 | 2.77 |
| 9 | Block 1 | 85 | 160 | 0.22 | 75 | 7 | 2.37 |
| 10 | Block 1 | 115 | 160 | 0.22 | 75 | 7 | 0.826 |
| 11 | Block 1 | 85 | 160 | 0.22 | 75 | 21 | 2.46 |
| 12 | Block 1 | 115 | 160 | 0.22 | 75 | 21 | 1.38 |
| 13 | Block 1 | 115 | 190 | 0.22 | 75 | 7 | 0.786 |
| 14 | Block 1 | 85 | 190 | 0.22 | 75 | 7 | 3.22 |
| 15 | Block 1 | 115 | 190 | 0.22 | 75 | 21 | 1.28 |
| 16 | Block 1 | 85 | 190 | 0.22 | 75 | 21 | 2.94 |
| 17 | Block 1 | 100 | 175 | 0.165 | 52.5 | 14 | 2.46 |
| 18 | Block 1 | 100 | 175 | 0.165 | 52.5 | 14 | 2.66 |
| 19 | Block 1 | 100 | 175 | 0.165 | 52.5 | 14 | 2.98 |
| 20 | Block 1 | 100 | 175 | 0.165 | 52.5 | 14 | 3.03 |

Example 14

Effect of UHMWPE Thickness on the Fatigue Behavior of Metal Backed Acetabular Cups The effect of reducing the thickness of an antioxidant stabilized UHMWPE layer in a metal backed acetabular cup design was investigated.

In order to prepare the test specimens, three Natural Cup™ metal acetabular shells made in accordance with Trabecular Metal™ technology, commercially available from Zimmer, Inc., of Warsaw, Ind., having a shell size of 54 mm and a head size of 40 mm, were obtained. The metal acetabular shells were compression molded with an antioxidant stabilized UHMWPE to form monoblock acetabular cups. The antioxidant stabilized UHMWPE of the acetabular cups was then crosslinked by exposing the antioxidant stabilized UHMWPE to crosslinking irradiation. The inner or articular surface formed by the antioxidant stabilized UHMWPE layer was then machined for receipt of a 40 mm femoral head. All of the test specimens were then cleaned to remove particles from the machining operation.

Figure 17:
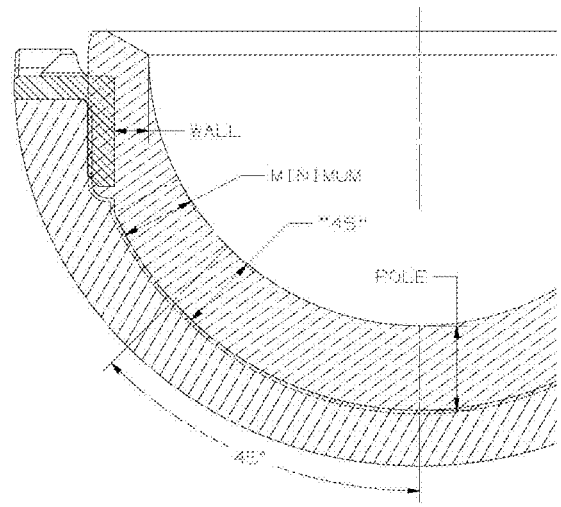
FIG. 17 is a fragmentary, cross-sectional view of an acetabular cup construct depicting exemplary thickness measurements of a UHMWPE layer.

The thickness of the antioxidant stabilized UHMWPE layer of an acetabular cup is dependent on the specific shell size used and the desired femoral head size for a particular acetabular cup configuration. Additionally, the thickness of the antioxidant stabilized UHMWPE layer is dependent upon the position at which the thickness of the UHMWPE layer is measured. In order to facilitate a comparison of the test results, several different thickness measurements were taken for each of the acetabular cups in the test. Specifically, for the purposes of this Example, the "Minimum Thickness" is defined as the thickness of the antioxidant stabilized UHMWPE layer measured from a point on the metal shells that is just below the titanium ring, which is formed at the equator of the Natural Cup™ metal acetabular shells, to a line tangent to the radius of the articular surface formed by the antioxidant stabilized UHMWPE layer, as shown in FIG. 17 as "MINIMUM". A second measurement, referred to as the "Wall Thickness", is defined, for purposes of this Example, as the thickness of the antioxidant stabilized UHMWPE layer measured from the inner edge of the titanium ring of the Natural Cup™ metal acetabular shells to the outermost point of the articular surface formed by the antioxidant stabilized UHMWPE layer, as shown in FIG. 17 as "WALL". In addition, the thickness of the antioxidant stabilized UHMWPE layer at the pole of the cup and at a point that is 45° from the pole of the cup were also measured, as shown in FIG. 17 as "POLE" and "45", respectively. Based on the results of the measurements, the antioxidant stabilized UHMWPE layer had a minimum thickness of 3.66 mm, a Wall Thickness of 1.33 mm, a thickness at the pole of the cup of 4.49 mm, and a thickness at a point that is 45° from the pole of the cup of 4.05 mm.

Once prepared, each of the three acetabular cups was then potted in a block of poly methyl meth acrylate bone cement in a position such that each of the cups had an inclination angle of 60°. The 60° inclination angle was selected to capture a clinically relevant, but clinically steep, abduction angle. The cup specimens were then placed in a de-ionized water bath maintained at a temperature of 37±1° C. and subjected to uniaxial loading on a MTS 858 Mini Bionix uniaxial fatigue test machine, commercially available from MTS Systems Corporation of Eden Prairie, Minn. The temperature of 37±1° C. is representative of the in vivo environment, which is appropriate due to the temperature-dependency of the mechanical properties of the UHMWPE.

The uniaxial loading was applied as a cyclic compressive force using a Cobalt-Chromium-Molybdenum femoral head component, with a minimum/maximum stress ratio of R=0.1. The tests were be performed at a frequency of 3 Hz, with the first cup subjected to a force of 1000 lbs, the second cup subjected to a force of 1350 lbs, and the third cup subjected to a force of 1700 lbs, until reaching a stopping point of 5 million cycles or fracture, whichever occurs first. Once the tests were completed, each of the three acetabular cups were visually inspected for damage to the antioxidant stabilized UHMWPE layer and the porous metal layer.

In contrast to traditional crosslinked UHWMPE acetabular cups made with a thicker UHMWPE layer, such as a UHMWPE layer of at least 6 mm, the acetabular cups of the present investigation all survived the testing, i.e., the stopping point of 5 million cycles was reached, and no deformation of the antioxidant stabilized UHMWPE layer or the porous metal layer was observed. In contrast, traditional crosslinked UHMWPE acetabular cups made with a fiber metal shell and having a UHMWPE layer that is not antioxidant stabilized and a thickness of approximately 6 mm have a fatigue strength of approximately 1400 lbs., as measured in a substantially similar manner as indicated above. Thus, the use of an antioxidant stabilized UHMWPE layer allows for the acetabular cups of the present invention to have a UHMWPE layer that has a thickness that is substantially less than the UHMWPE layer thickness of conventional acetabular cups, while also providing an increase in the fatigue strength of the same.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An acetabular component configured for use in a hip replacement surgery, the acetabular component comprising:
   a porous layer configured to contact and interface with bone tissue when the acetabular component is implanted;
   an inner layer formed from an antioxidant stabilized crosslinked ultrahigh molecular weight polyethylene and having a thickness of less than six millimeters, said inner layer configured to receive a femoral component; and
   an interdigitation layer defined by the distance over which said antioxidant stabilized crosslinked ultrahigh molecular weight polyethylene of said inner layer infiltrates pores of said porous layer,
   wherein the antioxidant stabilized crosslinked ultrahigh molecular weight polyethylene is prepared by a process that includes
      combining ultrahigh molecular weight polyethylene with an antioxidant to form a blend;
      processing the blend to consolidate the blend, wherein the consolidated blend has a melting point;
      preheating the consolidated blend to a preheat temperature below the melting point of the consolidated blend; and
      irradiating the preheated consolidated blend while maintaining the consolidated blend at a temperature below the melting point of the consolidated blend;
   wherein the antioxidant is substantially uniformly distributed throughout the antioxidant stabilized crosslinked ultrahigh molecular weight polyethylene.

2. The acetabular component of claim 1, wherein said inner layer has a thickness substantially equal to two millimeters.

3. The acetabular component of claim 1, wherein said porous layer has a porosity of at least 55 percent.

4. The acetabular component of claim 1, wherein said porous layer is defined by a porous metal having an elastic modulus of less than 15 GPa.

5. The acetabular component of claim 1, further comprising an effective stiffness between 0.1 GPa and 10 GPa.

6. The acetabular component of claim 1, further comprising an effective stiffness between 0.3 GPa and 1.5 GPa.

7. The acetabular component of claim 1, wherein said inner layer has a thickness of less than four millimeters.

8. The acetabular component of claim 1, wherein the blend includes between 0.1 and 3.0 weight percent antioxidant.

9. The acetabular component of claim 8, wherein the preheated consolidated blend is irradiated with a total irradiation dose of between 90 kGy and 1000 kGy.

10. The acetabular component of claim 9, wherein the antioxidant is tocopherol.

11. The acetabular component of claim 10, wherein the consolidated blend is secured to the porous layer prior to irradiation.

12. The acetabular component of claim 11, wherein said inner layer has a thickness of less than four millimeters.

13. The acetabular component of claim 12, wherein said porous layer has a porosity of at least 55 percent.

14. The acetabular component of claim 13, wherein said porous layer is defined by a porous metal having an elastic modulus of less than 15 GPa.

15. The acetabular component of claim 14, further comprising an effective stiffness between 0.1 GPa and 10 GPa.

16. The acetabular component of claim 15, further comprising an effective stiffness between 0.3 GPa and 1.5 GPa.

17. The acetabular component of claim 16, wherein said inner layer has a thickness substantially equal to two millimeters.

18. An acetabular component configured for use in a hip replacement surgery, the acetabular component comprising:
   a porous layer configured to contact and interface with bone tissue when the acetabular component is implanted, wherein the porous layer has a porosity of at least 55 percent;
   an inner layer formed from an antioxidant stabilized crosslinked ultrahigh molecular weight polyethylene and having a thickness of less than four millimeters, wherein the inner layer is configured to receive a femoral component; and
   an interdigitation layer defined by the distance over which said antioxidant stabilized crosslinked ultrahigh molecular weight polyethylene of said inner layer infiltrates pores of said porous layer,
   wherein the acetabular component has an effective stiffness of between 0.3 GPa and 1.5 GPa and the antioxidant stabilized crosslinked ultrahigh molecular weight polyethylene is prepared by a process that includes
      combining ultrahigh molecular weight polyethylene with tocopherol to form a blend having between 0.1 and 3.0 weight percent tocopherol;
      processing the blend to consolidate the blend, wherein the consolidated blend has a melting point;
      preheating the consolidated blend to a preheat temperature below the melting point of the consolidated blend; and
      irradiating the preheated consolidated blend with a total irradiation dose of between 90 kGy and 1000 kGy while maintaining the consolidated blend at a temperature below the melting point of the consolidated blend, wherein the consolidated blend is secured to the porous layer prior to irradiation;
   wherein the tocopherol is substantially uniformly distributed throughout the antioxidant stabilized crosslinked ultrahigh molecular weight polyethylene.

19. The acetabular component of claim 18, wherein the inner layer exhibits no visible deformations after undergoing 5 million cycles of uniaxial loading under at least 1,000 pounds of force.

* * * * *

UNITED STATES PATENT AND TRADEMARK OFFICE
CERTIFICATE OF CORRECTION

PATENT NO. : 8,652,212 B2
APPLICATION NO. : 12/362159
DATED : February 18, 2014
INVENTOR(S) : Case et al.

It is certified that error appears in the above-identified patent and that said Letters Patent is hereby corrected as shown below:

Title Page, References Cited

On page 3, in column 1, under "Other Publications", line 24, delete "Degration"," and insert --Degradation",--, therefor On page 3, in column 2, under "Other Publications", line 18, delete "y-irradiated" and insert --γ-irradiated--, therefor On page 4, in column 2, under "Other Publications", line 47, delete "(EXH2O)," and insert --(EXH20),--, therefor In the Claims Column 39, line 20, in Claim 1, delete "includes" and insert --includes:--, therefor Column 40, line 31, in Claim 18, delete "includes" and insert --includes:--, therefor Signed and Sealed this
Sixteenth Day of September, 2014

Michelle K. Lee
*Deputy Director of the United States Patent and Trademark Office*